United States Patent
You et al.

(10) Patent No.: US 12,304,961 B2
(45) Date of Patent: May 20, 2025

(54) PD-L1 AND OX40 BINDING PROTEINS FOR CANCER REGULATION

(71) Applicant: AP Biosciences, Inc., Taipei (TW)

(72) Inventors: Jhong-Jhe You, Taipei (TW);
Ching-Hsuan Hsu, Taoyuan (TW);
Po-Lin Huang, Taipei (TW);
Hung-Tsai Kan, New Taipei (TW);
Ting-Yi Chang, New Taipei (TW);
Hsin-Ta Hsieh, Taipei (TW);
Jeng-Horng Her, San Jose, CA (US)

(73) Assignee: AP Biosciences, Inc., Taipei (TW)

( * ) Notice: Subject to any disclaimer, the term of this patent is extended or adjusted under 35 U.S.C. 154(b) by 5 days.

(21) Appl. No.: 18/181,339

(22) Filed: Mar. 9, 2023

(65) Prior Publication Data
US 2023/0322939 A1    Oct. 12, 2023

Related U.S. Application Data

(63) Continuation of application No. 16/871,799, filed on May 11, 2020, now Pat. No. 11,643,470, which is a continuation of application No. PCT/US2018/067868, filed on Dec. 28, 2018.

(60) Provisional application No. 62/611,543, filed on Dec. 29, 2017.

(51) Int. Cl.
*A61K 39/395* (2006.01)
*A61P 35/00* (2006.01)
*C07K 16/28* (2006.01)
*A61K 39/00* (2006.01)

(52) U.S. Cl.
CPC .......... *C07K 16/2878* (2013.01); *A61P 35/00* (2018.01); *C07K 16/2827* (2013.01); *A61K 2039/505* (2013.01); *C07K 2317/31* (2013.01); *C07K 2317/52* (2013.01); *C07K 2317/55* (2013.01); *C07K 2317/622* (2013.01)

(58) Field of Classification Search
None
See application file for complete search history.

(56) References Cited

U.S. PATENT DOCUMENTS

| | | |
|---|---|---|
| 5,541,297 A | 7/1996 | Hansen et al. |
| 7,550,140 B2 | 6/2009 | Bakker et al. |
| 7,943,743 B2 | 5/2011 | Korman et al. |

(Continued)

FOREIGN PATENT DOCUMENTS

| | | |
|---|---|---|
| CN | 104080809 A | 10/2014 |
| CN | 104470949 A2 | 3/2015 |

(Continued)

OTHER PUBLICATIONS

Reeck, "Homology' in Proteins and Nucleic Acids: A Terminology Muddle and A Way out of it" (Letter to the Editor), Cell, 1987, vol. 50, Cell Press.

(Continued)

*Primary Examiner* — Claire Kaufman
(74) *Attorney, Agent, or Firm* — The Webb Law Firm

(57) ABSTRACT

Provided are monospecific and bispecific proteins that bind specifically to OX40 and/or PD-L1. Exemplary proteins release the inhibition through PD-L1 and stimulate T cell through OX40. Exemplary polyvalent proteins comprise at least one OX40 binding site and at least one PD-L1 binding site. In certain embodiments, the binding sites may be linked through an immunoglobulin constant region. Anti-OX40 and anti-PD-L1 antibodies are also provided.

19 Claims, 33 Drawing Sheets
Specification includes a Sequence Listing.

(56) References Cited

U.S. PATENT DOCUMENTS

| | | | |
|---|---|---|---|
| 7,960,515 | B2 | 6/2011 | Min et al. |
| 9,006,399 | B2 | 4/2015 | Liu et al. |
| 9,175,082 | B2 | 11/2015 | Zhou et al. |
| 9,475,880 | B2 | 10/2016 | Simons et al. |
| 9,856,320 | B2 | 1/2018 | Cogswell et al. |
| 10,058,609 | B2 | 8/2018 | Zhou et al. |
| 10,457,732 | B2 | 10/2019 | Kasturirangan et al. |
| 11,117,972 | B2 | 9/2021 | Eckelman et al. |
| 2015/0307617 | A1 | 10/2015 | Du et al. |
| 2016/0166685 | A1 | 6/2016 | Cheung et al. |
| 2017/0198051 | A1 | 7/2017 | Eckelman et al. |
| 2017/0275362 | A1 | 9/2017 | Brentjens et al. |
| 2017/0281765 | A1 | 10/2017 | Zhou et al. |
| 2018/0147271 | A1 | 5/2018 | Morgan et al. |
| 2018/0327504 | A1 | 11/2018 | Al-Shamkhani et al. |
| 2018/0346571 | A1 | 12/2018 | Gurney et al. |
| 2019/0112380 | A1 | 4/2019 | Chaudhary |
| 2020/0299389 | A1 | 9/2020 | Her et al. |

FOREIGN PATENT DOCUMENTS

| | | |
|---|---|---|
| CN | 104736168 A | 6/2015 |
| CN | 106103486 A | 11/2016 |
| CN | 106999583 A | 8/2017 |
| CN | 107074953 A | 8/2017 |
| JP | 2008544755 A | 12/2008 |
| JP | 2011505836 A | 3/2011 |
| JP | 2013538057 A | 10/2013 |
| JP | 2014527814 A | 10/2014 |
| JP | 2015519375 A | 7/2015 |
| JP | 2017514461 A | 6/2017 |
| WO | 03106498 A2 | 12/2003 |
| WO | 2013038191 A2 | 3/2013 |
| WO | 2013181634 A2 | 12/2013 |
| WO | 2016090337 A1 | 6/2016 |
| WO | 2016187216 A1 | 11/2016 |
| WO | 2017068181 A1 | 4/2017 |
| WO | 2017087547 A1 | 5/2017 |
| WO | 2017096120 A1 | 6/2017 |
| WO | 2017123673 A2 | 7/2017 |
| WO | 2017172981 A2 | 10/2017 |
| WO | 2017193032 A2 | 11/2017 |
| WO | 2019168947 A1 | 9/2019 |
| WO | 2019184909 A1 | 10/2019 |

OTHER PUBLICATIONS

Rudikoff et al., "Single amino acid substitution altering antigen-binding specificity," 1982, Proc Natl Acad Sci. USA, vol. 79, pp. 1979-1983.

Tamura et al., "Structural Correlates of an Anticarcinoma Antibody: Identification of Specificity-Determining Residues (SDRs) and Development of a Minimally Immunogenic Antibody Variant by Retention of SDRs Only," 2000, J Immunol., vol. 164, pp. 1432-1441.

Yarilin, "The Principles of Immunology", Moscow: Meditsina, 1999, pp. 169-174, vol. 608.

Dondelinger et al., "Understanding the Significance and Implications of Antibody Numbering and Antigen-Binding Surface/Residue Definition", Frontiers in Immunology, 2018, vol. 9, doi.org/10.3389/fimmu.2018.02278.

Tingsong, "Advances in Treatment of Gastric Cancer", Tongji University Press, May 31, 2017, p. 144.

Zhang et al., "Fc Engineering Approaches to Enhance the Agonism and Effector Functions of an Anti-OX40 Antibody", Journal of Biological Chemistry, pp. 27134-27146, vol. 291(53).

Weinberg et al., "Anti-OX40 (CD134) administration to nonhuman primates: immunostimulatory effects and toxicokinetic study", Journal of Immunotherapy, Nov.-Dec. 2006, vol. 29(6), pp. 575-585.

Guo et al., "PD-1 Blockade and OX40 Triggering Synergistically Protects against Tumor Growth in a Murine Model of Ovarian Cancer", PLOS ONE, Feb. 27, 2014, vol. 9(2).

Granier et al., "Mechanisms of action and rationale for the use of checkpoint inhibitors in cancer", ESMO Open, 2017.

Shrimali et al., "Concurrent PD-1 Blockade Negates the Effects of OX40 Agonist Antibody in Combination Immunotherapy through Inducing T-cell Apoptosis", Cancer Immunology Research, 2017, pp. 755-766.

Hui et al., "Research on an anti-human OX40 eliciting monoclonal antibody and preliminary study on its biological ability", Modern Immunology, May 31, 2010, pp. 195-201, vol. 30(3).

Wei et al., "Comprehensive therapeutic strategies regarding immune checkpoint", Chin J Clin Oncol, Aug. 15, 2017, pp. 782-786, vol. 44(15).

Ping et al., "Research progress of new target OX40 in tumor immunotherapy", Chinese Journal of Microbiology and Immunology, Mar. 31, 2017, pp. 240-244, vol. 37(3).

Geng et al., "Advances in the application of bispecific antibody drugs", Progress in Biotechnology, Nov. 25, 2015, pp. 420-424, vol. 5(6).

Nagaya et al., "Near infrared photoimmunotherapy with avelumab, an anti-programmed death-ligand 1 (PD-L1) antibody", Oncotarget, 2017, pp. 8807-8817, vol. 8, No. 5.

Bargou et al., "Tumor Regression in Cancer Patients by Very Low Doses of a T Cell-Engaging Antibody", Science, 2008, pp. 974-977, vol. 321, No. 5891.

Bretscher et al., "A Theory of Self-Nonself Discrimination", Science, 1970, pp. 1042-1049, vol. 169, No. 3950.

Bretscher, "A two-step, two-signal model for the primary activation of precursor helper T cells", Proceedings of the National Academy of Sciences of the United States of America, 1999, pp. 185-190, vol. 96, No. 1.

Chames et al., "Bispecific antibodies for cancer therapy: The light at the end of the tunnel?", mAbs, 2009, pp. 539-547, vol. 1, No. 6.

Croft, "Costimulation of T cells by OX40, 4-1BB, and CD27", Cytokine & Growth Factor Reviews, 2003, pp. 265-273. vol. 14, Nos. 3-4.

Demarest et al., "Antibody therapeutics, antibody engineering, and the merits of protein stability", Current Opinion in Drug Discovery & Development, 2008, pp. 675-687, vol. 11, No. 5.

Fridman et al., "The immune contexture in human tumours: impact on clinical outcome", Nature Reviews, Cancer, 2012, pp. 298-306, vol. 12, No. 4.

Goldenberg et al., "Cancer imaging and therapy with bispecific antibody pretargeting", Update on Cancer Therapeutics, 2007, pp. 19-31, vol. 2, No. 1.

Heiss et al., "The trifunctional antibody catumaxomab for the treatment of malignant ascites due to epithelial cancer: results of a prospective randomized phase II/III trial", International Journal of Cancer, 2010, pp. 2209-2221, vol. 127, No. 9.

Hollander, "Bispecific antibodies for cancer therapy", Immunotherapy, 2009, pp. 211-222, vol. 1, No. 2.

Jenkins et al., "Antigen Presentation by Chemically Modified Splenocytes Induces Antigen-Specific T Cell Unresponsiveness in Vitro and in Vivo", Journal of Experimental Medicine, 1987, pp. 302-319, vol. 165, No. 2.

Karpovsky et al., "Production of target-specific effector cells using hetero-cross-linked aggregates containing anti-target cell and anti-Fc gamma receptor antibodies", Journal of Experimental Medicine, 1984, pp. 1686-1701, vol. 160, No. 6.

King et al., "A new Hu-PBL model for the study of human islet alloreactivity based on NOD-scid mice bearing a targeted mutation in the IL-2 receptor gamma chain gene", Clinical Immunology, 2008, pp. 303-314, vol. 126, No. 3.

Lafferty et al., "A New Analysis of Allogeneic Interactions", The Australian Journal of Experimental Biology and Medical Science, 1975, pp. 27-42, vol. 53, Pt. 1.

Larkin et al., "Combined Nivolumab and Ipilimumab or Monotherapy in Untreated Melanoma", The New England Journal of Medicine, 2015, pp. 23-34, vol. 373, No. 1.

Lenschow et al., "CD28/B7 System of T Cell Costimulation", Annual Review of Immunology, 1996, pp. 233-258, vol. 14.

Liang et al., "PD-L1 and PD-L2 have distinct roles in regulating host immunity to cutaneous leishmaniasis", European Journal of Immunology, 2006, pp. 58-64, vol. 36, No. 1.

(56) References Cited

OTHER PUBLICATIONS

Linch et al., "OX40 agonists and combination immunotherapy: putting the pedal to the metal", Frontiers in Oncology, 2015, 14 pages, vol. 5, Article No. 34.

Lu et al., "A Fully Human Recombinant IgG-like Bispecific Antibody to Both the Epidermal Growth Factor Receptor and the Insulin-like Growth Factor Receptor for Enhanced Antitumor Activity", The Journal of Biological Chemistry, 2005, pp. 19665-19672, vol. 280, No. 20.

Müller et al., "Improved Pharmacokinetics of Recombinant Bispecific Antibody Molecules by Fusion to Human Serum Albumin", The Journal of Biological Chemistry, 2007, pp. 12650-12660, vol. 282, No. 17.

Pardoll, "The blockade of immune checkpoints in cancer immunotherapy", Nature Review, Cancer, 2012, pp. 252-264, vol. 12, No. 4.

Paterson et al., "Antigens of Activated Rat T Lymphocytes Including a Molecule of 50,000 Mr Detected Only on CD4 Positive T Blasts", Molecular Immunology, 1987, pp. 1281-1290, vol. 24, No. 12.

Perez et al., "Specific targeting of cytotoxic T cells by anti-T3 linked to anti-target cell antibody", Nature, 1985, pp. 354-356, vol. 316, No. 6026.

Ridgway et al., "Knobs-into-holes' engineering of antibody CH3 domains for heavy chain heterodimerization", Protein Engineering, 1996, pp. 617-621, vol. 9, No. 7.

Staerz et al., "Hybrid antibodies can target sites for attack by T cells", Nature, 1985, pp. 628-631, vol. 314, No. 6012.

Sznol et al., "Antagonist Antibodies to PD-1 and B7-H1 (PD-L1) in the Treatment of Advanced Human Cancer", Clinical Cancer Research, 2013, pp. 1021-1034, vol. 19, No. 5.

Thakur et al., "Cancer therapy with bispecific antibodies: Clinical experience", Current Opinion in Molecular Therapeutics, 2010, pp. 340-349, vol. 12, No. 3.

Topalian et al., "Survival, Durable Tumor Remission, and Long-Term Safety in Patients With Advanced Melanoma Receiving Nivolumab", Journal of Clinical Oncology, 2014, pp. 1020-1030, vol. 32, No. 10.

Watts, "TNF/TNFR Family Members in Costimulation of T Cell Responses", Annual Review of Immunology, 2005, pp. 23-68, vol. 23.

Weinberg et al., "Target Organ-Specific Up-Regulation of the Mrc OX-40 Marker and Selective Production of Th1 Lymphokine mRNA by Encephalitogenic T Helper Cells Isolated from the Spinal Cord of Rats with Experimental Autoimmune Encephalomyelitis", Journal of Immunology, 1994, pp. 4712-4721, vol. 152, No. 9.

"Atezolizumab", Wikipedia, pp. 1-5, retrieved from https://en.wikipedia.org/wiki/Atezolizumab on May 4, 2021.

Azevedo et al., "First-line atezolizumab monotherapy in patients with advanced BRAFV600 wild-type melanoma", Pigment Cell & Melanoma Research, 2021. [Abstract].

Bahleda et al., "Long-Term Safety and Clinical Outcomes of Atezolizumab in Head and Neck Cancer: Phase 1a Trial Results", Annals of Oncology, Sep. 2017, pp. 373, vol. 28:5. [Abstract].

Geoerger et al., "Atezolizumab for children and young adults with previously treated solid tumours, non-Hodgkin lymphoma, and Hodgkin lymphoma (iMATRIX): a multicentre phase 1-2 study", The Lancet Oncology, 2019, pp. 134-144, vol. 21:1.

"Highlights of Prescribing Information: Tecentriq (atezolizumab) injection, for intravenous use", U.S. Food and Drug Administration, 2016, pp. 1-38.

Lafon et al., "Atezolizumab for the treatment of renal cell carcinoma", Expert Opinion on Biological Therapy, 2020, pp. 679-686, vol. 20:7.

Petrylak et al., "Safety and Clinical Activity of Atezolizumab in Patients with Metastatic Castration-Resistant Prostate Cancer: A Phase I Study", Clinical Cancer Research, 2021, pp. 3360-3369, vol. 27:12.

Rico et al., "Atezolizumab for the treatment of colorectal cancer: the latest evidence and clinical potential", Expert Opinion on Biological Therapy, 2018, pp. 449-457, vol. 18:4.

Bulliard et al., "OX40 engagement depletes intratumoral Tregs via activating FcγRs, leading to antitumor efficacy", Immunology and Cell Biology, 2014, pp. 475-480, vol. 92.

Lee et al. "Molecular mechanism of PD-1/PD-L1 blockade via anti-PD-L1 antibodies atezolizumab and durvalumab", Scientific Reports, pp. 1-12, vol. 7.

Alves Costa Silva et al., "New pathways in immune stimulation: targeting OX40," ESMO Open, 2020, pp. 1-8, vol. 5, article No. e000573.

Bell et al., "OX40 signaling in head and neck squamous cell carcinoma: Overcoming immunosuppression in the tumor microenvironment," Oral Oncology, 2016, pp. 1-10, vol. 52.

Ramser et al., "High OX40 expression in recurrent ovarian carcinoma is indicative for response to repeated chemotherapy," BMC Cancer, 2018, pp. 1-9, vol. 18, article No. 425.

Yokouchi et al., "Anti-OX40 monoclonal antibody therapy in combination with radiotherapy results in therapeutic antitumor immunity to murine lung cancer," Cancer Sci., 2008, pp. 361-367, vol. 99:2.

Chen et al., "Enhancement and destruction of antibody function by somatic mutation: unequal occurrence is controlled by V gene combinatorial associations", The EMBO Journal, 1995, pp. 2784-2794, vol. 14, No. 12, Oxford University Press.

Kranz et al., "Restricted reassociation of heavy and light chains from hapten-specific monoclonal antibodies", Proc. Natl. Acad. Sci. USA, 1981, pp. 5807-5811, vol. 78, No. 9.

Amminmaki et al., "Crystal Structure of a Recombinant Anti-estradiol Fab Fragment in Complex with 17(beta)-Estradiol", The Journal of Biological Chemistry, 2001, pp. 36687-36694, vol. 276, No. 39, The American Society for Biochemistry and Molecular Biology, Inc.

MacCallum et al., "Antibody-antigen Interactions: Contact Analysis and Binding Site Topography", J. Mol. Biol., 1996, pp. 732-745, Academic Press Limited.

Nezlin, "Biochmistry of Antibodies", 1970, p. 160, Plenum Press: New York.

Pearson, "An Introduction to Sequence Similarity ('Homology') Searching", Current Protocols in Bioinformatics, 2013, pp. 1-8, John Wiley & Sons, Inc.

Tan et al., "Distinct PD-L1 binding characteristics of therapeutic monoclonal antibody durvalumab", Protein & Cell, vol. 9, Issue 1, Jan. 2018, pp. 135-139.

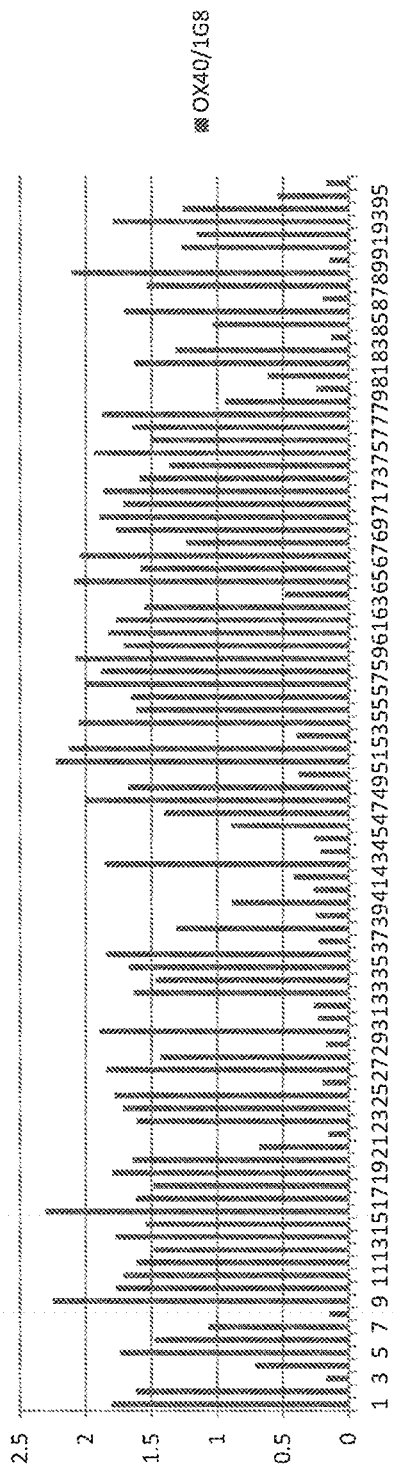
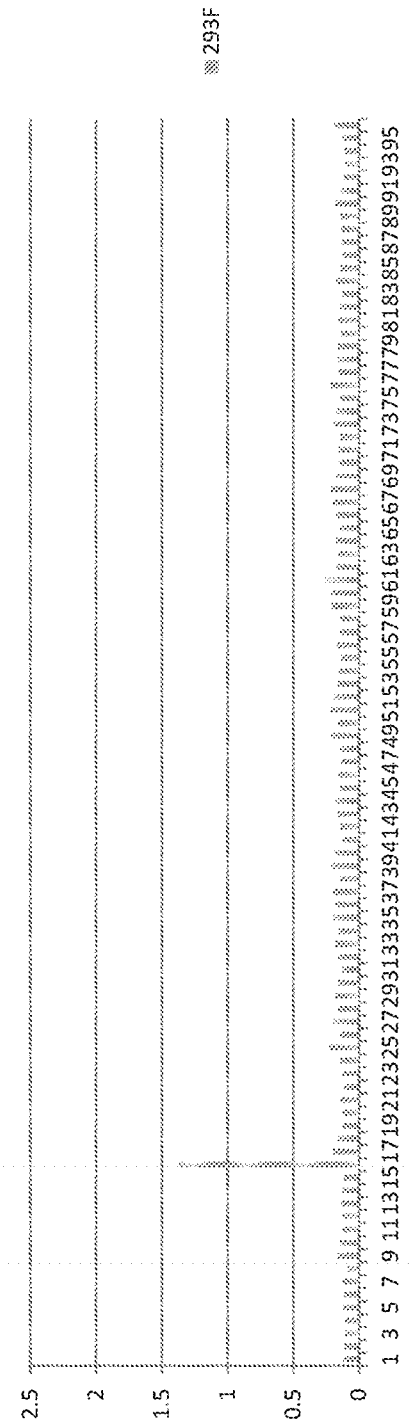
Fig. 3A
Fig. 3B

Fig. 18

SEQUENCE LISTING

```
Sequence total quantity: 43
SEQ ID NO: 1            moltype = AA  length = 217
FEATURE                 Location/Qualifiers
source                  1..217
                        mol_type = protein
                        organism = Homo sapiens
SEQUENCE: 1
QSVLTQPPSA SGTPGQRVTI SCSGSSSNIG SNTVNWYQQL PGTAPKLLIY SNNQRPSGVP   60
DRFSGSKSGT SASLAISGLQ SEDEADYYCA TWDDSLNAWV VFGGGTKLTV LGQPKAAPSV  120
TLFPPSSEEL QANKATLVCL ISDFYPGAVT VAWKADSSPV KAGVETTTPS KQSNNKYAAS  180
SYLSLTPEQW KSHRSYSCQV THEGSTVEKT VAPTECS                           217

SEQ ID NO: 2            moltype = AA  length = 118
FEATURE                 Location/Qualifiers
source                  1..118
                        mol_type = protein
                        organism = Homo sapiens
SEQUENCE: 2
QVQLVQSGAE VKKPGSSVKV SCKASGGTFR RYSISWVRQA PGQGLEWMGG IIPVFGAAKY   60
AQKFQGRVTI TADEFTSTAY MELSSLTSED TAVYYCALSS DSDAFDIWGQ GTMVTVSS    118
```

```
SEQ ID NO: 3              moltype = AA   length = 216
FEATURE                   Location/Qualifiers
source                    1..216
                          mol_type = protein
                          organism = Homo sapiens
SEQUENCE: 3
QSALTQPASV SGSPGQSITI SCTGTSNDVG SYNSVSWYQQ HPGKAPKLVI YEVANRPSGV    60
PDRFSGSKSG NTASLTISGL QAEDEADYYC SSYTSSSTLV FGGGTKLTVL GQPKAAPSVT   120
LFPPSSEELQ ANKATLVCLI SDFYPGAVTV AWKADSSPVK AGVETTTPSK QSNNKYAASS   180
YLSLTPEQWK SHRSYSCQVT HEGSTVEKTV APTECS                            216

SEQ ID NO: 4              moltype = AA   length = 121
FEATURE                   Location/Qualifiers
source                    1..121
                          mol_type = protein
                          organism = Homo sapiens
SEQUENCE: 4
QVQLVQSGAK VKKPGSSVKV SCKASGGTFS SYAISWVRQA PGQGLEWMGR IIPILGIANY    60
AQKFQGRVTI TADKSTSTAY MELSSLRSED TAVYYCARVV PGYSYGPFDY WGQGTTVTVS   120
S                                                                  121

SEQ ID NO: 5              moltype = AA   length = 214
FEATURE                   Location/Qualifiers
source                    1..214
                          mol_type = protein
                          organism = Homo sapiens
SEQUENCE: 5
SYVLTQPPSV SVTPGKTARI ACGGNNLESK IVSWYQQKPG QAPVLVIFYD TDRPSGISER    60
FSGSNSGNTA TLTISRVEAG DEADYYCQVW DSNSDHVIFG GGTKLTVLGQ PKAAPSVTLF   120
PPSSEELQAN KATLVCLISD FYPGAVTVAW KADSSPVKAG VETTTPSKQS NNKYAASSYL   180
SLTPEQWKSH RSYSCQVTHE GSTVEKTVAP TECS                              214

SEQ ID NO: 6              moltype = AA   length = 126
FEATURE                   Location/Qualifiers
source                    1..126
                          mol_type = protein
                          organism = Homo sapiens
SEQUENCE: 6
EVQLVESGGV VVQPGGSLRL SCAASGFTFD DYTMHWVRQA PGKGLEWVSL ISWDGGSTYY    60
ADSVKGRFTI SRDNSKNSLY LQMNSLRTED TALYYCASIY DPPPGSRSAL DAFDIWGQGT   120
MVTVSS                                                             126

SEQ ID NO: 7              moltype = AA   length = 214
FEATURE                   Location/Qualifiers
source                    1..214
                          mol_type = protein
                          organism = Homo sapiens
SEQUENCE: 7
SYVLTQPPSV SVTPGKTARI ACGGNNLESK IVSWYQQKPG QAPVLVIFYD TDRPSGISER    60
FSGSNSGNTA TLTISRVEAG DEADYYCQVW DSNSDHVIFG GGTKLTVLGQ PKAAPSVTLF   120
PPSSEELQAN KATLVCLISD FYPGAVTVAW KADSSPVKAG VETTTPSKQS NNKYAASSYL   180
SLTPEQWKSH RSYSCQVTHE GSTVEKTVAP AECS                              214

SEQ ID NO: 8              moltype = AA   length = 118
FEATURE                   Location/Qualifiers
source                    1..118
                          mol_type = protein
                          organism = Homo sapiens
SEQUENCE: 8
EVQLVESGGG LVKPGGSLRL SCAASGFTFS SYSMNWVRQA PGKGLEWVSS ISSSSRYIYY    60
ADSVKGRFTI SRDNAKNSLY LQMNSLRAED TAVYYCARQN EDVAFGIWGQ GTMVTVSS     118

SEQ ID NO: 9              moltype = AA   length = 327
FEATURE                   Location/Qualifiers
source                    1..327
                          mol_type = protein
                          organism = Homo sapiens
SEQUENCE: 9
ASTKGPSVFP LAPCSRSTSE STAALGCLVK DYFPEPVTVS WNSGALTSGV HTFPAVLQSS    60
GLYSLSSVVT VPSSSLGTKT YTCNVDHKPS NTKVDKRVES KYGPPCPPCP APEFLGGPSV   120
FLFPPKPKDT LMISRTPEVT CVVVDVSQED PEVQFNWYVD GVEVHNAKTK PREEQFNSTY   180
RVVSVLTVLH QDWLNGKEYK CKVSNKGLPS SIEKTISKAK GQPREPQVYT LPPSQEEMTK   240
NQVSLTCLVK GFYPSDIAVE WESNGQPENN YKTTPPVLDS DGSFFLYSRL TVDKSRWQEG   300
NVFSCSVMHE ALHNHYTQKS LSLSLGK                                      327

SEQ ID NO: 10             moltype = AA   length = 246
FEATURE                   Location/Qualifiers
```

```
REGION                      1..246
                            note = OX40 scFv (Clone A4)
source                      1..246
                            mol_type = protein
                            organism = synthetic construct
SEQUENCE: 10
QSALTQPPSA SGSPGQSVTI SCTGTSSDVG GYNYVSWYQQ HPGKAPKLMI YEVSQRPSGV    60
PDRFSGSKSG NTASLTVSGL QAEDEADYYC SSYAGSNNLG VFGGGTKLTV SSGGGGSGGG   120
GSGGGGSQVQ LVESGGGLVQ PGGSLRLSCA ASGFTFSSYE MNWVRQAPGK GLEWVSYISS   180
SGSTIYYADS VKGRFTISRD NAKNSLYLQM NSLRAEDTAV YYCARGGVGD AFDIWGQGTM   240
VTVSSA                                                              246

SEQ ID NO: 11               moltype = AA  length = 250
FEATURE                     Location/Qualifiers
REGION                      1..250
                            note = OX40 scFv (Clone B17)
source                      1..250
                            mol_type = protein
                            organism = synthetic construct
SEQUENCE: 11
YVLTQPPSVS VTPGKTARIA CGGNNLESKI VSWYQQKPGQ APVLVIFYDT DRPSGISERF    60
SGSNSGNTAT LTISRVEAGD EADYYCQVWD SNSDHVIFGG GTKLTVSSGG GGSGGGGSGG   120
GGSEVQLVES GGVVVQPGGS LRLSCAASGF TFDDYTMHWV RQAPGKGLEW VSLISWDGGS   180
TYYADSVKGR FTISRDNSKN SLYLQMNSLR TEDTALYYCA SIYDPPPGSR SALDAFDIWG   240
QGTMVTVSSA                                                          250

SEQ ID NO: 12               moltype = AA  length = 243
FEATURE                     Location/Qualifiers
REGION                      1..243
                            note = OX40 scFv (Clone B19)
source                      1..243
                            mol_type = protein
                            organism = synthetic construct
SEQUENCE: 12
SYVLTQPPSV SVTPGKTARI ACGGNNLESK IVSWYQQKPG QAPVLVIFYD TDRPSGISER    60
FSGSNSGNTA TLTISRVEAG DEADYYCQVW DSNSDHVIFG GGTKLTVSSG GGGSGGGGSG   120
GGGSEVQLVE SGGGLVKPGG SLRLSCAASG FTFSSYSMNW VRQAPGKGLE WVSSISSSSR   180
YIYYADSVKG RFTISRDNAK NSLYLQMNSL RAEDTAVYYC ARQNEDVAFG IWGQGTMVTV   240
SSA                                                                 243

SEQ ID NO: 13               moltype = AA  length = 241
FEATURE                     Location/Qualifiers
REGION                      1..241
                            note = OX40 scFv (Clone B120)
source                      1..241
                            mol_type = protein
                            organism = synthetic construct
SEQUENCE: 13
SYELTQPPSV SVSPGQTASI TCSGDTLGDK YASWYQQKPG RSPVLVIYQD SERPSGIPER    60
FSGSNSGNTA TLTISGTQAM DEADYYCQAW DSSTSYVFGT GTKVTVSSGG GGSGGGGSGG   120
GGSQVQLQQW GAGLLKPSET LSLTCAVYGG SFSGYYWSWI RQPPGKGLEW IGEINHSGST   180
NYNPSLKSRV TISVDTSKNQ FSLKLSSVTA ADTAVYYCAR GRWGGSFIYW GQGTLVTVSS   240
A                                                                   241

SEQ ID NO: 14               moltype = AA  length = 10
FEATURE                     Location/Qualifiers
REGION                      1..10
                            note = peptide linker
source                      1..10
                            mol_type = protein
                            organism = synthetic construct
SEQUENCE: 14
GGGGSGGGGS                                                           10

SEQ ID NO: 15               moltype = AA  length = 20
FEATURE                     Location/Qualifiers
REGION                      1..20
                            note = signal peptide
source                      1..20
                            mol_type = protein
                            organism = synthetic construct
SEQUENCE: 15
METDTLLLWV LLLWVPGSTG                                                20

SEQ ID NO: 16               moltype = AA  length = 704
FEATURE                     Location/Qualifiers
REGION                      1..704
                            note = Anti-PD-L1-clone 6 Heavy Chain-OX40 clone B17 scFv
                            antibody
```

```
source                  1..704
                        mol_type = protein
                        organism = synthetic construct
SEQUENCE: 16
QVQLVQSGAE VKKPGSSVKV SCKASGGTFR RYSISWVRQA PGQGLEWMGG IIPVFGAAKY   60
AQKFQGRVTI TADEFTSTAY MELSSLTSED TAVYYCALSG DSDAFDIWGQ GTMVTVSSAS  120
TKGPSVFPLA PCSRSTSEST AALGCLVKDY FPEPVTVSWN SGALTSGVHT FPAVLQSSGL  180
YSLSSVVTVP SSSLGTKTYT CNVDHKPSNT KVDKRVESKY GPPCPPCPAP EFLGGPSVFL  240
FPPKPKDTLM ISRTPEVTCV VVDVSQEDPE VQFNWYVDGV EVHNAKTKPR EEQFNSTYRV  300
VSVLTVLHQD WLNGKEYKCK VSNKGLPSSI EKTISKAKGQ PREPQVYTLP PSQEEMTKNQ  360
VSLTCLVKGF YPSDIAVEWE SNGQPENNYK TTPPVLDSDG SFFLYSRLTV DKSRWQEGNV  420
FSCSVMHEAL HNHYTQKSLS LSLGGGGSG GGGSYVLTQP PSVSVTPGKT ARIACGGNNL   480
ESKIVSWYQQ KPGQAPVLVI FYDTDRPSGI SERFSGSNSG NTATLTISRV EAGDEADYYC  540
QVWDSNSDHV IFGGGTKLTV SSGGGGSGGG GSGGGGSEVQ LVESGGVVVQ PGGSLRLSCA  600
ASGFTFDDYT MHWVRQAPGK GLEWVSLISW DGGSTYYADS VKGRFTISRD NSKNSLYLQM  660
NSLRTEDTAL YYCASIYDPP PGSRSALDAF DIWGQGTMVT VSSA              704

SEQ ID NO: 17           moltype = AA  length = 696
FEATURE                 Location/Qualifiers
REGION                  1..696
                        note = Anti-PD-L1-clone 6 Heavy Chain-OX40 clone B19 scFv
                         antibody
source                  1..696
                        mol_type = protein
                        organism = synthetic construct
SEQUENCE: 17
QVQLVQSGAE VKKPGSSVKV SCKASGGTFR RYSISWVRQA PGQGLEWMGG IIPVFGAAKY   60
AQKFQGRVTI TADEFTSTAY MELSSLTSED TAVYYCALSG DSDAFDIWGQ GTMVTVSSAS  120
TKGPSVFPLA PCSRSTSEST AALGCLVKDY FPEPVTVSWN SGALTSGVHT FPAVLQSSGL  180
YSLSSVVTVP SSSLGTKTYT CNVDHKPSNT KVDKRVESKY GPPCPPCPAP EFLGGPSVFL  240
FPPKPKDTLM ISRTPEVTCV VVDVSQEDPE VQFNWYVDGV EVHNAKTKPR EEQFNSTYRV  300
VSVLTVLHQD WLNGKEYKCK VSNKGLPSSI EKTISKAKGQ PREPQVYTLP PSQEEMTKNQ  360
VSLTCLVKGF YPSDIAVEWE SNGQPENNYK TTPPVLDSDG SFFLYSRLTV DKSRWQEGNV  420
FSCSVMHEAL HNHYTQKSLS LSLGGGGSG GGGSYVLTQP PSVSVTPGKT ARIACGGNNL   480
ESKIVSWYQQ KPGQAPVLVI FYDTDRPSGI SERFSGSNSG NTATLTISRV EAGDEADYYC  540
QVWDSNSDHV IFGGGTKLTV SSGGGGSGGG GSGGGGSEVQ LVESGGGLVK PGGSLRLSCA  600
ASGFTFSSYS MNWVRQAPGK GLEWVSSISS SSRYIYYADS VKGRFTISRD NAKNSLYLQM  660
NSLRAEDTAV YYCARQNEDV AFGIWGQGTM VTVSSA                        696

SEQ ID NO: 18           moltype = AA  length = 707
FEATURE                 Location/Qualifiers
REGION                  1..707
                        note = Anti-PD-L1-OX40 Ab-V1
source                  1..707
                        mol_type = protein
                        organism = synthetic construct
SEQUENCE: 18
QVQLVQSGAE VKKPGSSVKV SCKASGGTFR RYSISWVRQA PGQGLEWMGG IIPVFGAAKY   60
AQKFQGRVTI TADEFTSTAY MELSSLTSED TAVYYCALSG DSDAFDIWGQ GTMVTVSSAS  120
TKGPSVFPLA PCSRSTSEST AALGCLVKDY FPEPVTVSWN SGALTSGVHT FPAVLQSSGL  180
YSLSSVVTVP SSSLGTKTYT CNVDHKPSNT KVDKRVESKY GPPCPPCPAP EFLGGPSVFL  240
FPPKPKDTLM ISRTPEVTCV VVDVSQEDPE VQFNWYVDGV EVHNAKTKPR EEQFNSTYRV  300
VSVLTVLHQD WLNGKEYKCK VSNKGLPSSI EKTISKAKGQ PREPQVYTLP PSQEEMTKNQ  360
VSLTCLVKGF YPSDIAVEWE SNGQPENNYK TTPPVLDSDG SFFLYSRLTV DKSRWQEGNV  420
FSCSVMHEAL HNHYTQKSLS LSLGGGGSG GGGSYVLTQP PSVSVTPGKT ARIACGGNNL   480
ESKIVSWYQQ KPGQAPVLVI FYDTDRPSGI SERFSGSNSG NTATLTISRV EAGDEADYYC  540
QVWDSNSDHV IFGGGTKLTV LSSGGGGSGG GGGGSSRSSL QLVESGGV VVQPGGSLRL    600
SCAASGFTFD DYTMHWVRQA PGKGLEWVSL ISWDGGSTYY ADSVKGRFTI SRDNSKNSLY  660
LQMNSLRTED TALYYCASIY DPPPGSRSAL DAFDIWGQGT MVTVSSA             707

SEQ ID NO: 19           moltype = AA  length = 708
FEATURE                 Location/Qualifiers
REGION                  1..708
                        note = Anti-PD-L1-OX40 Ab-V2
source                  1..708
                        mol_type = protein
                        organism = synthetic construct
SEQUENCE: 19
QVQLVQSGAE VKKPGSSVKV SCKASGGTFR RYSISWVRQA PGQGLEWMGG IIPVFGAAKY   60
AQKFQGRVTI TADEFTSTAY MELSSLTSED TAVYYCALSG DSDAFDIWGQ GTMVTVSSAS  120
TKGPSVFPLA PCSRSTSEST AALGCLVKDY FPEPVTVSWN SGALTSGVHT FPAVLQSSGL  180
YSLSSVVTVP SSSLGTKTYT CNVDHKPSNT KVDKRVESKY GPPCPPCPAP EFLGGPSVFL  240
FPPKPKDTLM ISRTPEVTCV VVDVSQEDPE VQFNWYVDGV EVHNAKTKPR EEQFNSTYRV  300
VSVLTVLHQD WLNGKEYKCK VSNKGLPSSI EKTISKAKGQ PREPQVYTLP PSQEEMTKNQ  360
VSLTCLVKGF YPSDIAVEWE SNGQPENNYK TTPPVLDSDG SFFLYSRLTV DKSRWQEGNV  420
FSCSVMHEAL HNHYTQKSLS LSLGGGGSG GGGSYVLTQP PSVSVTPGKT ARIACGGNNL   480
ESKIVSWYQQ KPGQAPVLVI FYDTDRPSGI SERFSGSNSG NTATLTISRV EAGDEADYYC  540
QVWDSNSDHV IFGGGTKLTV LGGKGSGGKG TGGKGSGGKG SEVQLVESGG VVVQPGGSLR  600
```

```
LSCAASGFTF DDYTMHWVRQ APGKGLEWVS LISWDGGSTY YADSVKGRFT ISRDNSKNSL    660
YLQMNSLRTE DTALYYCASI YDPPPGSRSA LDAFDIWGQG TMVTVSSA                 708

SEQ ID NO: 20           moltype = AA  length = 701
FEATURE                 Location/Qualifiers
REGION                  1..701
                        note = Anti-PD-L1-OX40 Ab-V3
source                  1..701
                        mol_type = protein
                        organism = synthetic construct
SEQUENCE: 20
QVQLVQSGAE VKKPGSSVKV SCKASGGTFR RYSISWVRQA PGQGLEWMGG IIPVFGAAKY    60
AQKFQGRVTI TADEFTSTAY MELSSLTSED TAVYYCALSG DSDAFDIWGQ GTMVTVSSAS    120
TKGPSVFPLA PCSRSTSEST AALGCLVKDY FPEPVTVSWN SGALTSGVHT FPAVLQSSGL    180
YSLSSVVTVP SSSLGTKTYT CNVDHKPSNT KVDKRVESKY GPPCPPCPAP EFLGGPSVFL    240
FPPKPKDTLM ISRTPEVTCV VVDVSQEDPE VQFNWYVDGV EVHNAKTKPR EEQFNSTYRV    300
VSVLTVLHQD WLNGKEYKCK VSNKGLPSSI EKTISKAKGQ PREPQVYTLP PSQEEMTKNQ    360
VSLTCLVKGF YPSDIAVEWE SNGQPENNYK TTPPVLDSDG SFFLYSRLTV DKSRWQEGNV    420
FSCSVMHEAL HNHYTQKSLS LSLGGGGSG GGGSYVLTQP PSVSVTPGKT ARIACGNNL    480
ESKIVSWYQQ KPGQAPVLVI FYDTDRPSGI SERFSGSNSG NTATLTISRV EAGDEADYYC    540
QVWDSNSDHV IFGGGTKLTV LGSASAPTLF PLVSEVQLVE SGGVVVQPGG SLRLSCAASG    600
FTFDDYTMHW VRQAPGKGLE WVSLISWDGG STYYADSVKG RFTISRDNSK NSLYLQMNSL    660
RTEDTALYYC ASIYDPPPGS RSALDAFDIW GQGTMVTVSS A                       701

SEQ ID NO: 21           moltype = AA  length = 706
FEATURE                 Location/Qualifiers
REGION                  1..706
                        note = Anti-PD-L1-OX40 Ab-V4
source                  1..706
                        mol_type = protein
                        organism = synthetic construct
SEQUENCE: 21
QVQLVQSGAE VKKPGSSVKV SCKASGGTFR RYSISWVRQA PGQGLEWMGG IIPVFGAAKY    60
AQKFQGRVTI TADEFTSTAY MELSSLTSED TAVYYCALSG DSDAFDIWGQ GTMVTVSSAS    120
TKGPSVFPLA PCSRSTSEST AALGCLVKDY FPEPVTVSWN SGALTSGVHT FPAVLQSSGL    180
YSLSSVVTVP SSSLGTKTYT CNVDHKPSNT KVDKRVESKY GPPCPPCPAP EFLGGPSVFL    240
FPPKPKDTLM ISRTPEVTCV VVDVSQEDPE VQFNWYVDGV EVHNAKTKPR EEQFNSTYRV    300
VSVLTVLHQD WLNGKEYKCK VSNKGLPSSI EKTISKAKGQ PREPQVYTLP PSQEEMTKNQ    360
VSLTCLVKGF YPSDIAVEWE SNGQPENNYK TTPPVLDSDG SFFLYSRLTV DKSRWQEGNV    420
FSCSVMHEAL HNHYTQKSLS LSLGGGGSG GGGSYVLTQP PSVSVTPGKT ARIACGNNL    480
ESKIVSWYQQ KPGQAPVLVI FYDTDRPSGI SERFSGSNSG NTATLTISRV EAGDEADYYC    540
QVWDSNSDHV IFGGGTKLTV LGSTSGSGKP GSGEGSTKGE VQLVESGGVV VQPGGSLRLS    600
CAASGFTFDD YTMHWVRQAP GKGLEWVSLI SWDGGSTYYA DSVKGRFTIS RDNSKNSLYL    660
QMNSLRTEDT ALYYCASIYD PPPGSRSALD AFDIWGQGTM VTVSSA                  706

SEQ ID NO: 22           moltype = AA  length = 706
FEATURE                 Location/Qualifiers
REGION                  1..706
                        note = Anti-PD-L1-OX40 Ab-V5
source                  1..706
                        mol_type = protein
                        organism = synthetic construct
SEQUENCE: 22
QVQLVQSGAE VKKPGSSVKV SCKASGGTFR RYSISWVRQA PGQGLEWMGG IIPVFGAAKY    60
AQKFQGRVTI TADEFTSTAY MELSSLTSED TAVYYCALSG DSDAFDIWGQ GTMVTVSSAS    120
TKGPSVFPLA PCSRSTSEST AALGCLVKDY FPEPVTVSWN SGALTSGVHT FPAVLQSSGL    180
YSLSSVVTVP SSSLGTKTYT CNVDHKPSNT KVDKRVESKY GPPCPPCPAP EFLGGPSVFL    240
FPPKPKDTLM ISRTPEVTCV VVDVSQEDPE VQFNWYVDGV EVHNAKTKPR EEQFNSTYRV    300
VSVLTVLHQD WLNGKEYKCK VSNKGLPSSI EKTISKAKGQ PREPQVYTLP PSQEEMTKNQ    360
VSLTCLVKGF YPSDIAVEWE SNGQPENNYK TTPPVLDSDG SFFLYSRLTV DKSRWQEGNV    420
FSCSVMHEAL HNHYTQKSLS LSLGGGGSG GGGSYELTQP PSVSVTPGQT ARIACGNNL    480
ESKIVSWYQQ KPGQAPVLVI FYDTDRPSGI SERFSGSNSG NTATLTISRV EAGDEADYYC    540
QVWDSNSDHV IFGGGTKLTV LGSTSGSGKP GSGEGSTKGE VQLVESGGVV VQPGGSLRLS    600
CAASGFTFDD YTMHWVRQAP GKGLEWVSLI SWDGGSTYYA DSVKGRFTIS RDNSKNSLYL    660
QMNSLRTEDT ALYYCASIYD PPPGSRSALD AFDIWGQGTM VTVSSA                  706

SEQ ID NO: 23           moltype = AA  length = 706
FEATURE                 Location/Qualifiers
REGION                  1..706
                        note = Anti-PD-L1-OX40 Ab-V6
source                  1..706
                        mol_type = protein
                        organism = synthetic construct
SEQUENCE: 23
QVQLVQSGAE VKKPGSSVKV SCKASGGTFR RYSISWVRQA PGQGLEWMGG IIPVFGAAKY    60
AQKFQGRVTI TADEFTSTAY MELSSLTSED TAVYYCALSG DSDAFDIWGQ GTMVTVSSAS    120
TKGPSVFPLA PCSRSTSEST AALGCLVKDY FPEPVTVSWN SGALTSGVHT FPAVLQSSGL    180
YSLSSVVTVP SSSLGTKTYT CNVDHKPSNT KVDKRVESKY GPPCPPCPAP EFLGGPSVFL    240
FPPKPKDTLM ISRTPEVTCV VVDVSQEDPE VQFNWYVDGV EVHNAKTKPR EEQFNSTYRV    300
```

```
VSVLTVLHQD WLNGKEYKCK VSNKGLPSSI EKTISKAKGQ PREPQVYTLP PSQEEMTKNQ    360
VSLTCLVKGF YPSDIAVEWE SNGQPENNYK TTPPVLDSDG SFFLYSRLTV DKSRWQEGNV    420
FSCSVMHEAL HNHYTQKSLS LSLGGGGSG  GGGSYVLTQP PSVSVTPGET ARIACGGNNL    480
ESKIVSWYQQ KPGQAPVLVI FYDTDRPSGI SERFSGSNSG NTATLTISRV EAGDEADYYC    540
QVWDSNSDHV VFGGGTKLTV LGSTSGSGKP GSGEGSTKGE VQLVESGGGV VQPGGSLRLS    600
CAASGFTFDD YTMHWVRQAP GKGLEWVSLI SWDGGSTYYA DSVKGRFTIS RDNSKNSLYL    660
QMNSLRTEDT ALYYCASIYD PPPGSRSALD AFDIWGQGTM VTVSSA                  706

SEQ ID NO: 24             moltype = AA   length = 706
FEATURE                   Location/Qualifiers
REGION                    1..706
                          note = Anti-PD-L1-OX40 Ab-V7
source                    1..706
                          mol_type = protein
                          organism = synthetic construct
SEQUENCE: 24
QVQLVQSGAE VKKPGSSVKV SCKASGGTFR RYSISWVRQA PGQGLEWMGG IIPVFGAAKY     60
AQKFQGRVTI TADEFTSTAY MELSSLTSED TAVYYCALSG DSDAFDIWGQ GTMVTVSSAS    120
TKGPSVFPLA PCSRSTSEST AALGCLVKDY FPEPVTVSWN SGALTSGVHT FPAVLQSSGL    180
YSLSSVVTVP SSSLGTKTYT CNVDHKPSNT KVDKRVESKY GPPCPPCPAP EFLGGPSVFL    240
FPPKPKDTLM ISRTPEVTCV VVDVSQEDPE VQFNWYVDGV EVHNAKTKPR EEQFNSTYRV    300
VSVLTVLHQD WLNGKEYKCK VSNKGLPSSI EKTISKAKGQ PREPQVYTLP PSQEEMTKNQ    360
VSLTCLVKGF YPSDIAVEWE SNGQPENNYK TTPPVLDSDG SFFLYSRLTV DKSRWQEGNV    420
FSCSVMHEAL HNHYTQKSLS LSLGGGGSG  GGGSYVLTQP PSVSVTPGQT ARIACGGNNL    480
ESKIVSWYQQ KPGQAPVLVI FYDTDRPSGI SERFSGSNSG NTATLTISRV EAGDEADYYC    540
QVWDSNSDHV VFGGGTKLTV LGSTSGSGKP GSGEGSTKGE VQLVESGGGV VQPGGSLRLS    600
CAASGFTFDD YTMHWVRQAP GKGLEWVSLI SWDGGSTYYA DSVKGRFTIS RDNSKNSLYL    660
QMNSLRTEDT ALYYCASIYD PPPGSRSALD AFDIWGQGTM VTVSSA                  706

SEQ ID NO: 25             moltype = AA   length = 706
FEATURE                   Location/Qualifiers
REGION                    1..706
                          note = Anti-PD-L1-OX40 Ab-V8
source                    1..706
                          mol_type = protein
                          organism = synthetic construct
SEQUENCE: 25
QVQLVQSGAE VKKPGSSVKV SCKASGGTFR RYSISWVRQA PGQGLEWMGG IIPVFGAAKY     60
AQKFQGRVTI TADEFTSTAY MELSSLTSED TAVYYCALSG DSDAFDIWGQ GTMVTVSSAS    120
TKGPSVFPLA PCSRSTSEST AALGCLVKDY FPEPVTVSWN SGALTSGVHT FPAVLQSSGL    180
YSLSSVVTVP SSSLGTKTYT CNVDHKPSNT KVDKRVESKY GPPCPPCPAP EFLGGPSVFL    240
FPPKPKDTLM ISRTPEVTCV VVDVSQEDPE VQFNWYVDGV EVHNAKTKPR EEQFNSTYRV    300
VSVLTVLHQD WLNGKEYKCK VSNKGLPSSI EKTISKAKGQ PREPQVYTLP PSQEEMTKNQ    360
VSLTCLVKGF YPSDIAVEWE SNGQPENNYK TTPPVLDSDG SFFLYSRLTV DKSRWQEGNV    420
FSCSVMHEAL HNHYTQKSLS LSLGGGGSG  GGGSYVLTQP PSVSVAPGKT ARITCGGNNL    480
ESKIVSWYQQ KPGQAPVLVI FYDTDRPSGI PERFSGSNSG NTATLTISRV EAGDEADYYC    540
QVWDSNSDHV IFGGGTKLTV LGSTSGSGKP GSGEGSTKGE VQLVESGGIV VQPGGSLRLS    600
CAASGFTFDD YTMHWVRQAP GKGLEWVSLI SWDGGSTYYA DSVKGRFTIS RDNSKNSLYL    660
QMNSLRTEDT ALYYCASIYD PPPGSRSALD AFDIWGQGTM VTVSSA                  706

SEQ ID NO: 26             moltype = AA   length = 706
FEATURE                   Location/Qualifiers
REGION                    1..706
                          note = Anti-PD-L1-OX40 Ab-V9
source                    1..706
                          mol_type = protein
                          organism = synthetic construct
SEQUENCE: 26
QVQLVQSGAE VKKPGSSVKV SCKASGGTFR RYSISWVRQA PGQGLEWMGG IIPVFGAAKY     60
AQKFQGRVTI TADEFTSTAY MELSSLTSED TAVYYCALSG DSDAFDIWGQ GTMVTVSSAS    120
TKGPSVFPLA PCSRSTSEST AALGCLVKDY FPEPVTVSWN SGALTSGVHT FPAVLQSSGL    180
YSLSSVVTVP SSSLGTKTYT CNVDHKPSNT KVDKRVESKY GPPCPPCPAP EFLGGPSVFL    240
FPPKPKDTLM ISRTPEVTCV VVDVSQEDPE VQFNWYVDGV EVHNAKTKPR EEQFNSTYRV    300
VSVLTVLHQD WLNGKEYKCK VSNKGLPSSI EKTISKAKGQ PREPQVYTLP PSQEEMTKNQ    360
VSLTCLVKGF YPSDIAVEWE SNGQPENNYK TTPPVLDSDG SFFLYSRLTV DKSRWQEGNV    420
FSCSVMHEAL HNHYTQKSLS LSLGGGGSG  GGGSYVLTQP PSVSVAPGKT ARITCGGNNL    480
ESKIVSWYQQ KPGQAPVLVI FYDTDRPSGI PERFSGSNSG NTATLTISRV EAGDEADYYC    540
QVWDSNSDHV VFGGGTKLTV LGSTSGSGKP GSGEGSTKGE VQLVESGGGV VQPGGSLRLS    600
CAASGFTFDD YTMHWVRQAP GKGLEWVSLI SWDGGSTYYA DSVKGRFTIS RDNSKNSLYL    660
QMNSLRTEDT ALYYCASIYD PPPGSRSALD AFDIWGQGTM VTVSSA                  706

SEQ ID NO: 27             moltype = AA   length = 706
FEATURE                   Location/Qualifiers
REGION                    1..706
                          note = Anti-PD-L1-OX40 Ab-V10
source                    1..706
                          mol_type = protein
                          organism = synthetic construct
```

-continued

```
SEQUENCE: 27
QVQLVQSGAE VKKPGSSVKV SCKASGGTFR RYSISWVRQA PGQGLEWMGG IIPVFGAAKY    60
AQKFQGRVTI TADEFTSTAY MELSSLTSED TAVYYCALSG DSDAFDIWGQ GTMVTVSSAS   120
TKGPSVFPLA PCSRSTSEST AALGCLVKDY FPEPVTVSWN SGALTSGVHT FPAVLQSSGL   180
YSLSSVVTVP SSSLGTKTYT CNVDHKPSNT KVDKRVESKY GPPCPPCPAP EFLGGPSVFL   240
FPPKPKDTLM ISRTPEVTCV VVDVSQEDPE VQFNWYVDGV EVHNAKTKPR EEQFNSTYRV   300
VSVLTVLHQD WLNGKEYKCK VSNKGLPSSI EKTISKAKGQ PREPQVYTLP PSQEEMTKNQ   360
VSLTCLVKGF YPSDIAVEWE SNGQPENNYK TTPPVLDSDG SFFLYSRLTV DKSRWQEGNV   420
FSCSVMHEAL HNHYTQKSLS LSLGGGGSG GGGSYVLTQP PSVSVAPGQT ARITCGGNNL   480
ESKIVSWYQQ KPGQAPVLVI FYDTDRPSGI PERFSGSNSG NTATLTISRV EAGDEADYYC   540
QVWDSNSDHV VFGGGTKLTV LGSTSGSGKP GSGEGSTKGE VQLVESGGGV VQPGGSLRLS   600
CAASGFTFDD YTMHWVRQAP GKGLEWVSLI SWDGGSTYYA DSVKGRFTIS RDNSKNSLYL   660
QMNSLRTEDT ALYYCASIYD PPPGSRSALD AFDIWGQGTM VTVSSA                 706

SEQ ID NO: 28        moltype = AA  length = 706
FEATURE              Location/Qualifiers
REGION               1..706
                     note = Anti-PD-L1-OX40 Ab-V11
source               1..706
                     mol_type = protein
                     organism = synthetic construct
SEQUENCE: 28
QVQLVQSGAE VKKPGSSVKV SCKASGGTFR RYSISWVRQA PGQGLEWMGG IIPVFGAAKY    60
AQKFQGRVTI TADEFTSTAY MELSSLTSED TAVYYCALSG DSDAFDIWGQ GTMVTVSSAS   120
TKGPSVFPLA PCSRSTSEST AALGCLVKDY FPEPVTVSWN SGALTSGVHT FPAVLQSSGL   180
YSLSSVVTVP SSSLGTKTYT CNVDHKPSNT KVDKRVESKY GPPCPPCPAP EFLGGPSVFL   240
FPPKPKDTLM ISRTPEVTCV VVDVSQEDPE VQFNWYVDGV EVHNAKTKPR EEQFNSTYRV   300
VSVLTVLHQD WLNGKEYKCK VSNKGLPSSI EKTISKAKGQ PREPQVYTLP PSQEEMTKNQ   360
VSLTCLVKGF YPSDIAVEWE SNGQPENNYK TTPPVLDSDG SFFLYSRLTV DKSRWQEGNV   420
FSCSVMHEAL HNHYTQKSLS LSLGGGGSG GGGSYVLTQP PSVSVTPGET ARIACGGNNL   480
ESKIVSWYQQ KPGQAPVLVI FYDTDRPSGI SERFSGSNSG NTATLTISRV EAGDEADYYC   540
QVWDSNSDHV IFGGGTKLTV LGSTSGSGKP GSGEGSTKGE VQLVESGGGV VQPGGSLRLS   600
CAASGFTFDD YTMHWVRQAP GKGLEWVSLI SWDGGSTYYA DSVKGRFTIS RDNSKNSLYL   660
QMNSLRTEDT ALYYCASIYD PPPGSRSALD AFDIWGQGTM VTVSSA                 706

SEQ ID NO: 29        moltype = AA  length = 706
FEATURE              Location/Qualifiers
REGION               1..706
                     note = Anti-PD-L1-OX40 Ab-V12
source               1..706
                     mol_type = protein
                     organism = synthetic construct
SEQUENCE: 29
QVQLVQSGAE VKKPGSSVKV SCKASGGTFR RYSISWVRQA PGQGLEWMGG IIPVFGAAKY    60
AQKFQGRVTI TADEFTSTAY MELSSLTSED TAVYYCALSG DSDAFDIWGQ GTMVTVSSAS   120
TKGPSVFPLA PCSRSTSEST AALGCLVKDY FPEPVTVSWN SGALTSGVHT FPAVLQSSGL   180
YSLSSVVTVP SSSLGTKTYT CNVDHKPSNT KVDKRVESKY GPPCPPCPAP EFLGGPSVFL   240
FPPKPKDTLM ISRTPEVTCV VVDVSQEDPE VQFNWYVDGV EVHNAKTKPR EEQFNSTYRV   300
VSVLTVLHQD WLNGKEYKCK VSNKGLPSSI EKTISKAKGQ PREPQVYTLP PSQEEMTKNQ   360
VSLTCLVKGF YPSDIAVEWE SNGQPENNYK TTPPVLDSDG SFFLYSRLTV DKSRWQEGNV   420
FSCSVMHEAL HNHYTQKSLS LSLGGGGSG GGGSYVLTQP PSVSVTPGKT ARIACGGNNL   480
ESKIVSWYQQ KPGQAPVLVI FYDTDRPSGI SERFSGSNSG NTATLTISRV EAGDEADYYC   540
QVWDSNSDHV IFGGGTKLTV LGSTSGSGKP GSGEGSTKGE VQLVESGGGV VQPGGSLRLS   600
CAASGFTFDD YTMHWVRQAP GKGLEWVSLI SWDGGSTYYA DSVKGRFTIS RDNSKNSLYL   660
QMNSLRTEDT ALYYCASIYD PPPGSRSALD AFDIWGQGTM VTVSSA                 706

SEQ ID NO: 30        moltype = AA  length = 176
FEATURE              Location/Qualifiers
REGION               1..176
                     note = Anti-PD-L1-OX40 Ab-V4
source               1..176
                     mol_type = protein
                     organism = synthetic construct
SEQUENCE: 30
LSLGGGGSG GGGSYVLTQP PSVSVTPGKT ARIACGGNNL ESKIVSWYQQ KPGQAPVLVI    60
FYDTDRPSGI SERFSGSNSG NTATLTISRV EAGDEADYYC QVWDSNSDHV IFGGGTKLTV   120
LGSTSGSGKP GSGEGSTKGE VQLVESGGGV VQPGGSLRLS CAASGFTFDD YTMHWV      176

SEQ ID NO: 31        moltype = AA  length = 176
FEATURE              Location/Qualifiers
REGION               1..176
                     note = Anti-PD-L1-OX40 Ab-V5
source               1..176
                     mol_type = protein
                     organism = synthetic construct
SEQUENCE: 31
LSLGGGGSG GGGSYELTQP PSVSVTPGQT ARIACGGNNL ESKIVSWYQQ KPGQAPVLVI    60
FYDTDRPSGI SERFSGSNSG NTATLTISRV EAGDEADYYC QVWDSNSDHV IFGGGTKLTV   120
LGSTSGSGKP GSGEGSTKGE VQLVESGGGV VQPGGSLRLS CAASGFTFDD YTMHWV      176
```

```
SEQ ID NO: 32            moltype = AA   length = 176
FEATURE                  Location/Qualifiers
REGION                   1..176
                         note = Anti-PD-L1-OX40 Ab-V6
source                   1..176
                         mol_type = protein
                         organism = synthetic construct
SEQUENCE: 32
LSLGGGGSG GGGSYVLTQP PSVSVTPGET ARIACGGNNL ESKIVSWYQQ KPGQAPVLVI   60
FYDTDRPSGI SERFSGSNSG NTATLTISRV EAGDEADYYC QVWDSNSDHV VFGGGTKLTV  120
LGSTSGSGKP GSGEGSTKGE VQLVESGGGV VQPGGSLRLS CAASGFTFDD YTMHWV      176

SEQ ID NO: 33            moltype = AA   length = 176
FEATURE                  Location/Qualifiers
REGION                   1..176
                         note = Anti-PD-L1-OX40 Ab-V7
source                   1..176
                         mol_type = protein
                         organism = synthetic construct
SEQUENCE: 33
LSLGGGGSG GGGSYVLTQP PSVSVTPGQT ARIACGGNNL ESKIVSWYQQ KPGQAPVLVI   60
FYDTDRPSGI SERFSGSNSG NTATLTISRV EAGDEADYYC QVWDSNSDHV VFGGGTKLTV  120
LGSTSGSGKP GSGEGSTKGE VQLVESGGGV VQPGGSLRLS CAASGFTFDD YTMHWV      176

SEQ ID NO: 34            moltype = AA   length = 176
FEATURE                  Location/Qualifiers
REGION                   1..176
                         note = Anti-PD-L1-OX40 Ab-V8
source                   1..176
                         mol_type = protein
                         organism = synthetic construct
SEQUENCE: 34
LSLGGGGSG GGGSYVLTQP PSVSVAPGKT ARITCGGNNL ESKIVSWYQQ KPGQAPVLVI   60
FYDTDRPSGI PERFSGSNSG NTATLTISRV EAGDEADYYC QVWDSNSDHV IFGGGTKLTV  120
LGSTSGSGKP GSGEGSTKGE VQLVESGGIV VQPGGSLRLS CAASGFTFDD YTMHWV      176

SEQ ID NO: 35            moltype = AA   length = 176
FEATURE                  Location/Qualifiers
REGION                   1..176
                         note = Anti-PD-L1-OX40 Ab-V9
source                   1..176
                         mol_type = protein
                         organism = synthetic construct
SEQUENCE: 35
LSLGGGGSG GGGSYVLTQP PSVSVAPGKT ARITCGGNNL ESKIVSWYQQ KPGQAPVLVI   60
FYDTDRPSGI PERFSGSNSG NTATLTISRV EAGDEADYYC QVWDSNSDHV VFGGGTKLTV  120
LGSTSGSGKP GSGEGSTKGE VQLVESGGGV VQPGGSLRLS CAASGFTFDD YTMHWV      176

SEQ ID NO: 36            moltype = AA   length = 176
FEATURE                  Location/Qualifiers
REGION                   1..176
                         note = Anti-PD-L1-OX40 Ab-V10
source                   1..176
                         mol_type = protein
                         organism = synthetic construct
SEQUENCE: 36
LSLGGGGSG GGGSYVLTQP PSVSVAPGQT ARITCGGNNL ESKIVSWYQQ KPGQAPVLVI   60
FYDTDRPSGI PERFSGSNSG NTATLTISRV EAGDEADYYC QVWDSNSDHV VFGGGTKLTV  120
LGSTSGSGKP GSGEGSTKGE VQLVESGGGV VQPGGSLRLS CAASGFTFDD YTMHWV      176

SEQ ID NO: 37            moltype = AA   length = 176
FEATURE                  Location/Qualifiers
REGION                   1..176
                         note = Anti-PD-L1-OX40 Ab-V11
source                   1..176
                         mol_type = protein
                         organism = synthetic construct
SEQUENCE: 37
LSLGGGGSG GGGSYVLTQP PSVSVTPGET ARIACGGNNL ESKIVSWYQQ KPGQAPVLVI   60
FYDTDRPSGI SERFSGSNSG NTATLTISRV EAGDEADYYC QVWDSNSDHV IFGGGTKLTV  120
LGSTSGSGKP GSGEGSTKGE VQLVESGGVV VQPGGSLRLS CAASGFTFDD YTMHWV      176

SEQ ID NO: 38            moltype = AA   length = 176
FEATURE                  Location/Qualifiers
REGION                   1..176
                         note = Anti-PD-L1-OX40 Ab-V12
```

```
source                  1..176
                        mol_type = protein
                        organism = synthetic construct
SEQUENCE: 38
LSLGGGGGSG GGGSYVLTQP PSVSVTPGQT ARIACGGNNL ESKIVSWYQQ KPGQAPVLVI    60
FYDTDRPSGI SERFSGSNSG NTATLTISRV EAGDEADYYC QVWDSNSDHV IFGGGTKLTV   120
LGSTSGSGKP GSGEGSTKGE VQLVESGGVV VQPGGSLRLS CAASGFTFDD YTMHWV       176

SEQ ID NO: 39           moltype = AA   length = 15
FEATURE                 Location/Qualifiers
REGION                  1..15
                        note = linker
source                  1..15
                        mol_type = protein
                        organism = synthetic construct
SEQUENCE: 39
GGGGSGGGGS GGGGS                                                     15

SEQ ID NO: 40           moltype = AA   length = 19
FEATURE                 Location/Qualifiers
REGION                  1..19
                        note = linker
source                  1..19
                        mol_type = protein
                        organism = synthetic construct
SEQUENCE: 40
SSGGGGSGGG GGGSSRSSL                                                 19

SEQ ID NO: 41           moltype = AA   length = 20
FEATURE                 Location/Qualifiers
REGION                  1..20
                        note = linker
source                  1..20
                        mol_type = protein
                        organism = synthetic construct
SEQUENCE: 41
GGKGSGGKGT GGKGSGGKGS                                                20

SEQ ID NO: 42           moltype = AA   length = 13
FEATURE                 Location/Qualifiers
REGION                  1..13
                        note = linker
source                  1..13
                        mol_type = protein
                        organism = synthetic construct
SEQUENCE: 42
GSASAPTLFP LVS                                                       13

SEQ ID NO: 43           moltype = AA   length = 18
FEATURE                 Location/Qualifiers
REGION                  1..18
                        note = linker
source                  1..18
                        mol_type = protein
                        organism = synthetic construct
SEQUENCE: 43
GSTSGSGKPG SGEGSTKG                                                  18
```

PD-L1 AND OX40 BINDING PROTEINS FOR CANCER REGULATION

CROSS-REFERENCE TO RELATED APPLICATION

This application is a continuation application of U.S. application Ser. No. 16/871,799, filed on May 11, 2020, which is a continuation of International Application No. PCT/US2018/067868, filed on Dec. 28, 2018, which claims the benefits of priority of U.S. Provisional Application No. 62/611,543, filed Dec. 29, 2017, the disclosures of which are incorporated herein by reference in their entireties.

The Sequence Listing associated with this application is filed in electronic format via EFS-Web and is hereby incorporated by reference into the specification in its entirety. The name of the XML file containing the Sequence Listing is NP-24083-1-US_SEQ_LIST.xml. The size of the XML file is 65,027 bytes, and the XML file was created on Mar. 8, 2023.

BACKGROUND

Field of Invention

The present invention relates to an antibody. More particularly, the present invention relates to the antibody for cancer therapy.

Description of Related Art

The two major types of lymphocytes in humans are T (thymus-derived) and B (bone marrow derived. These cells are derived from hematopoietic stem cells in the bone marrow and fetal liver that have committed to the lymphoid development pathway. The progeny of these stem cells follow divergent pathways to mature into either B or T lymphocytes. Human B-lymphocyte development takes place entirely within the bone marrow. T cells, on the other hand, develop from immature precursors that leave the marrow and travel through the bloodstream to the thymus, where they proliferate and differentiate into mature T lymphocytes.

T Cells

T-cells are the most abundant (about 75% of blood lymphocytes) and potent immune killer cells. The role of effector T-cells in the anti-tumor immune response is strongly supported by in vitro studies and the observation that a high infiltration of CD8+ T cells in several types of tumors correlates with a favorable clinical prognostic (Fridman et al., 2012). The activation of effector naive T-cells requires at least three complementary signals: (i) TCR-CD3/Ag-MHC interaction with the assistance of co-receptors (CD4 or CD8); (ii) binding of co-stimulatory molecules such as CD80 or CD86 to CD28, CD40/CD40L; and (iii) accessory molecules such as cytokines.

Co-stimulation or the provision of two distinct signals to T-cells is a widely accepted model of lymphocyte activation of resting T lymphocytes by antigen-presenting cells (APCs) (Lafferty and Cunningham, 1975). This model further provides for the discrimination of self from non-self and immune tolerance (Bretscher and Cohn, 1970; Bretscher, 1999; Jenkins and Schwartz, 1987). The primary signal, or antigen specific signal, is transduced through the T-cell receptor (TCR) following recognition of foreign antigen peptide presented in the context of the major histocompatibility-complex (MHC). The second or co-stimulatory signal is delivered to T-cells by co-stimulatory molecules expressed on antigen-presenting cells (APCs), and induce T-cells to promote clonal expansion, cytokine secretion and effector function (Lenschow et al., 1996). In the absence of costimulation, T-cells can become refractory to antigen stimulation, do not mount an effective immune response, and further may result in exhaustion or tolerance to foreign antigens.

Immune Checkpoint Protein: PD-L1 and OX40

Immune checkpoints refer to a group of inhibitory and stimulatory pathways mostly initiated by ligand-receptor interaction hardwiring the immune system, specifically T-cell mediated immunity, to maintain self-tolerance and modulate the duration and amplitude of physiological responses in peripheral tissues in order to minimize collateral tissue damages normally (Pardoll, 2012). Tumor cells co-opt certain checkpoint pathways as a major mechanism of immune resistance. For example, programmed cell death protein 1 ligand, PD-L1, is commonly up-regulated on tumor cell surface of human cancers. The interaction of PD-L1 with its receptor, PD-1, expressed on tumor infiltrated lymphocytes (TILs), specifically on T cells, inhibits local T cell-mediated response to escape the immune surveillance (Liang et al., 2006; Sznol and Chen, 2013). Thus, the inhibition of immunosuppressive signals on cancer cells, or direct agonistic stimulation of T cells, results in and/or induces a strong sustained anti-tumor immune response. Recent clinical studies strongly suggested blockage of immune checkpoint proteins via antibody or modulated by soluble ligands or receptors are the most promising approaches to activating therapeutic antitumor immunity (Topalian et al., 2014). Currently, anti-PD-1 and anti-CTLA-4 (cytotoxic T-lymphocyte-associated antigen-4) antibodies have been approved by FDA to treat diseases such as melanomas.

Another co-stimulator molecule is the OX40 receptor (CD134), a member of the TNFR superfamily, which is membrane-bound and is expressed primarily on activated CD4+ T cells (Paterson et al., 1987). Signaling through the OX40 receptor (hereinafter "OX40") is costimulatory to effector T cells and causes proliferation of T-cells (Watts, 2005; Weinberg et al., 1994). Studies of OX40 suggest that its major role is to dictate the number of effector T-cells that accumulate in primary immune responses, and consequently to govern the number of memory T-cells that subsequently develop and survive (Croft, 2003). A number in vitro studies have been shown that OX40 provides a costimulatory signal resulting, in enhanced T cell proliferation and cytokine production.

Bi-Specific/Bi-Functional Antibody

The idea of using bispecific antibodies to efficiently retarget effector immune cells toward tumor cells emerged in the 1980s (Karpovsky et al., 1984; Perez et al., 1985; Staerz et al., 1985). Bispecific scaffolds are generally classified in two major groups with different pharmacokinetic properties, based on the absence or presence of an Fc fragment, IgG-like molecules and small recombinant bispecific formats, most of them deriving from single chain variable fragment (scFv). Through their compact size, antibody fragments usually penetrate tumors more efficiently than IgG-like molecules but this benefit is mitigated by a short serum half-life (few hours) limiting their overall tumor uptake and residence time (Goldenberg et al., 2007). By contrast, the presence of an Fc fragment, which binds to the neonatal Fc receptors, provides a long serum half-life (>10 days) to the IgG-like formats, favoring tumor uptake and retention, but limits tumor penetration.

Recent studies have highlighted the therapeutic efficacy of immunotherapy, a class of cancer treatments that utilize the patient's own immune system to destroy cancerous cells. Within a tumor the presence of a family of negative regulatory molecules, collectively known as "checkpoint inhibitors," can inhibit T cell function to suppress anti-tumor immunity. Checkpoint inhibitors, such as CTLA-4 and PD-1, attenuate T cell proliferation and cytokine production. Targeted blockade of CTLA-4 or PD-1 with antagonist monoclonal antibodies (mAbs) releases the "brakes" on T cells to boost anti-tumor immunity. Generating optimal "killer" CD8 T cell responses also requires T cell receptor activation plus co-stimulation, which can be provided through ligation of tumor necrosis factor receptor family members, including OX40 (CD134) and 4-1BB (CD137). OX40 is of particular interest as treatment with an activating (agonist) anti-OX40 mAb augments T cell differentiation and cytolytic function leading to enhanced anti-tumor immunity against a variety of tumors. When used as single agents, these drugs can induce potent clinical and immunologic responses in patients with metastatic disease (Linch et al., 2015).

SUMMARY

The present disclosure designed to investigate the bispecific antibody with immunomodulatory aiming for the treatment of patient with cancers, such as prostate cancer, lung cancer, NSCLC, melanoma, lymphoma, breast cancer, head and neck cancer, RCC, or ovarian cancer were examined.

The present disclosure provides an antibody or an antigen-binding portion thereof binding to OX40 (CD134), comprising: a heavy chain variable region comprising an amino acid sequence of at least about 80% sequence homology to the amino acid sequence selected from the group consisting of SEQ ID NO: 6, SEQ ID NO: 8, amino acid 128-246 of SEQ ID NO: 10, and amino acid 124-241 SEQ ID NO: 13; and a light chain variable region comprising an amino acid sequence of at least about 80% homology to the amino acid sequence selected from the group consisting of amino acid 1-108 of SEQ ID NO: 5, 1-108 of SEQ ID NO: 7, 1-112 of SEQ ID NO: 10, and 1-108 of SEQ ID NO: 13.

In one embodiment, the antibody or the antigen-binding portion thereof is a single chain variable fragment (scFv) sequence selected from the group consisting of SEQ ID NOs: 10, 11, 12, and 13.

In one embodiment, the antibody or the antigen-binding portion thereof is a bispecific antibody.

In one embodiment, the bispecific antibody comprises an immune checkpoint protein binding site.

In one embodiment, the immune checkpoint protein binding site comprises a programmed cell death protein 1 ligand (PD-L1) binding site, PD-1 binding site, epidermal growth factor receptor (EGFR) binding site, human epidermal growth factor receptor 2 (HER2) binding site, cytotoxic T-lymphocyte-associated antigen 4 (CTLA-4) binding site, or lymphocyte activation gene 3 (LAG3) binding site.

The present disclosure also provides an antibody or an antigen-binding portion thereof binding to PD-L1, comprising: a heavy chain variable domain comprising an amino acid sequence of at least about 80% sequence homology to the amino acid sequence selected from the group consisting of SEQ ID NO: 2 and SEQ ID NO: 4; and a light chain variable domain comprising an amino acid sequence of at least about 80% homology to the amino acid sequence selected from the group consisting of amino acid 1-111 of SEQ ID NO: 1 and 1-110 of SEQ ID NO: 3.

The present disclosure also provides a bispecific antibody comprising at least one of polypeptide chain, wherein the polypeptide chain comprises an OX40 binding site and a PD-L1 binding site. The OX40 binding site comprises a heavy chain variable region comprising an amino acid sequence of at least about 80% sequence homology to the amino acid sequence selected from the group consisting of SEQ ID NO: 6, SEQ ID NO: 8, amino acid 128-246 of SEQ ID NO: 10, and amino acid 124-241 SEQ ID NO: 13; and a light chain variable region comprising an amino acid sequence of at least about 80% homology to the amino acid sequence selected from the group consisting of amino acid 1-108 of SEQ ID NO: 5, 1-108 of SEQ ID NO: 7, 1-112 of SEQ ID NO: 10 and 1-108 of SEQ ID NO: 13. The PD-L1 binding site comprises a heavy chain variable domain comprising an amino acid sequence of at least about 80% sequence homology to the amino acid sequence selected from the group consisting of SEQ ID NO: 2 and SEQ ID NO: 4; and a light chain variable domain comprising an amino acid sequence of at least about 80% homology to the amino acid sequence selected from the group consisting of amino acid 1-111 of SEQ ID NO: 1 and 1-110 of SEQ ID NO: 3.

In one embodiment, the polypeptide chain further comprises a Fc domain, a Fab fragment, and a scFv. The Fab fragment is connected to the N-terminus of the Fc domain, and the Fab fragment comprises the PD-L1 binding site. The scFv is connected to the C-terminus of the Fc domain, and the scFv comprises the OX40 binding site.

In one embodiment, the polypeptide chain further comprises a linker between the Fc domain and the scFv.

In one embodiment, the scFv comprises an amino acid sequence selected from the group consisting of amino acid 455-707 of SEQ ID NO: 18, 455-708 of SEQ ID NO: 19, 455-701 of SEQ ID NO: 20, 455-706 of SEQ ID NO: 21, 455-706 of SEQ ID NO: 22, 455-706 of SEQ ID NO: 23, 455-706 of SEQ ID NO: 24, 455-706 of SEQ ID NO: 25, 455-706 of SEQ ID NO: 26, 455-706 of SEQ ID NO: 27, 455-706 of SEQ ID NO: 28, and 455-706 of SEQ ID NO: 29.

In one embodiment, the bispecific antibody comprises one pairs of polypeptide chains.

In one embodiment, the bispecific antibody is an IgG, IgE, IgM, IgD, IgA, or IgY antibody.

In one embodiment, the bispecific antibody is an IgG antibody.

In one embodiment, the IgG antibody is an IgG1, IgG2, IgG3, or IgG4 antibody.

The present disclosure also provides an antibody-drug conjugate comprising a therapeutic agent, and an antibody or an antigen-binding portion binding PD-L1 and/or OX40, wherein the therapeutic agent is covalently conjugated to the antibody or the antigen-binding portion by a linker.

In one embodiment, the antibody or an antigen-binding portion is selected from the above mentioned antibody or an antigen-binding portion.

The present disclosure also provides a pharmaceutical composition comprising the antibody, the antigen-binding portion thereof, or the bispecific antibody as above mentioned, and at least one pharmaceutically acceptable carrier.

The present disclosure also provides a method of treating cancer comprising administering to the subject in need thereof an effective amount of the antibody, the antigen-binding portion thereof, or the bispecific antibody as above mentioned.

In one embodiment, the cancer is selected from the group consisting of prostate cancer, lung cancer, Non-Small Cell Lung Cancer (NSCLC), melanoma, lymphoma, breast cancer, head and neck cancer, renal cell carcinoma (RCC), and ovarian cancer.

The present disclosure also provides a nucleic acid molecule encoding the antibody, the antigen-binding portion thereof, or the bispecific antibody as above mentioned.

It is to be understood that both the foregoing general description and the following detailed description are by examples, and are intended to provide further explanation of the invention as claimed.

BRIEF DESCRIPTION OF THE DRAWINGS

The invention can be more fully understood by reading the following detailed description of the embodiment, with reference made to the accompanying drawings as follows:

FIGS. 3A and 3B show the screening of phage clone by cell-based ELISA with OX40 expressed HEK293 cells.

FIG. 18 shows sequence variants among OX40 clone B17 scFv of Anti-PD-L1-OX40 Ab-V4 to V12 (SEQ ID NO: 30-38).

DETAILED DESCRIPTION

Figure 1:
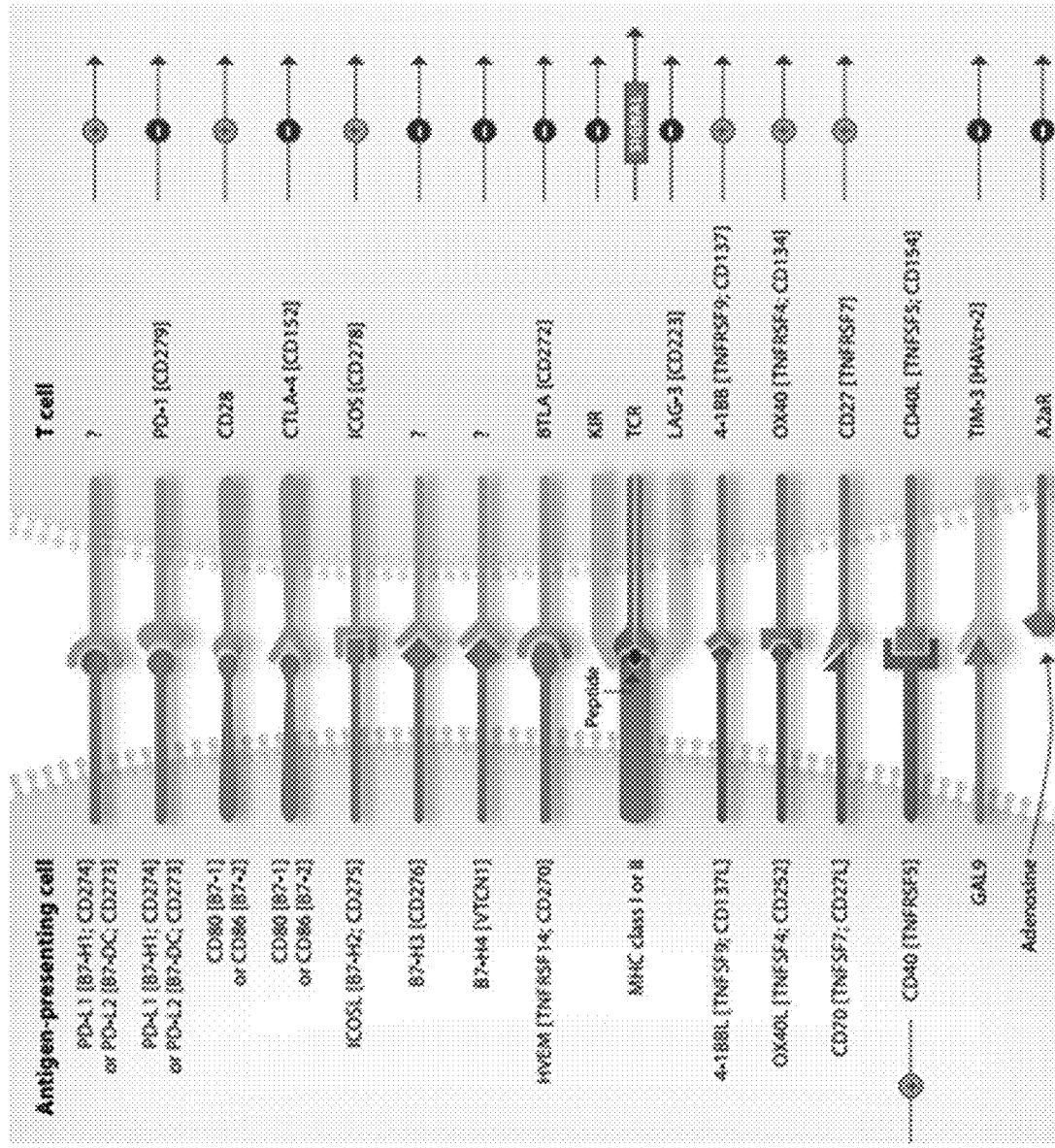
FIG. 1 shows immune checkpoints modulating T-cell mediated immunity. Antibody either agonistic or antagonistic against the checkpoints, such as anti-ICOS, anti-CD28, anti-OX40, and anti-CD27, or anti-PD-1, anti-CTLA4, anti-LAG3, anti-BTLA, could be used to construct the bifunctional fusion protein depending on applications.
Figure 2A:
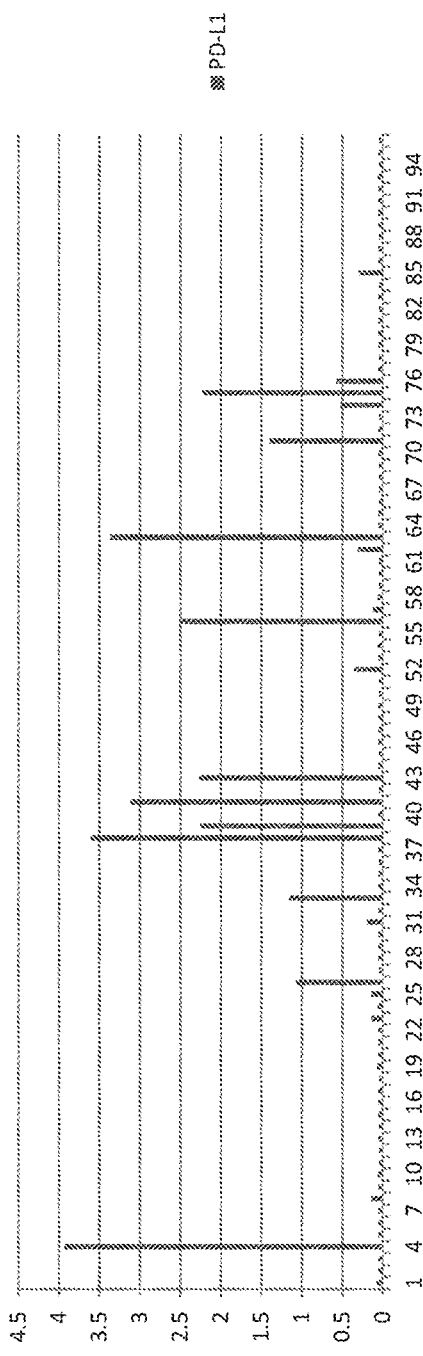
FIGS. 2A and 2B show the screening of phage clone by direct ELISA for PD-L1 expressed HEK293 cells.
Figure 2B:
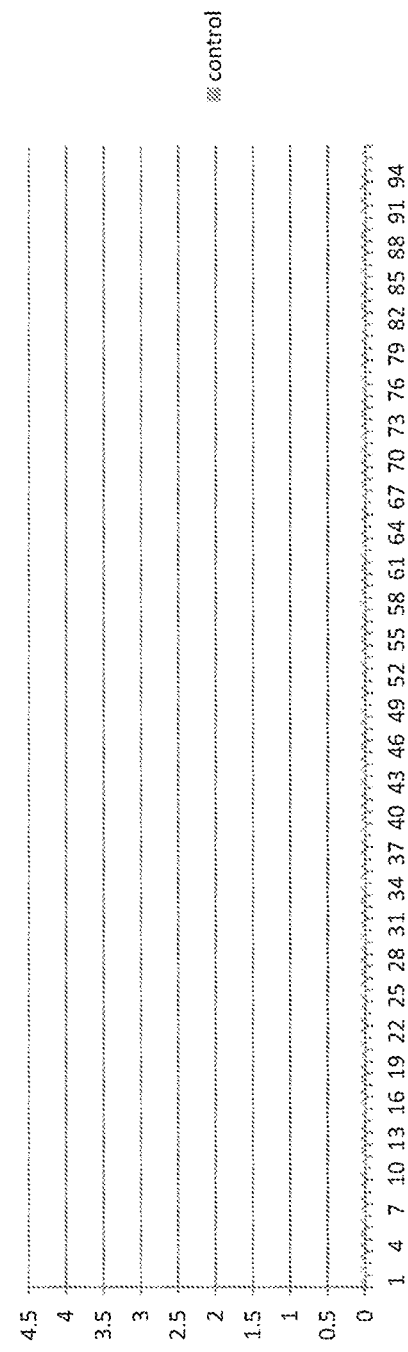

Reference will now be made in detail to the present embodiments of the invention, examples of which are illustrated in the accompanying drawings. Wherever possible, the same reference numbers are used in the drawings and the description to refer to the same or like parts.

The present invention describes the expression, purification and characterization of bi-functional proteins with isolated functional agonistic OX40 scFv fused to the C-terminus of Fc domain of anti-immune checkpoint protein antibodies. These proteins interact with its corresponding check point target shall transmit the inhibitory or stimulatory signal to modulate T-cell involved immunity. The components of Fc fusion proteins in present invention are of all human origins, and thus are expected to be non-immunogenic and can be used as therapeutics in human.

Bispecific molecules such as bispecific antibodies (Bs-Abs) provide a means of simultaneously targeting multiple epitopes on the same molecular target or different targets with a single therapeutic agent. As cancer therapeutics, they have the potential to confer novel or more potent activities, lower the cost of goods and facilitate the development of new therapeutic regimens in contrast to a mixture of two mAbs (Chames and Baty, 2009; Hollander, 2009; Thakur and Lum, 2010). Recently, catumaxomab, a trifunctional bispecific antibody targeting human epithelial cell adhesion molecule (EpCAM) and CD3 has shown a clear clinical benefit in patients with peritoneal carcinomatosis of epithelial cancers (Heiss et al., 2010), and a bispecific T-cell engaging (BiTE) antibody with dual specificity for CD19 and CD3 has also demonstrated encouraging clinical activity in patients with CD19 expressing hematological malignancies (Bargou et al., 2008). Despite strong interest in the development of bispecific molecules as cancer therapeutics, technical challenges in the production of stable and active bispecific molecules have in the past hindered the clinical evaluation of most bispecific formats. Many engineered antibody formats, including an IgG-like bispecific antibody have compromised stability or solubility (Bargou et al., 2008; Demarest and Glaser, 2008; Lu et al., 2005). Furthermore, several strategies have been taken to increase the product quality and in vivo stability of bispecific molecules, including PEGylation, conjugation with human serum albumin and Fc engineering (Muller et al., 2007; Ridgway et al., 1996). Bispecific single chain antibodies of the general form described above have the advantage that the nucleotide sequence encoding the four V-domains, two linkers and one spacer can be incorporated into a suitable host expression organism under the control of a single promoter. This increases the flexibility with which these constructs can be designed as well as the degree of experimenter control during their production. In addition, the Fc of IgG is a very another attractive scaffold for designing novel therapeutics because it contains all antibody functions except the binding ability. Fc engineering is important for improving the effectiveness of the bispecific antibodies. Therefore, the IgG-based conformation is using in present invention for two independent target on immune cells or target cell in immunotherapy.

Targeting immune-check point proteins are promising approaches to activate antitumor immunity. Anti-check point proteins, such as PD-1, PD-L1, CTLA-4, LAG3, etc., are currently evaluated clinically (FIG. 1). Preliminary data with blockers of immune checkpoint proteins have been shown to be able to enhance antitumor immunity with the potential to produce durable clinical responses. However, despite the remarkable clinical efficacy of these agents in a number of malignancies, it has become clear that they are not sufficiently active for many patients. Numerous additional immunomodulatory pathways as well as inhibitory factors expressed or secreted by myeloid and stromal cells in the tumor microenvironment are potential targets for synergizing with immune checkpoint blockade. Therefore, combining anticancer or bispecific antibody therapies has been essential to achieve complete remission and cures for patients with cancer.

The present invention describes the construction, expression and characterization of anti-immune checkpoint protein antibody Fc fused with different immune checkpoint protein specific scFv protein. The C-terminally positioned OX40 scFv in fusion constructs shall allow expanding the power of fusion proteins beyond OX40 activation approach if the fusion counterpart is immune system potentiating agent, such as anti-EGFR, anti-HER2, or anti-CTLA-4 antibody, for example.

Antibody Generation from OmniMab Library

For the generation of therapeutic antibodies against PD-L1 or OX40, selections with the OmniMab phagemid library were carried out. The phagemid library is generated by AP Biosciences Inc. (APBio Inc.) from a collection of over hundred health donors B cells. Phages for the 1st round of pannings were prepared by Hyperphage (M13K07ΔμIII, Progen, Heidelberg, Germany). Solid phase panning and cell panning against PD-L1 or OX40 were applied for PD-L1 or OX40 specific binder selection and isolation from OmniMab library. Solid phase panning was performed using recombinant human PD-L1-Fc or OX40-Fc (APBio Inc.) in the first round selection and then HEK293 cells expressed PD-L1 or OX40 were used for two and three round enrichment. After three rounds selection, the specific PD-L1 or OX40 binders were screened and isolated by direct ELISA or cell-based ELISA with corresponding recombinant protein (FIGS. 2A 2B, 3A, and 3B). Pre-coated PD-L1-Fc recombinant proteins or OX40 expressed 293 cells were blotted with supernatant containing rescued phages for 1 hour and washed with PBS containing 0.1% Tween-20 for three times. Bound phages were detected by HRP conjugated anti-M13 antibody (Roche) and TMB substrate was used for signal development. The OD450 readings were recorded. The positive binders were isolated and sent for sequencing to confirm the sequence and diversity of heavy chain and light chain. The variable region of heavy chain and light chain specific to PD-L1 or OX40 were described from the SEQ ID NO: 1 to SEQ ID NO: 8: SEQ ID NO: 1 is the light chain of PD-L1 clone 6, SEQ ID NO: 2 is the variable region of heavy chain of PD-L1 clone 6, SEQ ID NO: 3 is the light chain of PD-L1 clone 32, SEQ ID NO: 4 is the variable region of heavy chain of PD-L1 clone 32, SEQ ID NO: 5 is the light chain of OX40 clone B17, SEQ ID NO: 6 is the variable region of heavy chain of OX40 clone B17, SEQ ID NO: 7 is the light chain of OX40 clone B19, SEQ ID NO: 8 is the variable region of heavy chain of OX40 clone B19. As shown in the FIGS. 2A, 2B, 3A and 3B, several clones were isolated and known to be recognized specifically for corresponding antigen as comparing with negative control.

Figure 4:
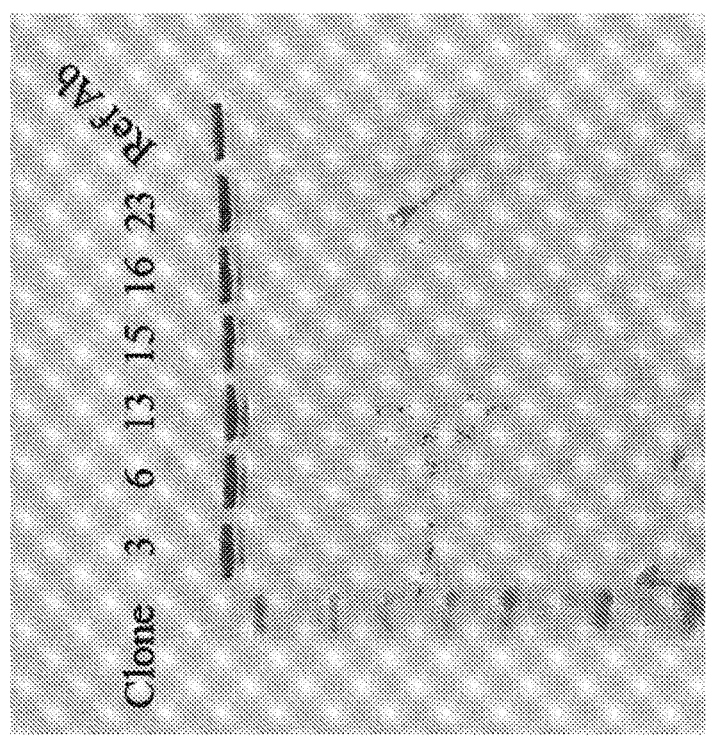
FIG. 4 shows purified antibody leads specific for PD-L1 by SDS-PAGE with non-reducing reagent to reveal the integrity and purity.
Figure 5:
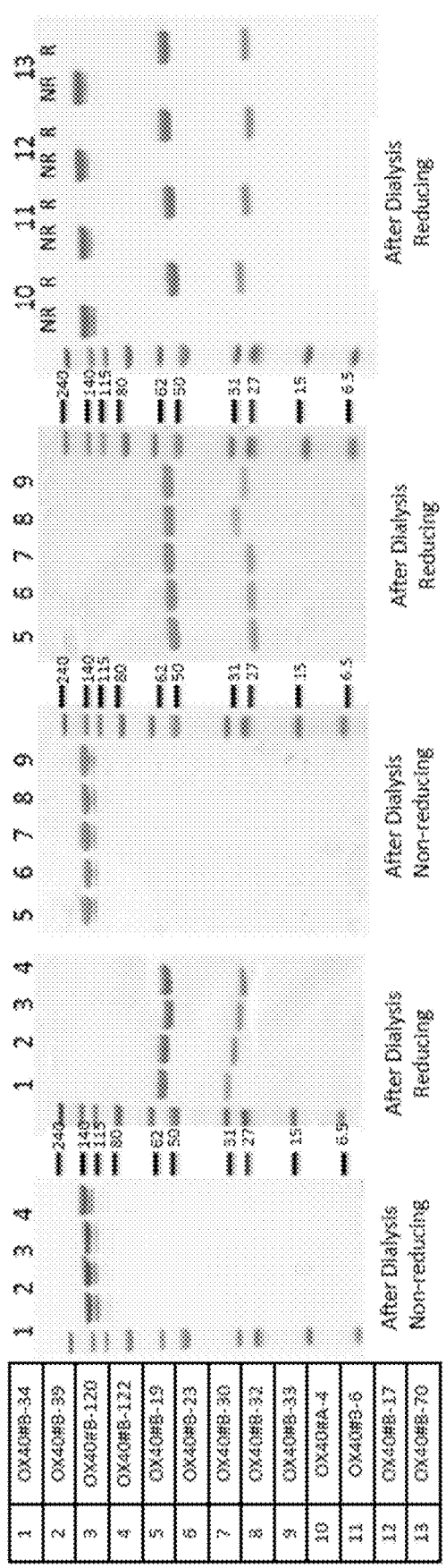
FIG. 5 shows purified antibody leads specific for OX40 by SDS-PAGE with non-reducing or reducing reagent to reveal the integrity and purity.

Subcloning and Expression/Purification of Selected PD-L1 or OX40 Specific Binder as IgG Format To facilitate the quick screening of specific binder with functionality in T cell activation, the heavy chains and light chains of positive binders against PD-L1 or OX40 by ELISA were then amplified, digested and sub-clone into APBio specialized IgG expression vector carrying IgG4 constant region (SEQ ID NO: 9). After sequence validation, the plasmids were then prepared and transfected into HEK293 cells for antibody expression with 293 fectin transfection reagent (Invitrogen). After 4 days culture, the antibody secreted into serum-free medium is affinity purified from culture supernatant by Protein G chromatography. Purified antibody is then concentrated, followed by dialysis in PBS buffer. The final concentration of dialyzed protein is determined by NanoDrop2000 spectrophotometer and the purity and integrity are determined by SDS-PAGE with or without reducing reagent as shown in the FIGS. 4 and 5. The integrity of various purified antibody leads, either PD-L1 specific or OX40 specific, is normal in the HEK293 cells as well as reference antibody, MPDL3280A for PD-L1 or GSK3174998 for OX40.

In one embodiment, the present disclosure provides an antibody or an antigen-binding portion thereof binding to OX40 (CD134), comprising a heavy chain variable region and a light chain variable region. The heavy chain variable region comprises an amino acid sequence of at least about 80% sequence homology to the amino acid sequence selected from the group consisting of SEQ ID NO: 6, SEQ ID NO: 8, amino acid 128-246 of SEQ ID NO: 10, and amino acid 124-241 SEQ ID NO: 13. In some examples, the heavy chain variable region comprises an amino acid sequence of at least about 85%, 90%, or 95% sequence homology to the amino acid sequence as above mentioned. The light chain variable region comprising an amino acid sequence of at least about 80% homology to the amino acid sequence selected from the group consisting of amino acid 1-108 of SEQ ID NO: 5, 1-108 of SEQ ID NO: 7, 1-112 of SEQ ID NO: 10, and 1-108 of SEQ ID NO: 13. In some examples, the light chain variable region comprises an amino acid sequence of at least about 85%, 90%, or 95% sequence homology to the amino acid sequence as above mentioned.

In one embodiment, the present disclosure provides an antibody or an antigen-binding portion thereof binding to PD-L1, comprising a heavy chain variable domain and a light chain variable domain. The heavy chain variable domain comprises an amino acid sequence of at least about 80% sequence homology to the amino acid sequence selected from the group consisting of SEQ ID NO: 2 and SEQ ID NO: 4. In some examples, the heavy chain variable region comprises an amino acid sequence of at least about 85%, 90%, or 95% sequence homology to the amino acid sequence as above mentioned. The light chain variable domain comprises an amino acid sequence of at least about 80% homology to the amino acid sequence selected from the group consisting of amino acid 1-111 of SEQ ID NO: 1 and 1-110 of SEQ ID NO: 3. In some examples, the light chain variable region comprises an amino acid sequence of at least about 85%, 90%, or 95% sequence homology to the amino acid sequence as above mentioned.

Figure 6:
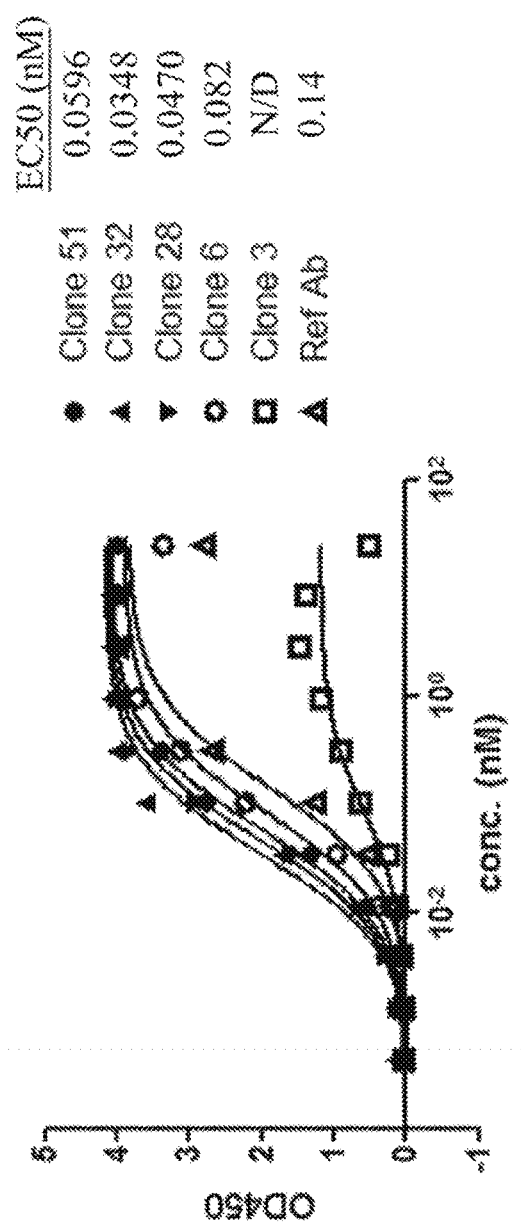
FIG. 6 shows examples of the direct ligand binding activity of purified anti-immune check point proteins and anti-PD-L1 antibody leads against PD-L1. Ligand pre-coated wells were first incubated with various concentrations of antibody leads as indicated. The bound proteins were then detected with HRP conjugated goat anti-human IgG Fab specific antibody and OD450 readings were plotted.
Figure 7:
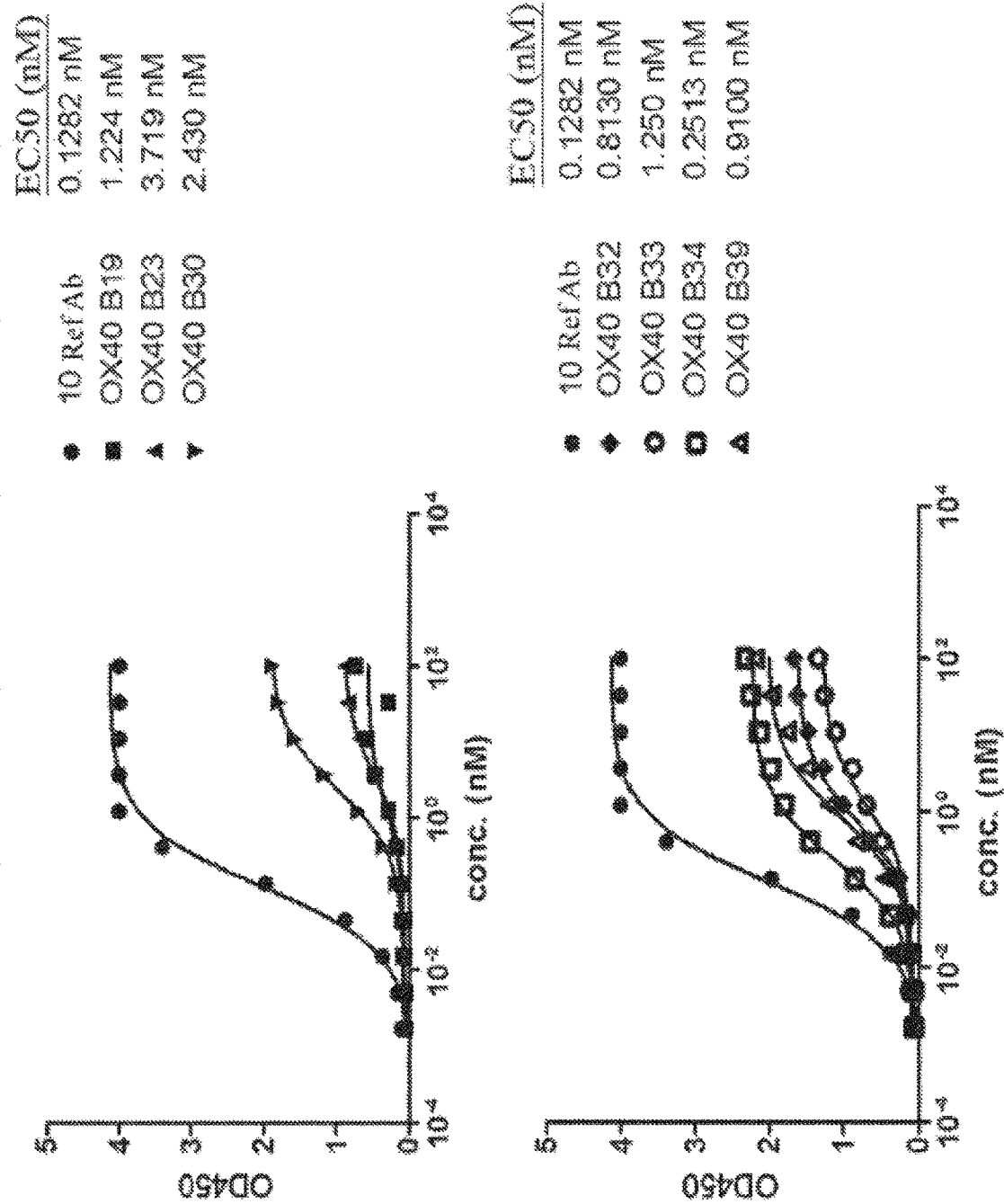
FIG. 7 shows examples of the direct ligand binding activity of purified anti-immune check point proteins and anti-OX40 antibody leads against OX40. Ligand pre-coated wells were first incubated with various concentrations of antibody leads as indicated. The bound proteins were then detected with HRP conjugated goat anti-human IgG Fab specific antibody and OD450 readings were plotted.

Binding Activity Determination for PD-L1, OX40 Specific IgG Leads by Direct ELISA Purified antibody leads against PD-L1 or OX40 (anti-PD-L1 antibody leads or anti-OX40 antibody leads) were then applied for ELISA binding characterization on human PD-L1-Fc or OX40-Fc in a direct coated setup. FIGS. 6 and 7 showed the ELISA binding result for anti-PD-L1 and anti-OX40 antibodies, respectively. For PD-L1 specific antibodies, most leads showed a similar or better binding activity with reference antibody (Ref Ab, MPDL3280A, Roche).

Purified human PD-L1 or OX40 IgG1 Fc chimera (PD-L1-Fc or OX40-Fc, APBio) was dialyzed in Phosphate Buffered Saline (PBS), adjusted to 1 mg/mL and then diluted with PBS to a final concentration of 1 μg/mL. Nunc-Immuno Maxisorp 96 well plates were coated with 0.1 mL per well of recombinant PD-L1-Fc or OX40-Fc chimera leaving empty wells for nonspecific binding controls and incubated at 4° C. overnight. The PD-L1-Fc or OX40-Fc chimera solution was removed and the plates were washed three times with 0.4 mL wash buffer (0.1% Tween-20 in PBS). 0.4 mL blocking buffer (5% low-fat milk powder in PBS) was added to all wells and incubated at room temperature for 1 hour with mixing. The blocking buffer was removed and plates washed three times with 0.4 ml wash buffer. Serial dilutions of the PD-L1 or OX40 test antibodies were prepared in PBS and 0.1 mL diluted Ab was added per well. Plates were incubated 1 hour at room temperature. Antibody solution was removed and the plates washed three time with 0.4 mL wash buffer per well. Horseradish peroxidase labeled goat anti-human IgG, F(ab')$_2$ specific F(ab')$_2$ antibody (Jackson Immunoresearch #109-036-097) was diluted 1:2000 with PBS and added 0.1 mL per well. The plates were incubated 1 hour at room temperature and washed with 0.4 mL per well wash buffer. 0.1 mL TMB reagent (Invitrogen) was added and incubated for 1 to 5 minutes at room temperature. The reaction was stopped by adding 0.05 mL 1N HCl and absorbance was read at 450 nm on a Bio-Tek Spectra. Calculated EC50 for anti-PD-L1 antibody leads to PD-L1 showed most leads possess good binding activity as well as MPDL3280A (Ref Ab) by direct ELISA (FIG. 6). On the contrary, most anti-OX40 antibody leads showed much lower binding activity as comparing with reference antibody (Ref Ab, GSK3174998) (FIG. 7).

Binding Activity Determination for PD-L1 and OX40 Specific IgG Leads by FACS

Figure 8:
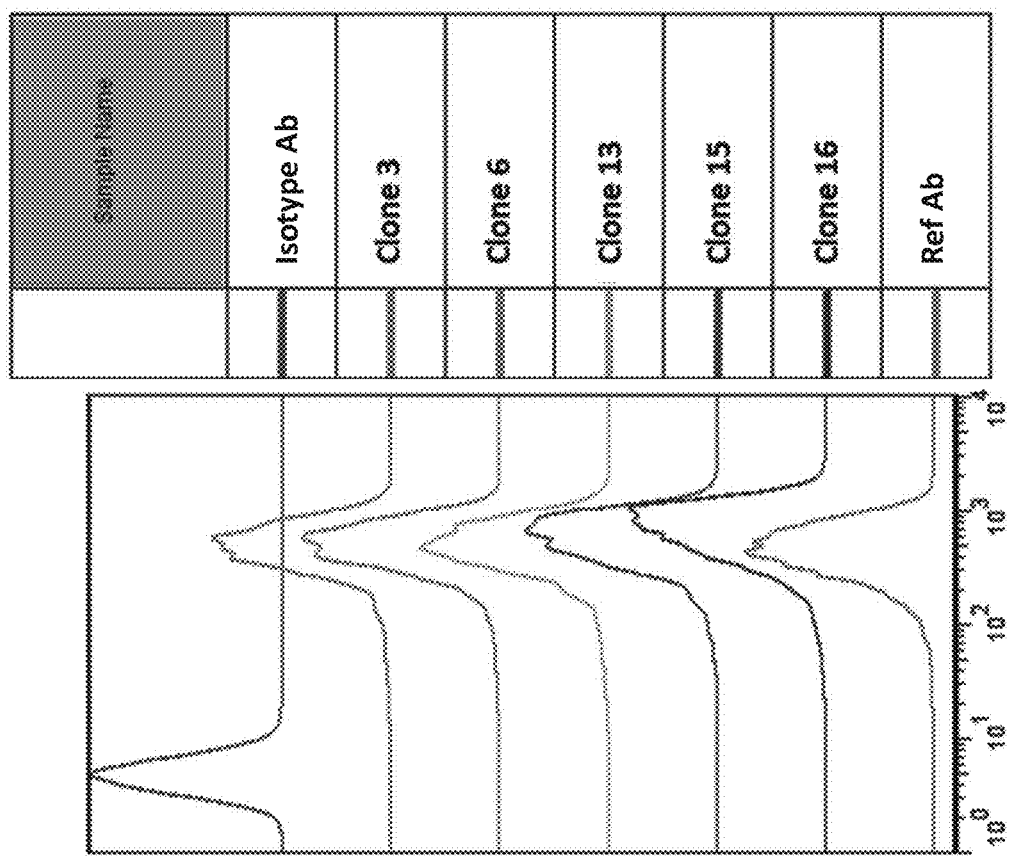
FIG. 8 shows the flow analysis using PD-L1 expression 293 cells. PD-L1 expression HEK293 cells were first incubated with purified antibody leads, and the bound antibodies were detected with Alexa-488 conjugated goat anti-human IgG (H+L) followed by fluorescence-activated cell sorter (FACS) analysis.
Figure 9:
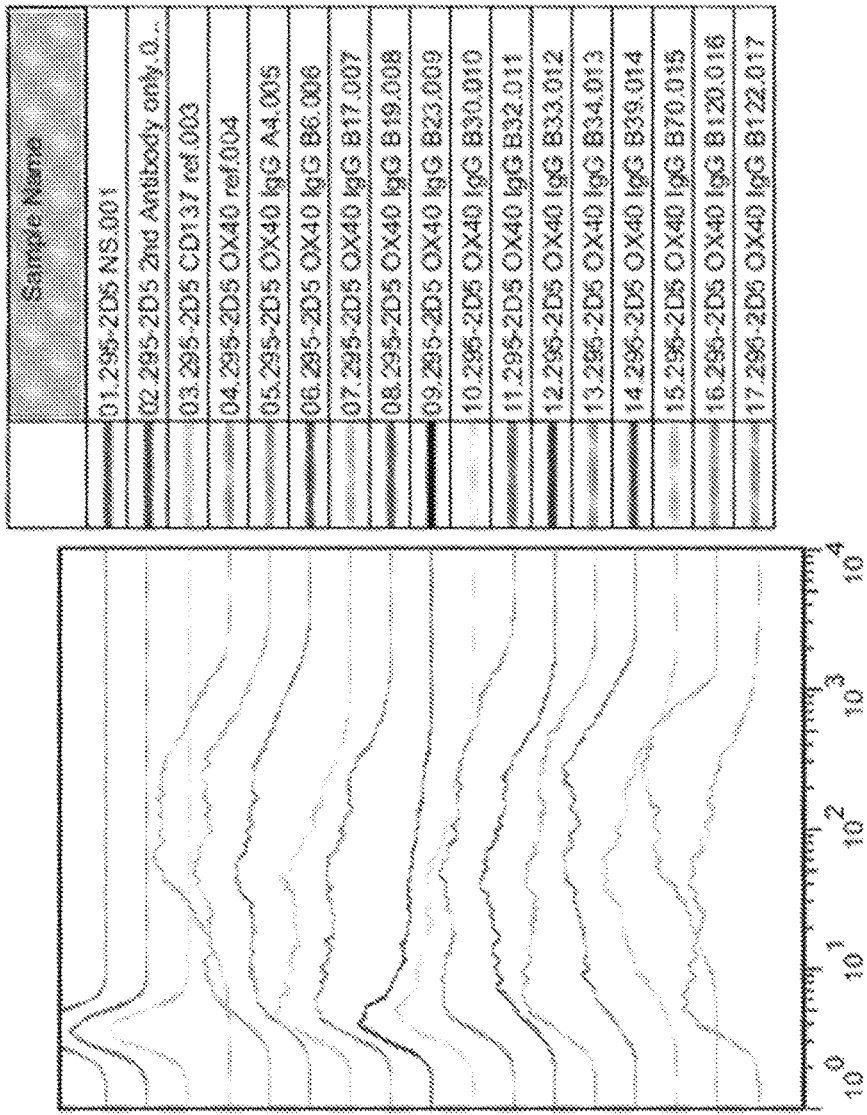
FIG. 9 shows the flow analysis using OX40 expression 293 cells. OX40 expression HEK293 cells were first incubated with purified anti-OX40 antibody leads, and the bound antibodies were detected with Alexa-488 conjugated goat anti-human IgG (H+L) followed by FACS analysis. NS: no staining.

Purified antibody leads (anti-PD-L1 antibody leads or anti-OX40 antibody leads) were also applied for flow cytometry to determine and compare the binding activity with PD-L1 or OX40 expressed HEK293 cells. FIGS. 8 and 9 show the binding activity of corresponding antibody leads as indicated by FACS with stable expressed PD-L1 or OX40 HEK293 cells.

FACS analysis of PD-L1 stable expression 293 cells stained with anti-PD-L1 antibody leads to examine the PD-L1 binding activity, stable expression cells were incubated with 1 μg/mL purified anti-PD-L1 antibody leads, reference antibody (Ref Ab MPDL3280A) or with isotype antibody as negative control on ice for 1 hr. The cells were washed three times with 1×PBS and then incubated with Alexa-488-conjugated goat anti-human IgG (H+L) (Invitrogen Inc.) on ice for additional 1 hr. After staining, the cells were washed three times with 1×PBS, resuspended in 1×PBS/2% FBS before analyzed by FACS Calibur (BD Biosciences, Inc.) and FlowJo (TreeStar, LLC). Same scenario, the binding activity of anti-OX40 antibody leads for stable expressed OX40 HEK293 cells in FIG. 9 were also executed with a similar strategy and analyzed as described above. As shown in the FIG. 8, most anti-PD-L1 antibody leads possess a good binding activity as well as reference antibody. This indicated the phage clones selected from the OmniMab library indeed recognize the native PD-L1 in the cells.

This phenomenon is also observed for anti-OX40 antibody leads as shown in the FIG. 9. FACS analysis of OX40 stable expression 293 cells clone 2D5 stained with purified anti-OX40 antibodies leads to examine the OX40 binding activity, stable expression cells were incubated with 2 μg/mL anti-OX40 reference Abs (OX40 ref.) or anti-CD137 reference Abs (CD137 ref.) as control antibody on ice for 1 hr. The cells were washed three times with 1×PBS and then incubated with Alexa-488-conjugated goat anti-human IgG (H+L) (Invitrogen Inc.) on ice for additional 1 hr. After staining, the cells were washed three times with 1×PBS, resuspended in 1×PBS/2% FBS before analyzed by FACS Calibur (BD Biosciences, Inc.) and FlowJo (TreeStar, LLC).

Ligand Competition Binding (ELISA Assay)

Antibody leads were exposed to the binding selectivity and affinity assay used to evaluate the anti-PD-L1 antibody leads of the present invention for their ability to block binding of PD-L1 to PD-1.

Figure 10:
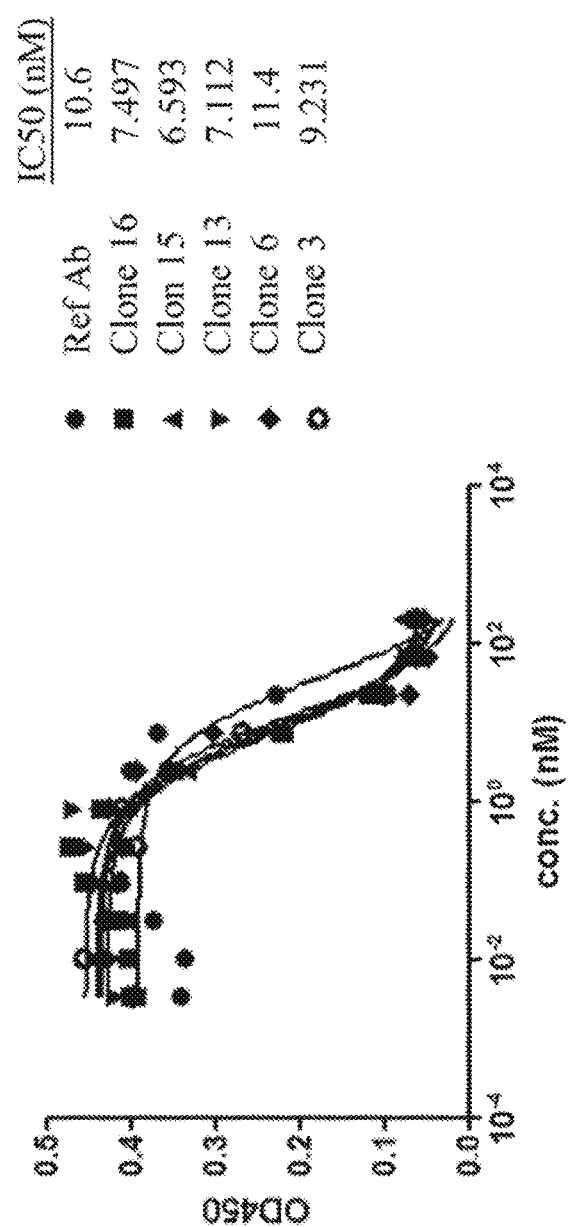
FIG. 10 shows the blockage of PD-1/PD-L1 interaction with purified anti-PD-L1 antibodies. Purified antibodies as indicated were applied with biotinylated-PD-L1-Fc and recombinant human PD-1/His (hPD-1/His) to evaluate the inhibition activity of PD-1/PD-L1 interaction. The binding recombinant PD-L1-Fc and hPD-1/His was detected by streptavidin-HRP and analysis by ELISA.

Antibodies were tested for their ability to block the binding of the human PD-L1-Fc chimera (PD-L1-Fc) to recombinant human PD-1/His (hPD-1/His) by ELISA. Purified recombinant hPD-1/His (APBio) was dialyzed to 1 mg/ml in PBS and then conjugated with biotin (Abcam). Nunc Maxisorp 96 well plate was coated with 250 ng hPD-1/His per well in PBS overnight. The hPD-1/His solution was removed and the plates were washed three times with 0.4 mL wash buffer (0.1% Tween-20 in PBS). 0.4 mL blocking buffer (5% low-fat milk powder in PBS) was added to all wells and incubated at room temperature for 1 hour with mixing. During the blocking step the antibody stocks were diluted in a range from 200 nM to 0 nM in PBS with 2 folds serial dilution. Purified recombinant biotinylated-PD-L1-Fc chimera was diluted to 4 µg/mL in PBS. The PD-1/His coated plates were washed three times with 0.2 mL wash buffer (0.1% Tween 20 in PBS). 60 µL antibody dilutions (anti-PD-L1 antibody leads or Ref Ab MPDL3280A) were added alone with 60 µL biotinylated-PD-L1-Fc chimera and incubated at room temperature for 1 hour. Plates were washed as described previously. Streptavidin-HRP was diluted 1:2000 in PBS, 100 µL of the resulting solution added to the wells of the washed plated, and incubated at room temperature for 1 hour. Plates were washed as previously described, 100 µL TMB substrate solution was added to each well and incubated for 10 minutes. The reaction was stopped with 50 µL 1N HCl and absorbance at 450 nm read using Bio-Tek reader and shown in FIG. 10. Partial antibody leads are shown to inhibit the interaction between PD-PD-L1 by competition ELISA. Most antibody leads revealed a similar blocking activity as comparing with reference antibody (Ref Ab MPDL3280A).

Enhanced Stimulation of T Cell Activation by Inhibition of PD-1:PD-L1 Ligand Interaction for Anti-PD-L1 Antibody The PD-1 signaling pathway inhibits moderate TCR/CD28 costimulatory signals, with cytokine production being reduced first without a decrease in T cell proliferation. As the TCR/CD28 costimulatory signals weaken, the PD-1 pathway dominates, with a great reduction in cytokine production accompanied by a reduction in proliferation. Accordingly in order to confirm that the inhibition of the PD-1 via inhibition of the interaction with PD-L1, human antibodies of the invention enhances T cell activation, mixed lymphocyte reactions (MLRs) are performed.

Monocytes from human whole blood were enriched by RosetteSep™ Human Monocyte Enrichment Cocktail (Cat. No. 15068) and cultured in differentiation medium, RPMI 1640 with 10% FBS, 100 ng/ml (1000 U/mL) GM-CSF, 100 ng/ml (500 U/mL) for 6 days. The differentiate dendritic cells (DC) from monocyte were checked by DC-SIGN-PE, anti-CD14 conjugated with FITC Ab, anti-CD83 conjugated with PE Ab, or anti-CD80 conjugated with FITC Ab to validate the differentiation and used to be APCs in MLRs.

Figures 11A, 11B:
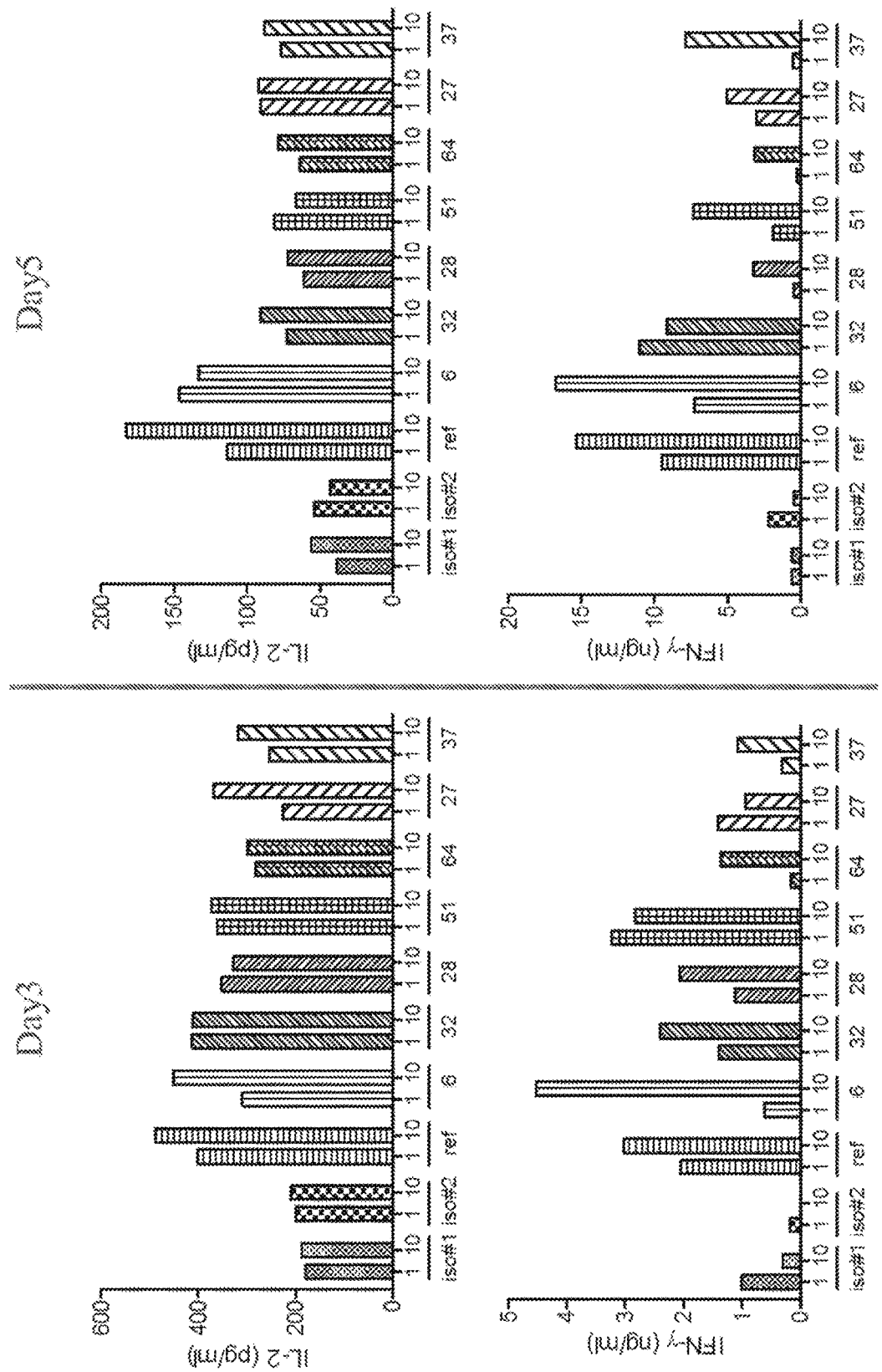
FIGS. 11A and 11B show anti-PD-L1 antibody leads with 1 or 10 μg/mL stimulates T-cell proliferation and induces IL-2 and/or IFN-γ production in a mixed lymphocyte reaction (MLR) assay after 3 days (FIG. 11A) or 5 days (FIG. 11B) antibody treatment.

Allogenic CD4+ T cells from human whole blood were isolated by RosetteSep™ Human CD4+ T Cell Enrichment Cocktail (Cat. No. 15062). The purity of CD4+ T cells were checked with anti-CD4 conjugated APC Ab to make sure the purity is above 95% and then labeled with 1 uM CFSE (CellTrace™ CFSE cell proliferation kit, Life technologies, Cat. No. C34554) for T cells proliferation assay. Labeled CD4+ T cells were used to co-culture with immature DC with different antibody leads as indicated for 3 and 5 days to see whether the antibody leads could restore the T cell activation through blocking the interaction between PD-1 and PD-L1. After 3 and 5 days incubation, the supernatant were collected for cytokine, such as IL-2 and IFN-γ quantitation by ELISA. The addition of anti-PD-L1 antibody leads (clones 6, 32, 28, 51, 64, 27, and 37) to cultures of immature dendritic cells plus allogeneic T cells is predicted to result in an increase in T cell proliferation and cytokine production, as compared to isotype IgG (iso #1, #2) treated cultures and shown in the FIGS. 11A and 11B. The IL-2 and IFN-γ production increase significantly in the MLRs as comparing with isotype antibody treatment after 3 days (FIG. 11A) or 5 days (FIG. 11B) antibody treatment, especially for anti-PD-L1 antibody clone 6. The cytokine increment is still obviously after 5 days antibody treatment and similar to reference antibody (ref), MPDL3280A. This indicated the anti-PD-L1 antibody clone 6 should be one of the potential leads for bispecific antibody composite.

Agonistic Activity Assay of Anti-OX40 Antibody

In order to activate OX40 costimulation of T-cell proliferation and cytokine production, the purified antibody leads were functionally screened for their ability to enhance cytokine production, proliferation, and to induce proliferation in human CD3+ T-cells. The anti-CD3 antibody (OKT3, BioLegend Cat. No. 317304) and anti-OX40 antibody leads (clones B6, B70, B120, A4, B17, B19, and B30), reference antibody (GSK3174998) or isotype antibodies (iso #1, #2) were coated in the Maxisorp 96-well plate. Meanwhile, naïve human CD3+ T-cells were isolated from the human blood from heathy adult volunteers using a commercially available RosetteSep™ Human T Cell Enrichment Cocktail (STEMCELL Cat. No. 15061) as manufacture's described. The isolated CD3+ T cells were then labeled by CFSE (CellTrace™ CFSE cell proliferation kit, Life technologies, Cat. No. C34554) and seeded as $1\times10^6$ cells/mL into the antibody pre-coated well containing RPMI 1640 medium, 10% fetal bovine serum and 2.5 mM L-glutamine to determine the cell proliferation and cytokine production. After 3 days culture, the cells were collected for proliferation assay by flow cytometry and medium were then analyzed for IL-2 and IFN-γ production by quantitation ELISA.

Figure 12A:
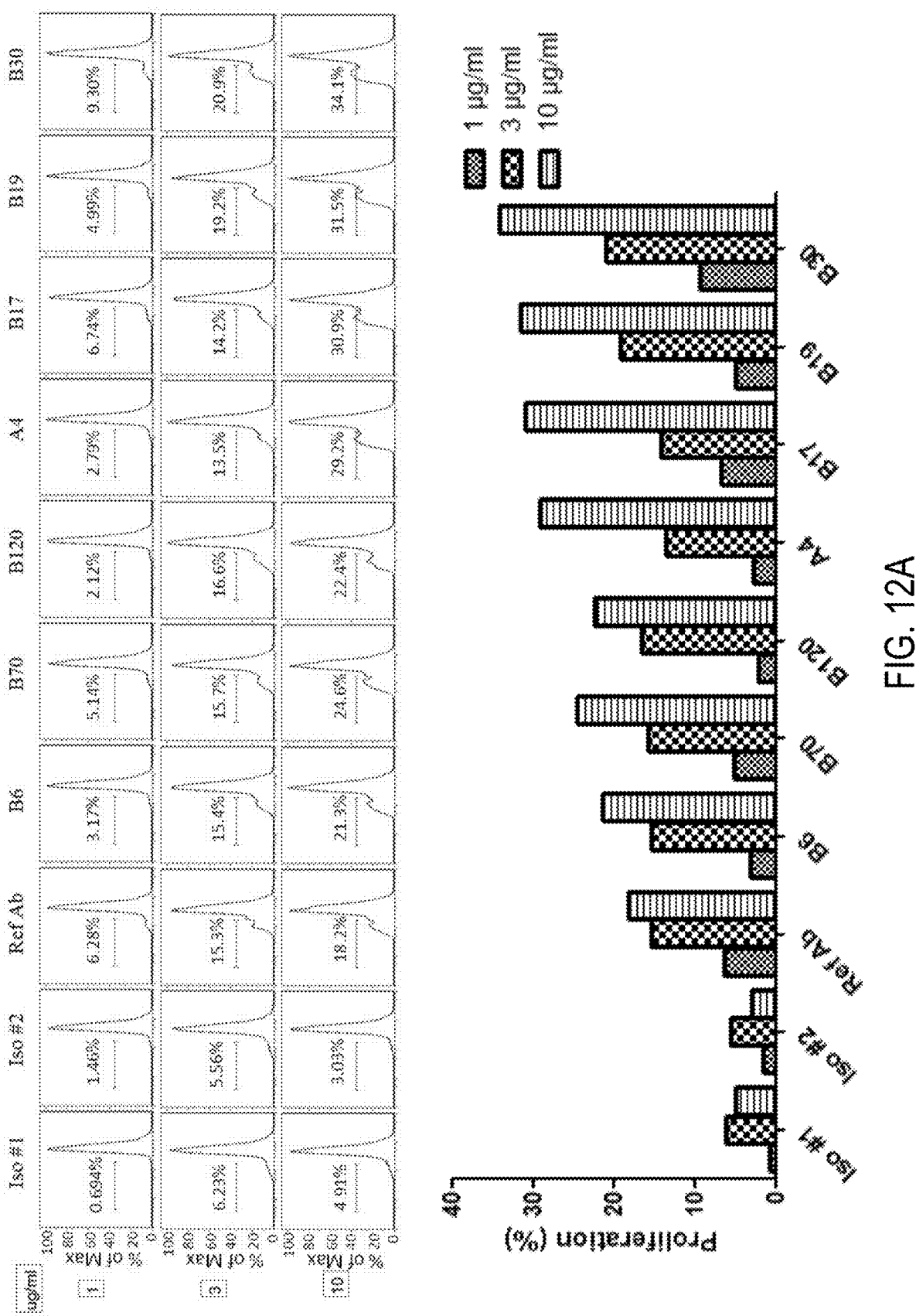
FIG. 12A shows the ability of anti-OX40 antibody leads to enhance the CD3+ T cell activation with dosage response as well as reference antibody.
Figure 12B:
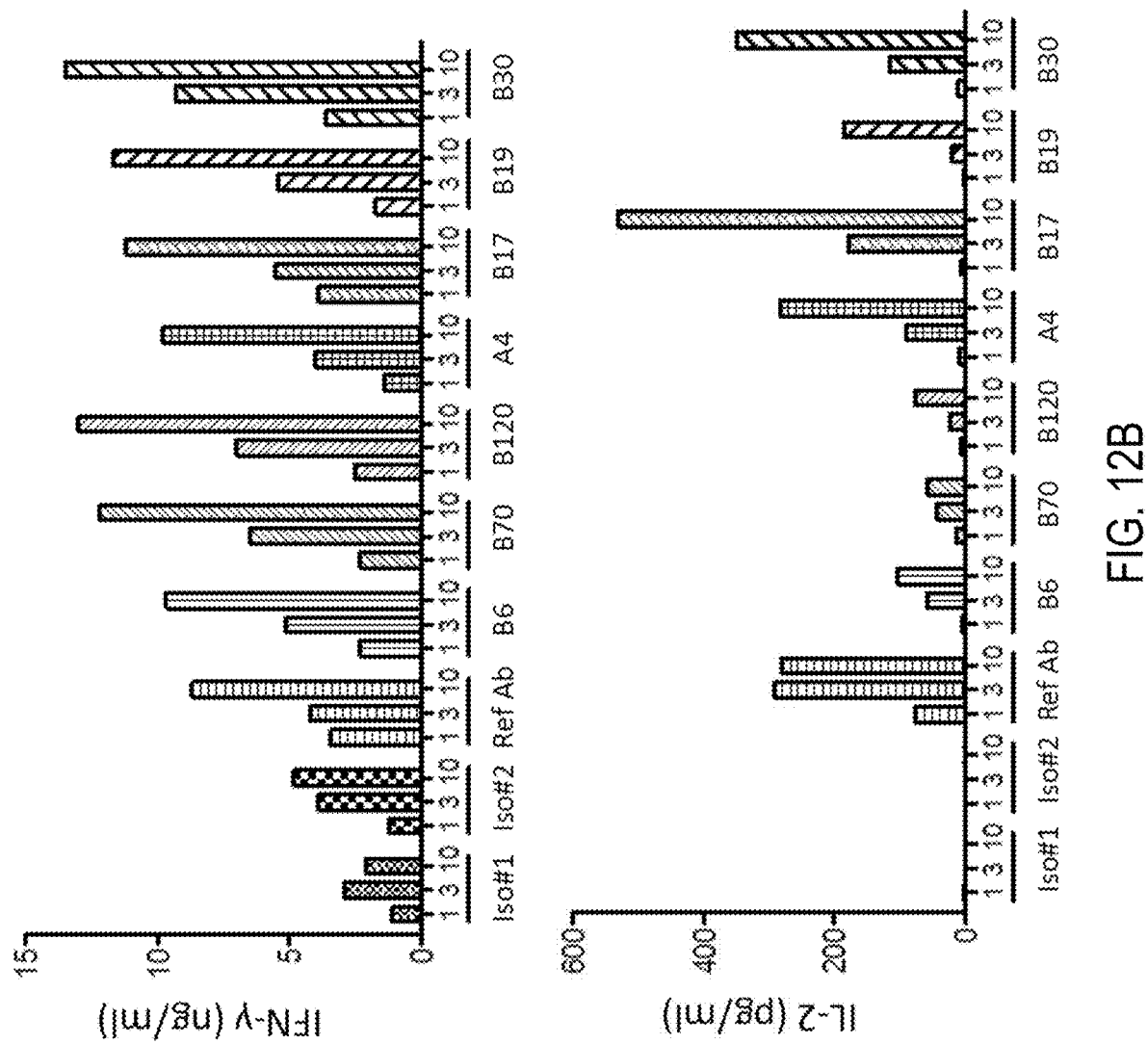
FIG. 12B shows the concentration of human IL-2 and IFN-γ present in cell culture media following 3 days of stimulation of human T cells with plate bound anti-CD3 and several concentrations of anti-OX40 antibody leads.

The screening of anti-OX40 antibody leads with agonistic activity in T cell activation was shown in the FIG. 12A. All anti-OX40 antibody leads showed the ability to enhance the CD3+ T cell activation with dosage response as well as reference antibody. Higher dosage antibody treatment showed obviously higher T cell activation activity. Meanwhile, cytokine production (FIG. 12B), such as IL-2 and IFN-γ also revealed similar T cell activation response, especially for anti-OX40 antibody lead clone B17. Cytokine is highly inducted after anti-OX40 antibody lead B17 3 days treatment. The enhancement is much higher than reference antibody treatment, this implicated clone B17 should be one of the candidates for bispecific antibody construction.

Figure 13A:
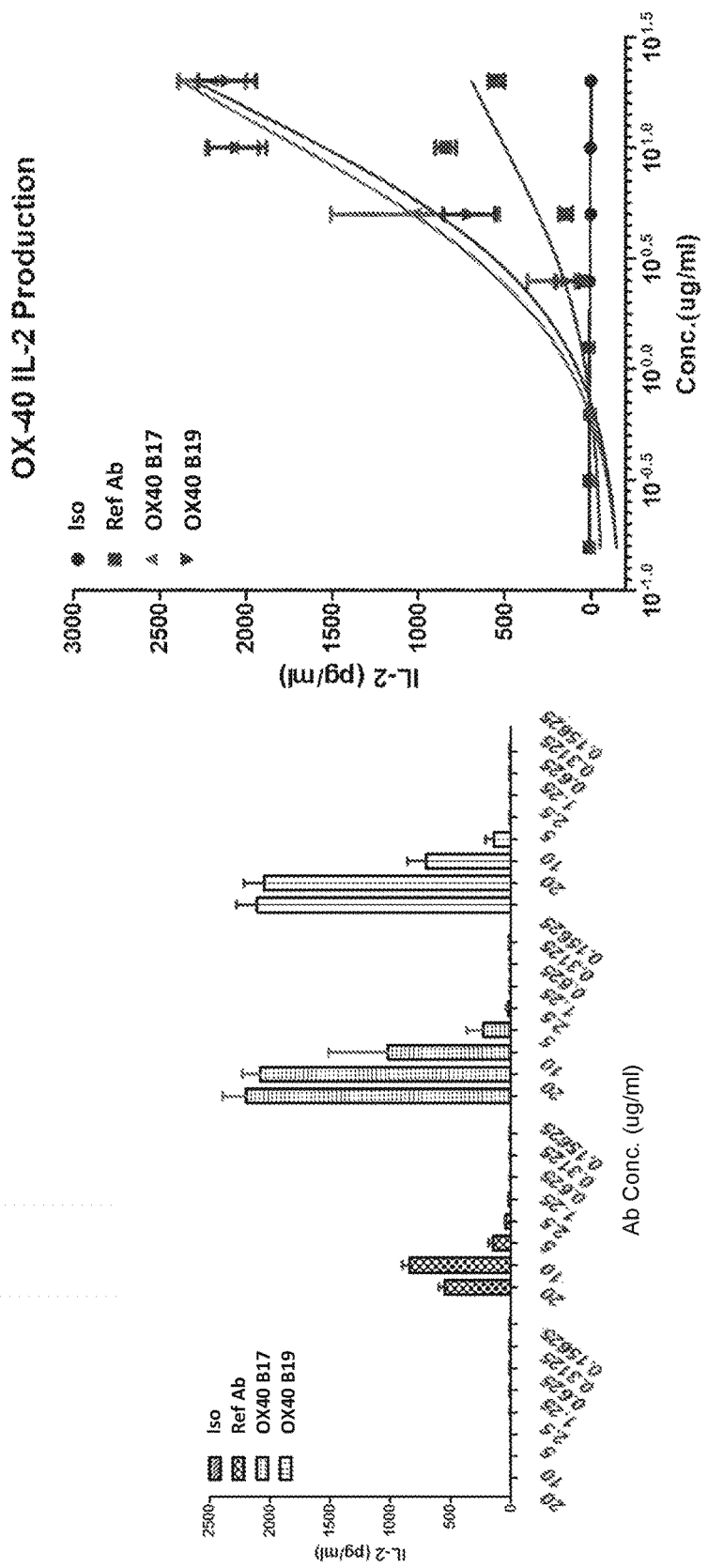
FIGS. 13A and 13B show the concentration of human IL-2 (FIG. 13A) and IFN-γ (FIG. 13B) present in cell culture media following 3 days of stimulation of human T cells with plate bound anti-CD3 and several concentrations of OX40 specific antibody leads.
Figure 13B:
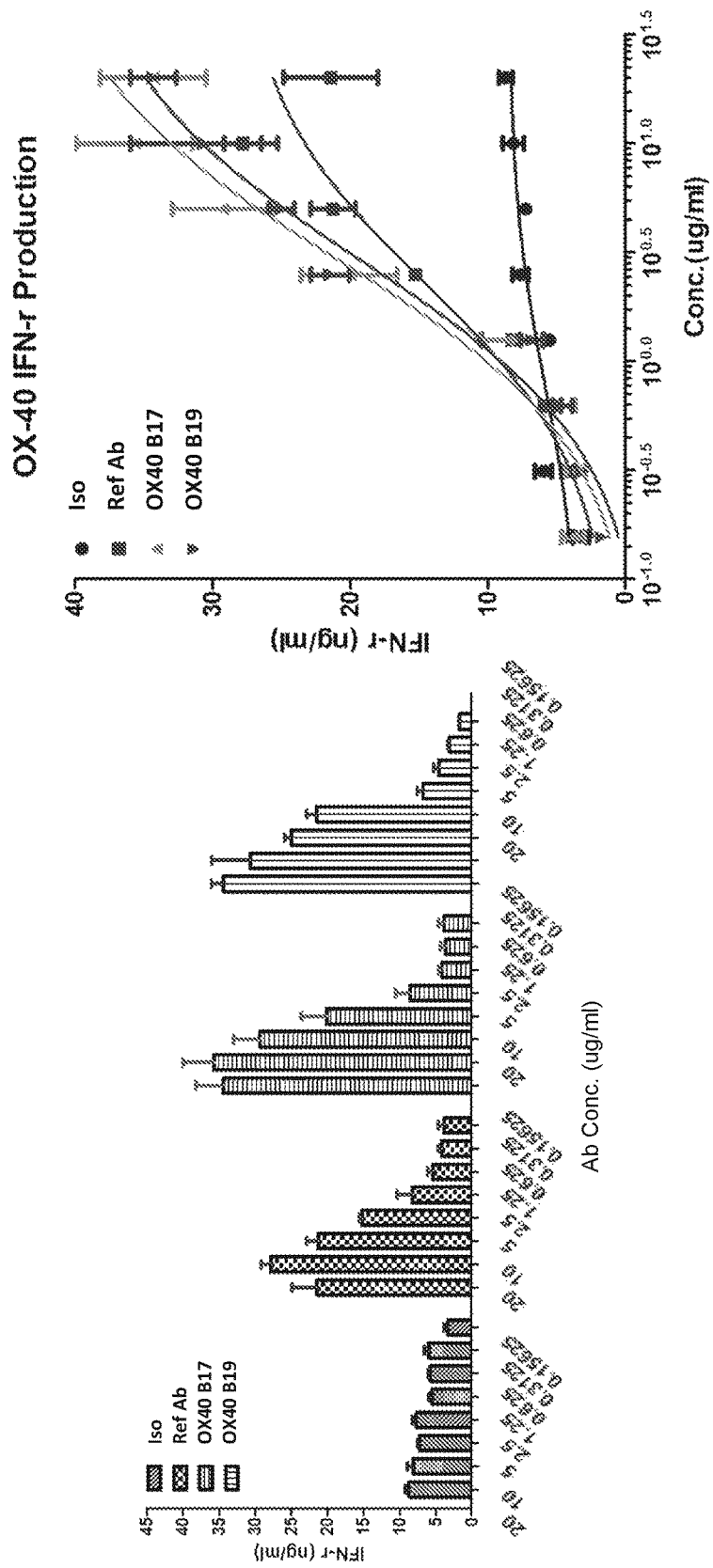

As the data shown in the FIGS. 13A and 13B, both anti-OX40 antibody leads, clones B17 and B19, were shown a better agonistic activity in the assay after anti-OX40 antibody leads (B17 or B19) 3 days treatment. Either IL-2 production or IFN-γ production shows an obvious enhancement upon antibody treatment and revealed does-dependent correlation. Higher cytokine productions were recorded in higher dose antibody treatment.

In order to evaluate the agonistic activity of OX40 antibody leads, B17 and B19, the EC50 were also determined as well as agonistic activity assay and cytokine production were recorded for comparison.

Construction, Expression and Purification of Anti-PD-L1-OX40 scFv Antibody

Figure 14:
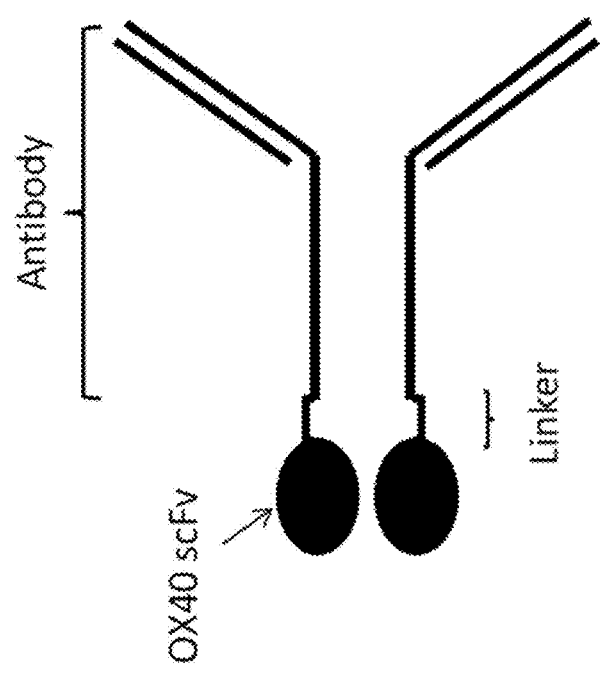
FIG. 14 shows the structure of an antibody heavy chain Fc fused with an OX40 specific scFv domain.

Since the bispecific is designed as IgG based fused with scFv format, the structure of anti-immune checkpoint antibody Fc-terminally fused with OX40 scFv. Antibody can be inhibitory anti-immune checkpoint antibodies, such as anti-PD-L1, anti-PD-1, anti-CTLA4, anti-LAG3, etc., or stimulatory antibodies, such as anti-CD28, anti-CD137, anti-CD27, anti-ICOS, etc. A linker is placed between antibody Fc and OX40 scFv to generate the bispecific antibody as depicted in FIG. 14.

Figure 15:
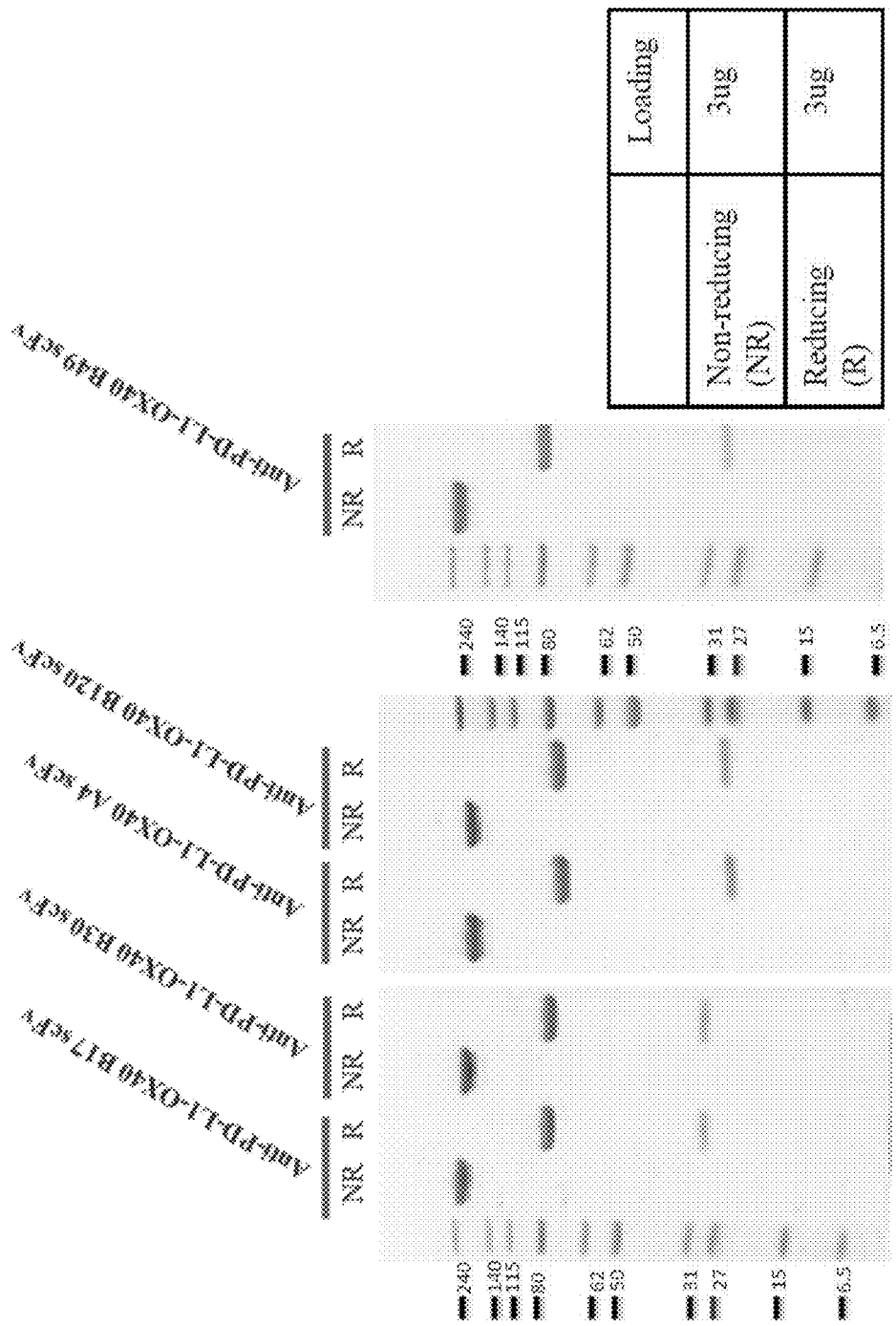
FIG. 15 shows examples of PAGE-gel analysis of anti-immune check point antibodies-human OX40 fusion proteins. Purified fusion proteins, anti-PD-L1-OX40 scFv fusion proteins were shown to have a molecular weight about 220 kDa (non-reducing), and heavy chain fusion has about 85 kDa and light chain is about 25 kDa (reduced) in both antibody fusions.

In some embodiment, the anti-PD-L1 antibody lead clone 6 is assigned to be IgG form, on the other hand, the anti-OX40 antibody lead would be transformed as scFv format to fuse at C-terminus of Fc region in anti-PD-L1 antibody lead clone 6. The transformation from antibody to scFv format could result in the reduction of the binding activity or specificity; therefore several anti-OX40 antibody leads were used to scFv transformation. Construction of bi-functional anti-PD-L1 antibody Fc fused with full-length OX40 scFv (SEQ ID NO: 10 as clone A4, SEQ ID NO: 11 as clone B17, SEQ ID NO: 12 as clone B19, or SEQ ID NO: 13 as clone B120). A short flexible peptide linker, $(GGGGS)_2$ (SEQ ID NO: 14) was placed between, for example, anti-PD-L1 antibody heavy chain C-terminus of Fc region and N-terminal module of OX40 scFv to ensure correct folding and minimize steric hindrance. The coding sequences of anti-PD-L1-OX40 scFv antibodies were shown in SEQ ID NO: 16 (anti-PD-L1-clone 6 heavy chain-OX40 clone B17 scFv) and NO: 17 (anti-PD-L1-clone 6 heavy chain-OX40 clone B19 scFv). The constructed antibody Fc fusion proteins were leaded by a signal peptide (SEQ ID NO: 15) and expressed by mammalian cells, and purified from the transfected cell culture supernatant via 1-step Protein G chromatography. As shown in FIG. 15, greater than 90% purity can be obtained in a single step purification process and shows that purified fusion proteins have correct molecular weight (Mw=220 kD).

Figure 16A:
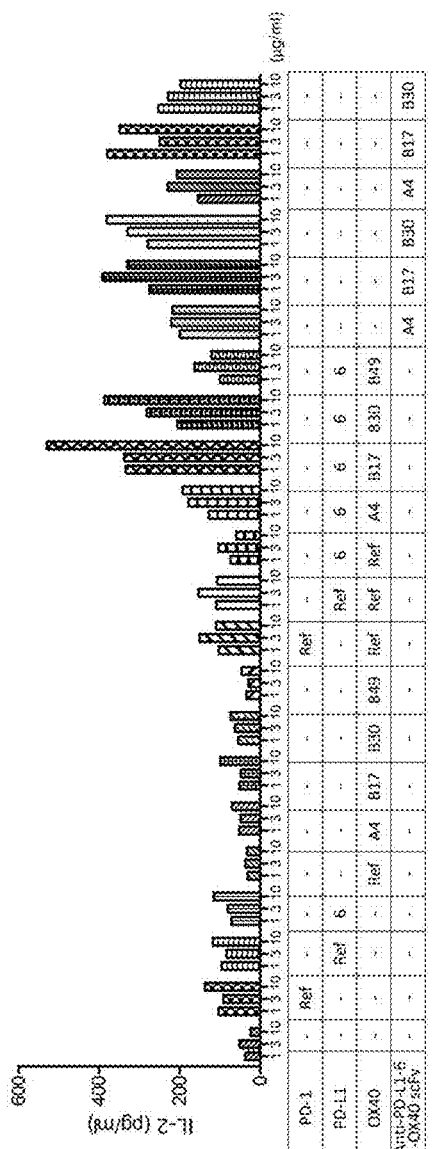
FIGS. 16A and 16B show bispecific antibody synergic stimulates T-cell activation for IL-2 and IFN-γ production in a mixed lymphocyte reaction (MLR) assay after 3 days (FIG. 16A) or 5 days (FIG. 16B) with mono-, combined or anti-PD-L1-OX40 scFv bispecific antibody treatment.
Figure 16A:
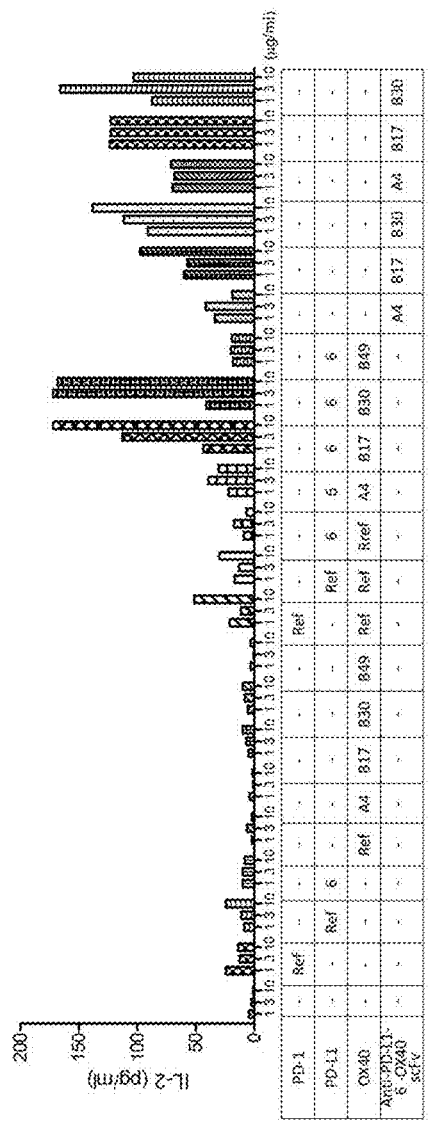
Figure 16B:
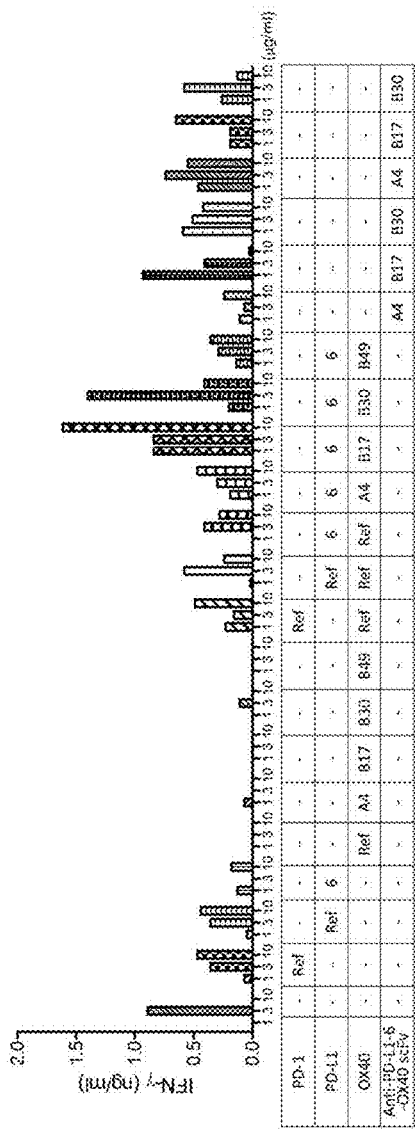
Figure 16B:
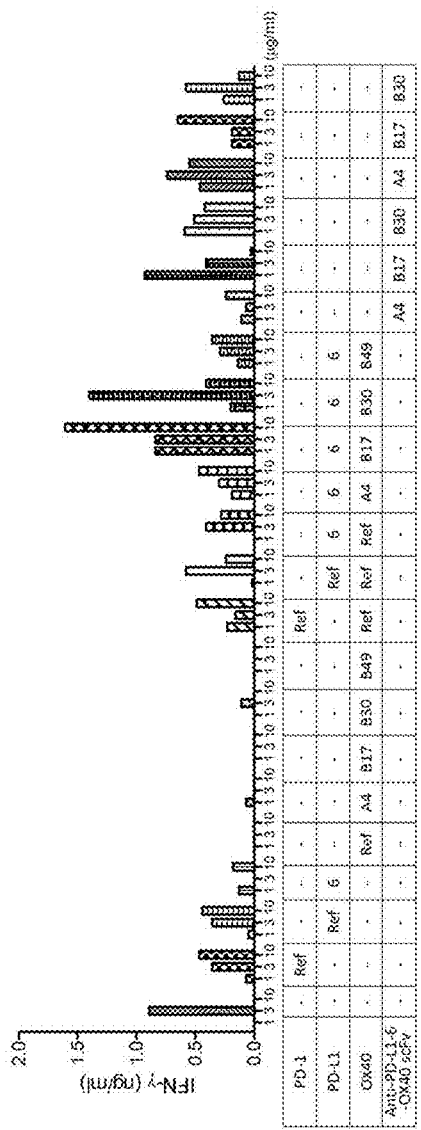

Enhanced Stimulation of T Cell Activation for Anti-PD-L1-OX40 scFv Bispecific Antibody Leads in MLRs To determine the synergic cooperation of bispecific antibody in enhancing T cells activation through inhibition the interaction between PD-1 and PD-L1 and agonistic activation of OX40 signaling, the bispecific antibody leads, anti-PD-L1-OX40 scFv, were applied into MLRs as described above. IL-2 and IFN-γ production were then recorded after 3 or 5 days antibody treatment. Mono-, combination or bispecific antibody was applied as equal amount or equal mole to compare the synergic effect in T cell activation enhancement and isotype IgG was used a negative control. As the data shown in the FIGS. 16A and 16B, the anti-PD-L1 antibody leads alone showed a significant IL-2 induction after 3 days treatment as well as reference antibody, MPDL3280A, on the contrary, the anti-OX40 antibody leads is unable to increase obviously upregulation of cytokine production, either after 3 days or 5 days antibody treatment. This is consisted with reference antibody, GSK3174998. However, combination of the anti-OX40 antibodies and anti-PD-L1 antibodies showed a significant upregulation of cytokine production after 3 and 5 days antibody treatment. The synergic effect is also observed in the bispecific antibody leads treatment and increment of cytokine production is similar as well as combination treatment. This indicated the anti-PD-L1-OX40 scFv bispecific antibody leads also function as well as antibody combination treatment without loss any binding activities in the scFv transformation.

Aggregation and Purity Determination of Bispecific Antibody

Since purified anti-PD-L1-clone 6-OX40 clone B17 scFv Ab revealed a lower purity (74.07%) by SEC-HPLC analysis after a single column protein A chromatography purification, therefore, several antibody variants were generated to improve the purity and reduce the aggregation for the bispecific antibody in the present invention. The linkers described as above were used to replace the linker in OX40 B17 scFv in the bispecific antibody, anti-PD-L1-OX40 Ab (SEQ ID NO: 16), and produced as anti-PD-L1-OX40 Ab-V1 to V4 (SEQ ID NO: 18 to SEQ ID NO: 21) in the CHO cells. Those variants were then purified and analyzed by XBridge Protein BEH SEC-HPLC column (Waters, Cat. No. 186007640). The data was summarized as below Table 1, one of the bispecific antibody variants, anti-PD-L1-OX40 Ab-V4 revealed a significant improvement of antibody purity. The purity is enhanced from 74.07 to 92.27%. Therefore, the anti-PD-L1-OX40 Ab-V4 was used to engineer further to improve the antibody purity.

TABLE 1

Different linkers in OX40 B17 scFv

| Abbreviation | Heavy chain/light chain | Linker in OX40 B17 scFv | Reference |
|---|---|---|---|
| Anti-PD-L1-OX40 Ab | Anti-PD-L1-6-OX40 B17 scFv-L1 HC/ Anti-PD-L1 6 LC | GGGGSGGGGSGGGGS (SEQ ID NO: 39) | Int. J. Mol. Sci. 2014, 15(12), 23658-23671 |
| Anti-PD-L1-OX40 Ab-V1 | Anti-PD-L1-6-OX40 B17 scFv-L2 HC/ Anti-PD-L1 6 LC | SSGGGGSGGGGGSS RSSL (SEQ ID NO: 40) | None |
| Anti-PD-L1-OX40 Ab-V2 | Anti-PD-L1-6-OX40 B17 scFv-L3 HC/ Anti-PD-L1 6 LC | GGKGSGGKGTGGKGS GGKGS (SEQ ID NO: 41) | Virol J. 2008; 5:21 |
| Anti-PD-L1-OX40 Ab-V3 | Anti-PD-L1-6-OX40 B17 scFv-L4 HC/ Anti-PD-L1 6 LC | GSASAPTLFPLVS (SEQ ID NO: 42) | DOI: 10.3892/mmr. 2013.1502 |
| Anti-PD-L1-OX40 Ab-V4 | Anti-PD-L1-6-OX40 B17 scFv-L5 HC/ Anti-PD-L1 6 LC | GSTSGSGKPGSGEGS TKG (SEQ ID NO: 43) | PMID: 8309948 |

For characterization the size distribution of bi-specific antibodies, samples were loaded onto XBridge Protein BEH SEC-HPLC column (Waters, Cat. No. 186007640) using a Waters Alliance 2695 Separations Module. Protein peak were detected at 280 nm using a Water 2996 PDA Detector. The mobile phase was isocratic 25 mM sodium phosphate (Sigma, Cat. No. 04272 and Cat. No. 04269) with 200 mM NaCl (AMRESCO, Cat. No. 0241), pH 6.8, at a flow rate of 0.4 mL/min. Peak percentages were determined by the portions of peak area as shown in FIGS. 17A to 17E.

Figure 17A:
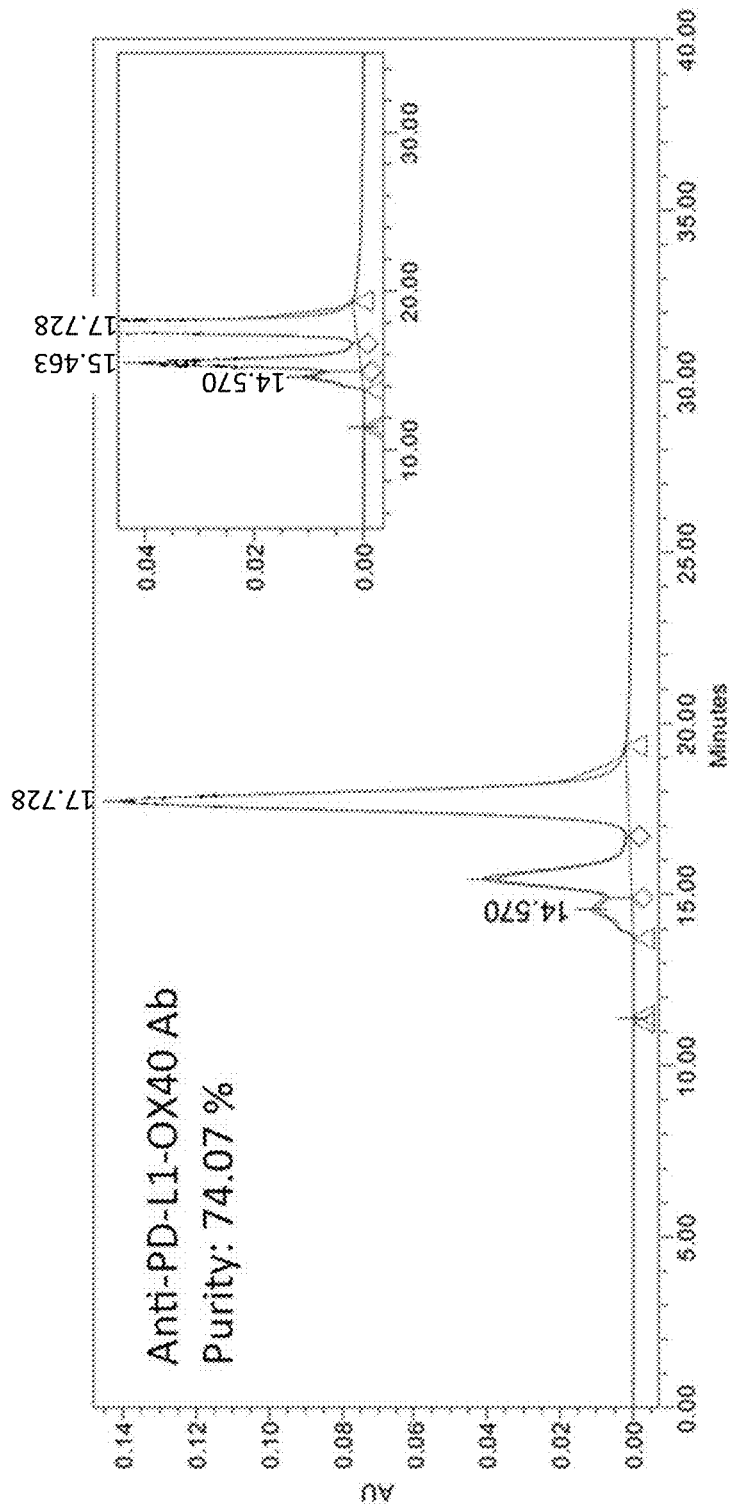
FIGS. 17A to 17E respectively show the aggregation and purity determination of Bi-specific antibodies, Anti-PD-L1-OX40 Ab and Anti-PD-L1-OX40 Ab-V1 to V4, with 5 different linkers in OX40 scFv.
Figure 17B:
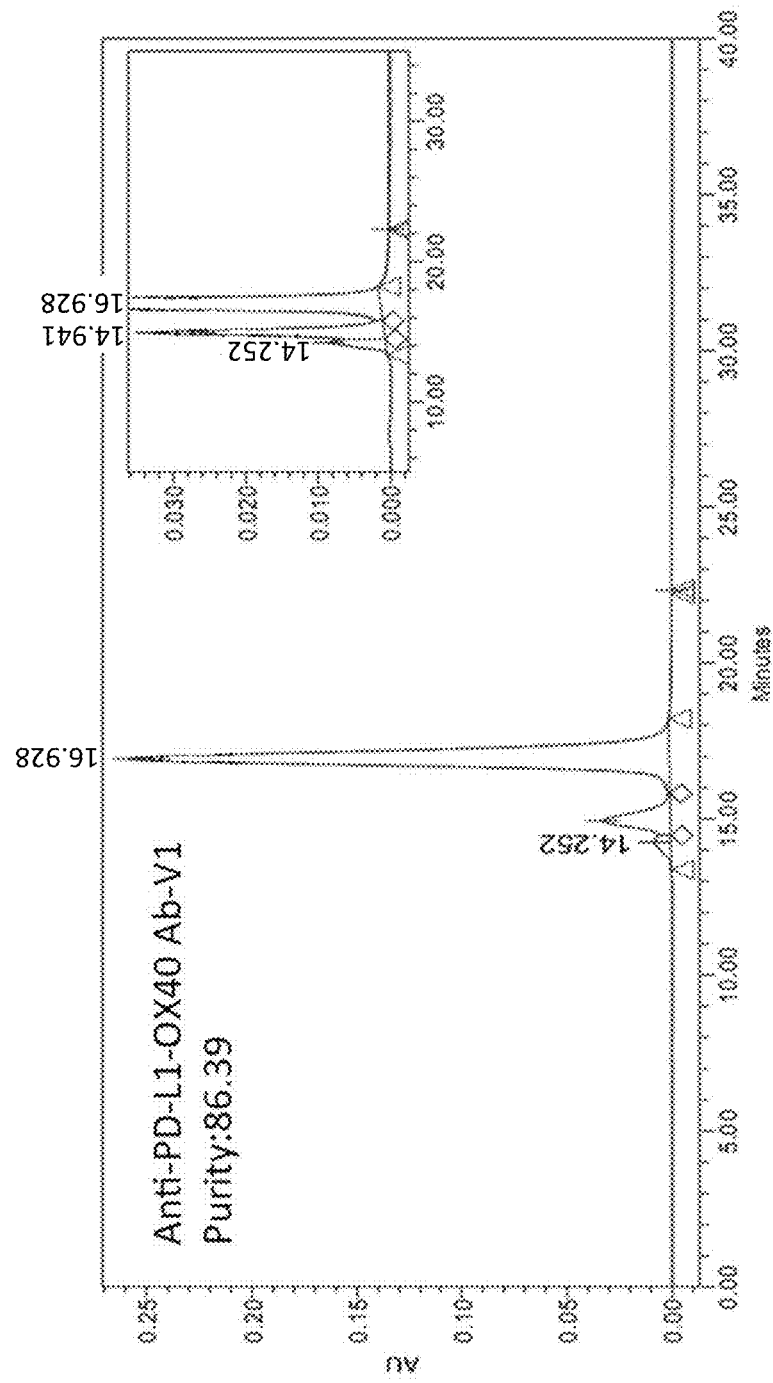
Figure 17C:
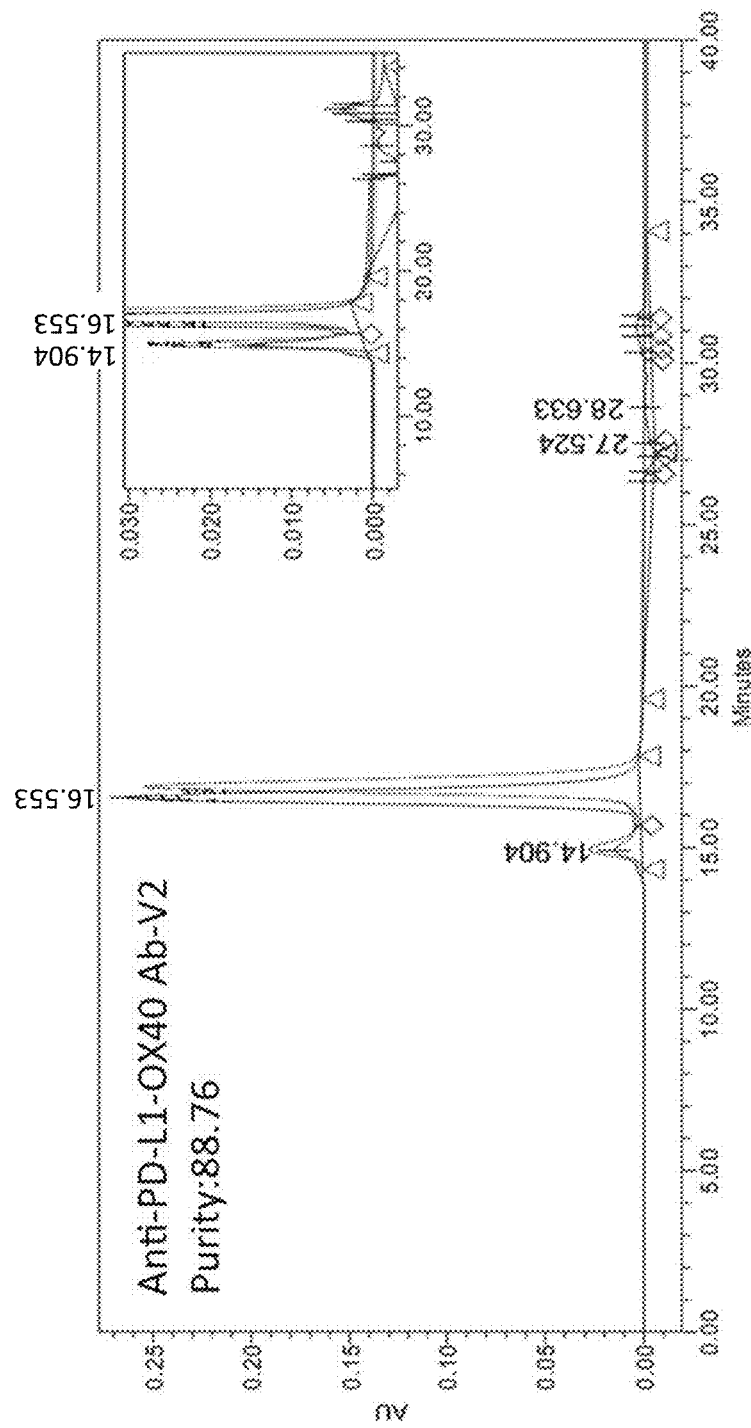
Figure 17D:
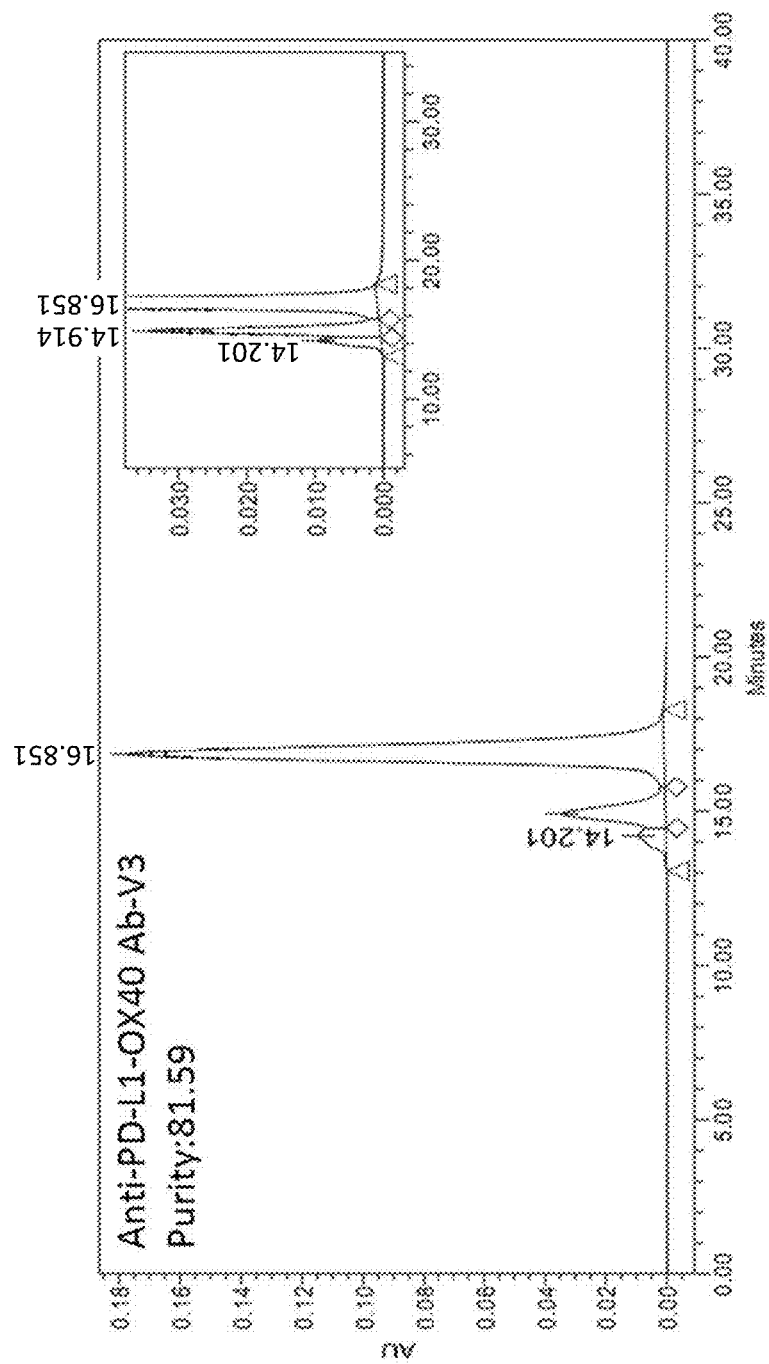
Figure 17E:
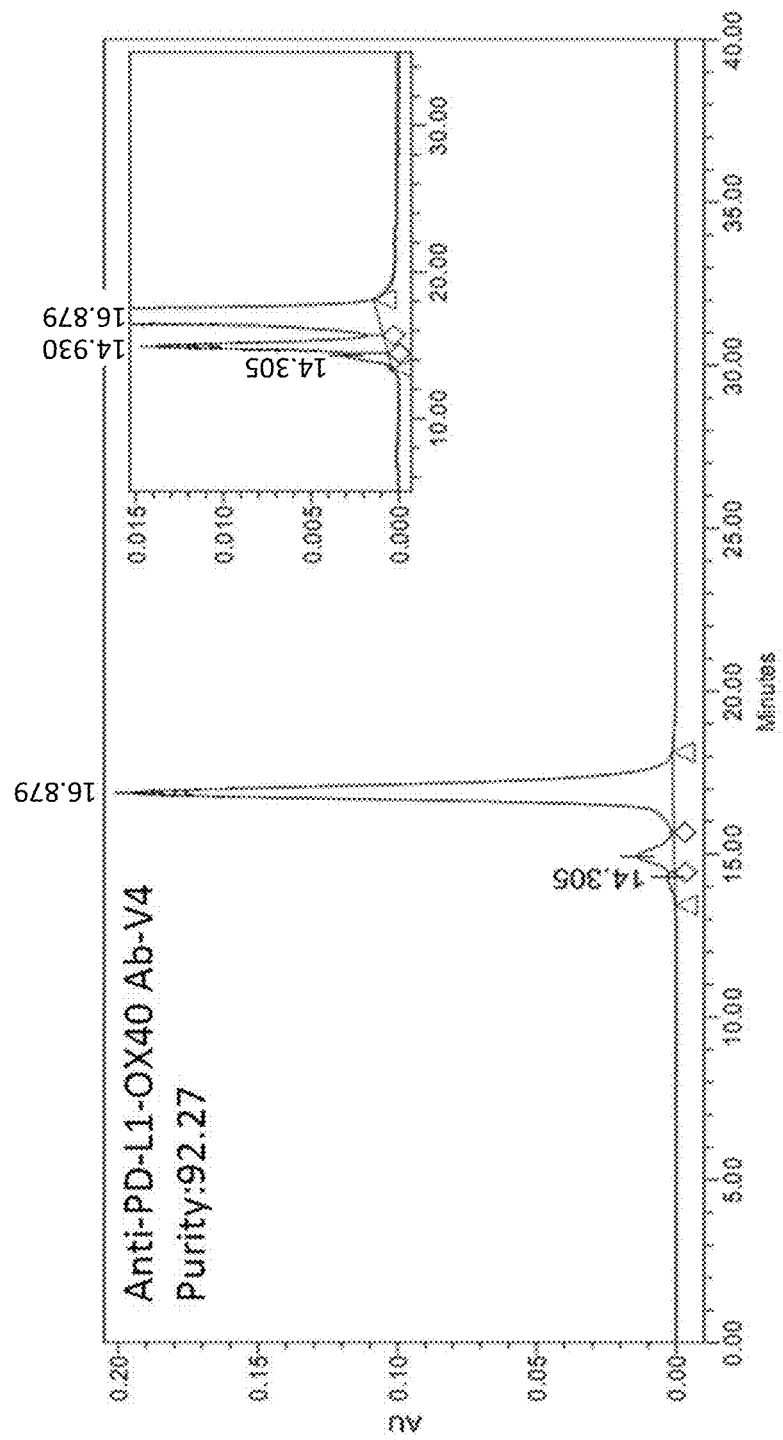
Figure 18:
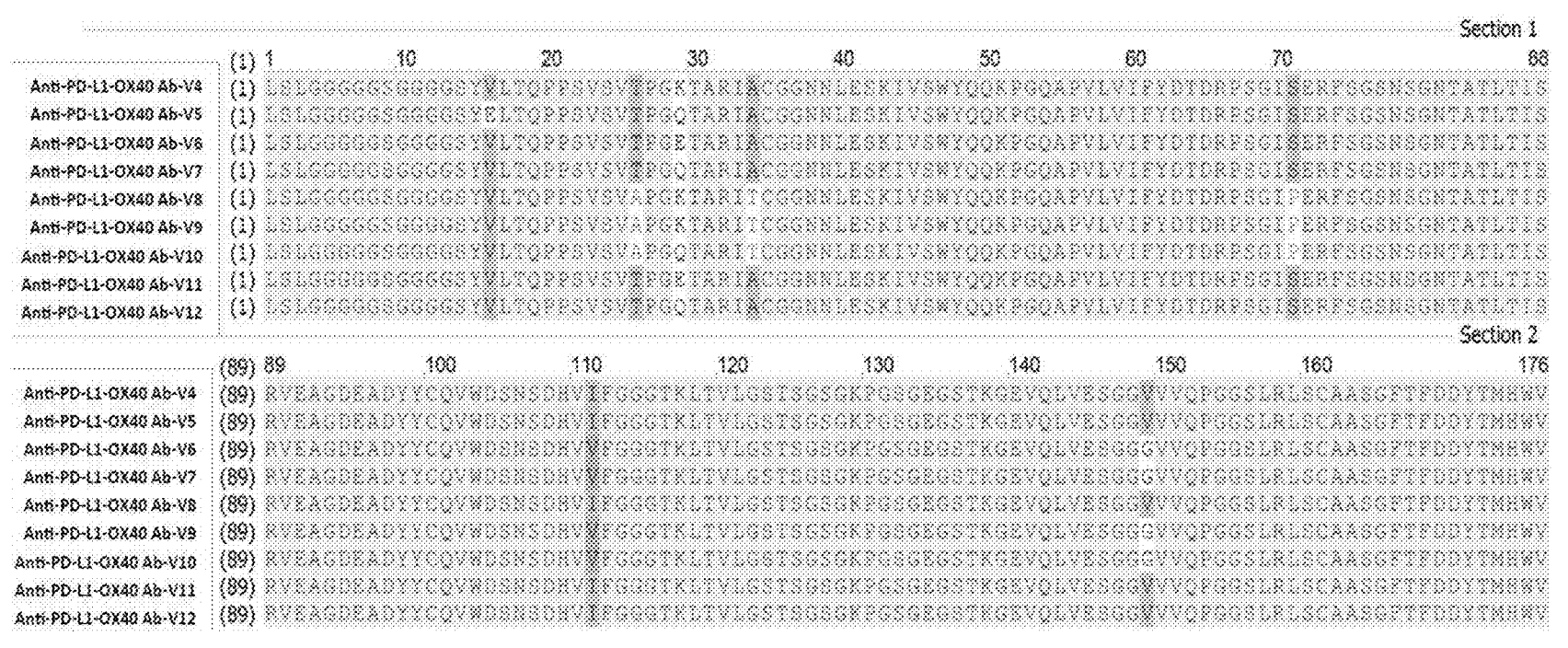
Figure 19:
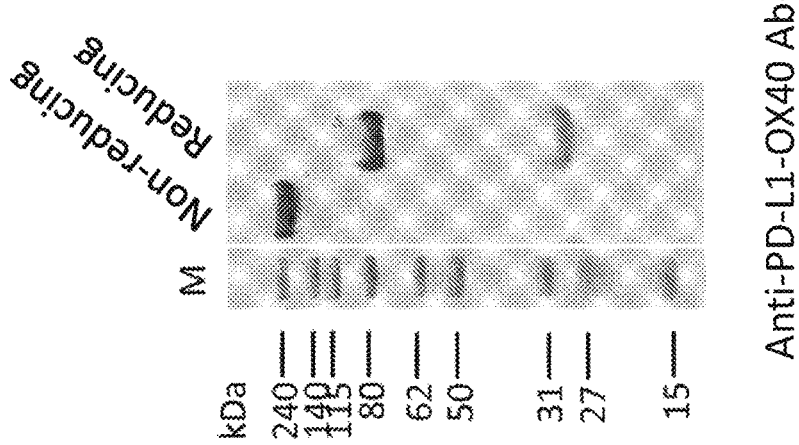
FIG. 19 shows examples of PAGE-gel analysis of anti-immune check point antibodies-human OX40 fusion proteins. Purified fusion proteins, anti-PD-L1-OX40 Ab-V5 fusion proteins were shown to have a molecular weight about 220 kDa (non-reducing), and heavy chain fusion has about 80 kDa and light chain is about 30 kDa (reduced) in both antibody fusions.

Anti-PD-L1-OX40 Ab-V4 revealed a significant purity improvement (FIG. 17E). The bispecific antibody was engineered further in the OX40 B17 scFv fragment to improve purity again. Several residues in the OX40 B17 scFv showed in FIG. 18 were substituted with difference amino acid and heavy chain variants were pairing with anti-PD-L1 clone 6 light chain to generate several bispecific antibody variants, from anti-PD-L1-OX40 Ab-V5 to V12 (SEQ ID NO: 22 to SEQ ID NO: 29), and then expressed and purified as mentioned above. The purity of bispecific antibody variants were summarized as below Table 2, the anti-PD-L1-OX40 scFv-V5 revealed the best purity in those antibody variants. The purity is aroused up to 96.46%. This is shown a superior purity for the engineered bispecific antibody and also revealed a good development ability for this bispecific antibody in the future. As shown in FIG. 19, the integrity of anti-PD-L1-OX40 Ab-V5 was also analyzed by SDS-PAGE and shown a good integrity under reducing and non-reducing condition.

TABLE 2

Purity of Antibody

| Antibody | Purity by SEC-HPLC (%) |
|---|---|
| Anti-PD-L1-OX40 Ab-V4 | 92.27 |
| Anti-PD-L1-OX40 Ab-V5 | 96.46 |
| Anti-PD-L1-OX40 Ab-V6 | 86.36 |
| Anti-PD-L1-OX40 Ab-V7 | 88.04 |
| Anti-PD-L1-OX40 Ab-V8 | 90.00 |
| Anti-PD-L1-OX40 Ab-V9 | 87.89 |
| Anti-PD-L1-OX40 Ab-V10 | 86.56 |
| Anti-PD-L1-OX40 Ab-V11 | 86.61 |
| Anti-PD-L1-OX40 Ab-V12 | 84.78 |

Figure 20:
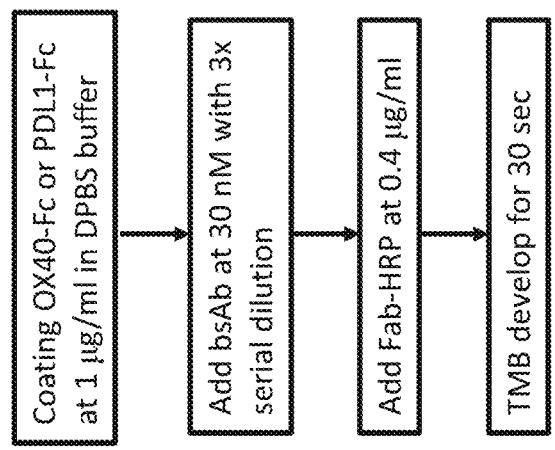
FIG. 20 shows a flow chart illustrating the ELISA method for binding activity evaluation of bispecific antibody variants.
Figure 21:
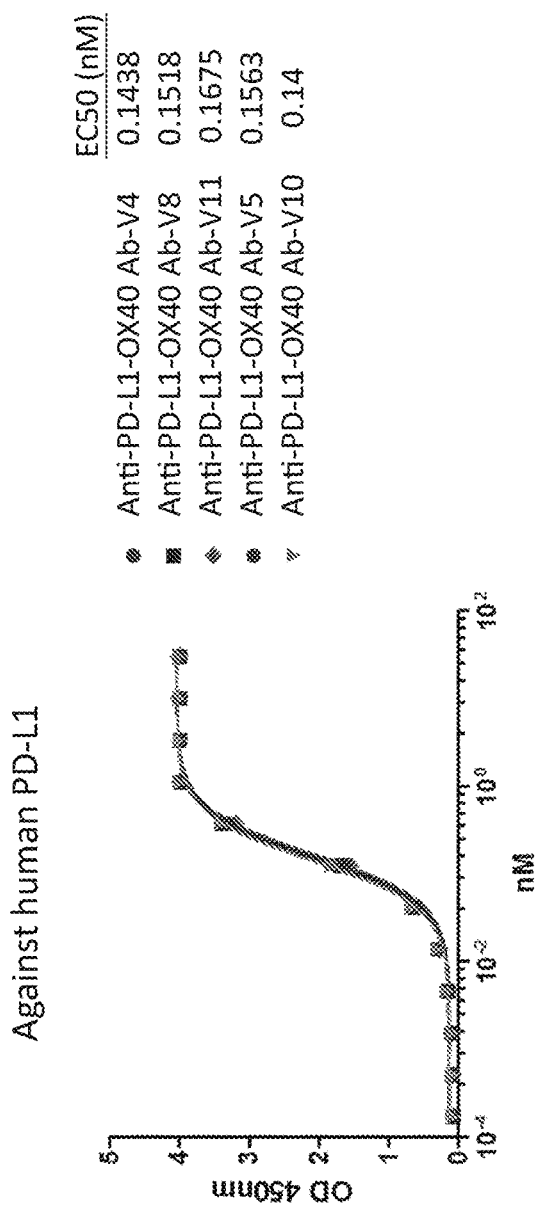
FIG. 21 shows the human PD-L1 binding activity of the bispecific antibody variants and its EC50.
Figure 22:
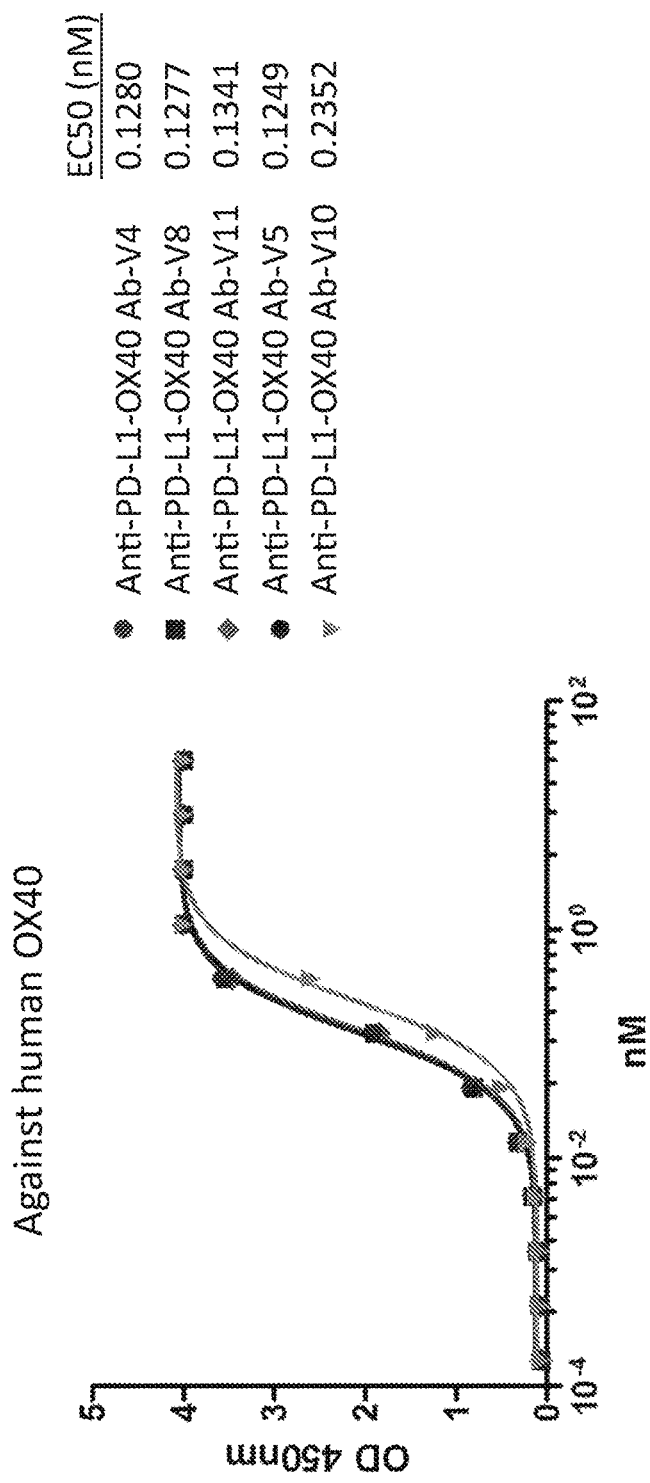
FIG. 22 shows the human OX40 binding activity of the bispecific antibody variants and its EC50.

Meanwhile, the engineered bispecific antibody variants were also applied for binding activity evaluation for human PD-L1 and OX40 by direct ELISA as shown in FIG. 20. All bispecific antibody variants as indicated showed the same binding activity for human PD-L1 (FIG. 21), this binding activity is similar with anti-PD-L1 6 antibody. This phenomenon was also observed in the human OX40 binding assay (FIG. 22). Only anti-PD-L1-OX40 Ab-V10 showed a weaker binding activity for human OX40 as comparing with other variants. It indicated the engineering of OX40 scFv is not affected the OX40 binding activity. The binding activity is retained either for PD-L1 or OX40. Since the anti-PD-L1-OX40 Ab-V5 revealed a superior antibody purity and binding activity for PD-L1 and OX40, so the anti-PD-L1-OX40 Ab-V5 was chosen for serum stability.

Ex Vivo Serum Stability

The stability was assessed in human serum (BioreclamationIVT, Cat. No. HMSRM) as well as serum from relevant preclinical species: rhesus monkey (BioreclamationIVT, Cat. No. RHSSRM), and CD1 mouse (BioreclamationIVT, Cat. No. MSESRM). Samples were added into different species serum for a final concentration of 15 µg/mL and incubated at 37° C. water bath. Serum samples were collected after incubation times of 0, 1, 2, 3, 7, 10 and 14 day and stored frozen at −80° C. until analysis.

Quantitation Sandwich ELISA

OX40-Fc was coated into ELISA plate (NUNC, Cat. No. 442404) with 100 UL at 1 µg/mL in PBS and incubated for overnight at 4° C. Wash buffer was prepared as PBS with 0.1% Tween-20 (Sigma, Cat. No. P2287-500 mL) and blocking buffer was prepared as 1% BSA (UniRegion, Cat. No. UR-BSA001-100G) in wash buffer. Serum samples were prepared with 10-fold dilution with 3× serial dilution in blocking buffer and the standards were prepared at 10 nM with 3× serial dilution in blocking buffer. Biotinylated PD-L1-Fc was labeled with Biotin Fast conjugation Kit (abcam, Cat. No. ab201796) using standard protocol and prepared at 30 nM in blocking buffer. Streptavidin-HRP (abcam, Cat. No. ab7403) was prepared at 1 µg/mL in blocking buffer. All the samples were added into each well for 100 µL after plates washed 3 times with wash buffer and incubated for 1 hour at ambient temperature. TMB development with 100 µL TMB solution (Invitrogen, Cat. No. 00-2023) for 2 min and stopped with 100 µL 1N HCl solution (Merck, Cat. No. 1.00317.1000). O.D. 450 nm absorption was read by ELISA reader (Biotek, Powerwave XS).

Figure 23:
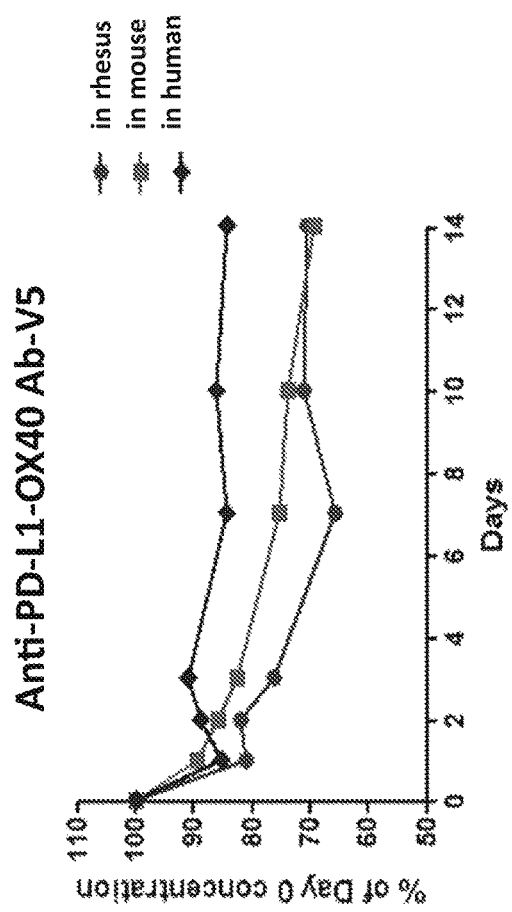
FIG. 23 shows the ex vivo serum stability of bispecific antibody variant, anti-PD-L1-OX40 Ab-V5.

Anti-PD-L1-OX40 Ab-V5 was chosen for ex vivo serum stability because of its superior purity and binding activity for PD-L1 and OX40. The purified bispecific antibodies were mixed with serum from different species, such as human, mouse or monkey. After several days culture, the samples were took and analyzed by sandwich ELISA to determine the antibody amount. As shown in FIG. 23, the anti-PD-L1-OX40 Ab-V5 still showed a good serum stability after 14 days culture at 37° C. The concentration of the antibody is still above 70% either in human, mouse or monkey. It is indicated the antibody also have a good serum stability.

Figure 24A:
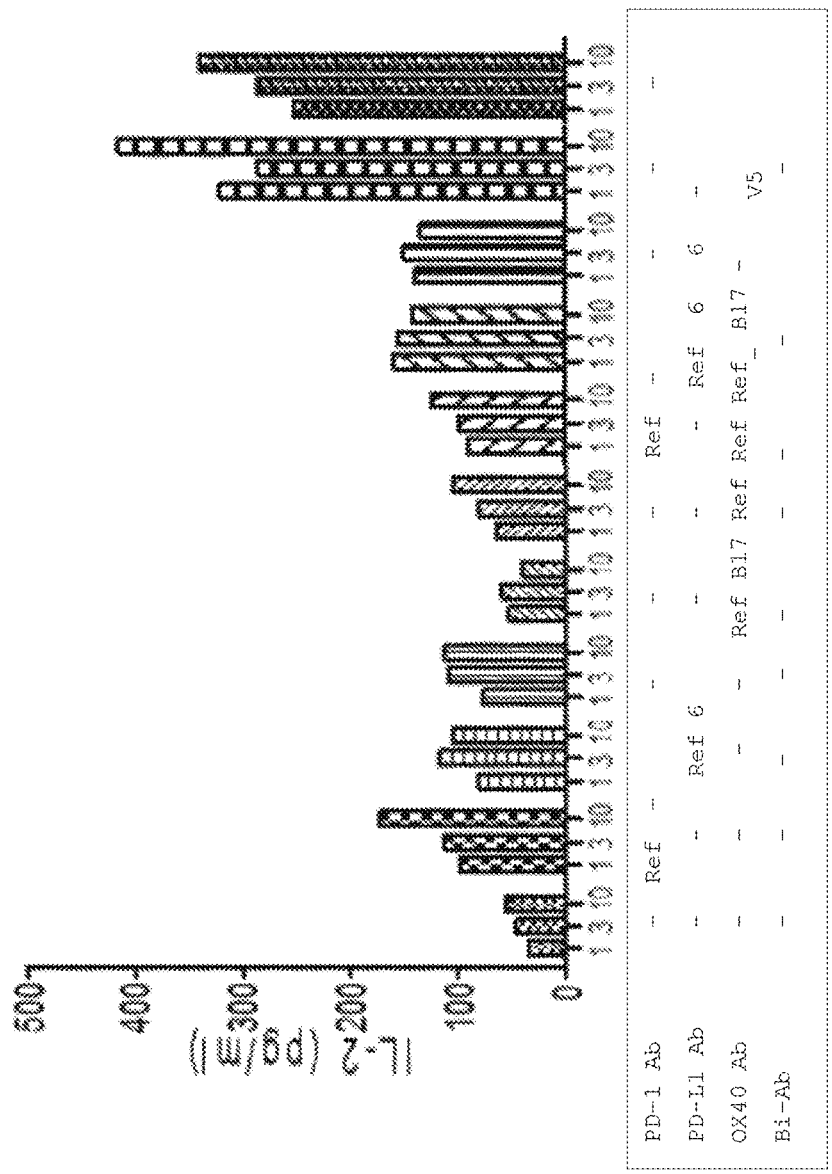
FIGS. 24A and 24B show the IL-2 production for 3 days (FIG. 24A) and IFN-γ production for 5 days (FIG. 24B) after modulating T cell with mono-, combined or anti-PD-L1-OX40 Ab-V5 bispecific antibody treatment.
Figure 24B:
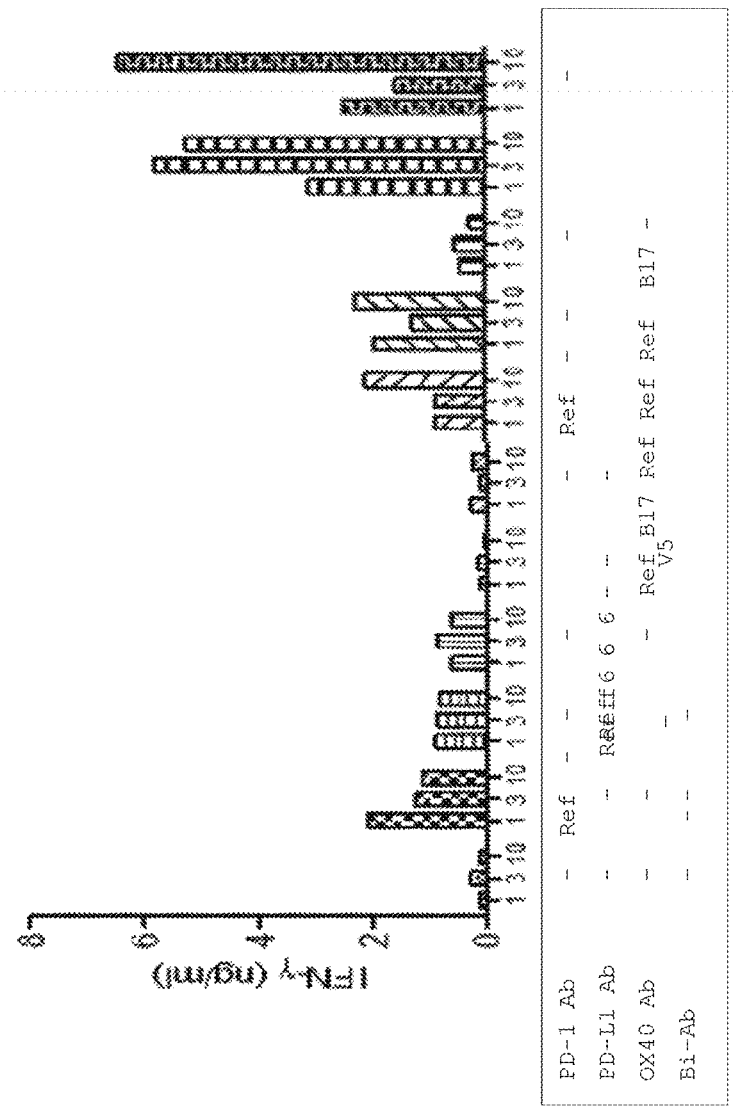

To measure the ability of the anti-PD-L1-OX40 Ab-V5 to modulate T cell responsiveness purified T cells will be cultured with allogeneic dendritic cells, prepared by culturing monocytes in GM-CSF and IL-4 for few days. Parallel plates were set up to allow collection of supernatants at day 3 and day 5 to measure IL-2 and IFN-γ respectively using a commercial ELISA kit. As the data shown in FIGS. 24A and 24B, the IL-2 and IFN-γ production are highly upregulated in the bispecific antibody treatment (V5) as well as combination treatment after 3 or 5 days antibody treatment. Also, the enhancement is obviously superior than the anti-PD-L1 Ab or anti-OX40 Ab treatment alone. This implicated the engineered bispecific antibody, V5, still possess the agonistic activity as well as combination treatment without functionality lost and could be developed as a therapeutic antibody for various solid tumor or cancer in the future.

Anti-Tumor Activity of Bispecific Antibody (In Vivo Model)

The lack of rodent cross reactivity of the PD-L1 and OX40 in bispecific antibodies prevented the use of standard murine syngeneic or human xenograft tumor models for the assessment of anti-human tumor efficacy of the antibodies. Accordingly, a novel huPBL-SCID-Bg xenogeneic tumor mouse model was generated using a SCID-Bg mouse (CB.17/Icr.Cg Pkrd$^{cscid}$Lyst$^{bg}$/Crl), which harbors the beige (Bg) mutation lack murine T and B lymphocytes and functional NK cells. The anti-human tumor efficacy of the bispecific antibodies was assessed using this model as described below.

The PC-3 human prostate was obtained from American Type Culture Collection and was cultured in RPMI-1640

(Invitrogen) with L-glutamine, sodium pyruvate, penicillin/streptomycin, and 10% heat inactivated fetal bovine serum (FBS, Gibco Cat. No. 10437). Cells were grown to confluency in T-150 Falcon flasks. Subsequently, cells were trypsinized (Trypsin 0.25%-EDTA; Invitrogen) and growth was scaled up to sufficient cell number for inoculation. Peripheral blood lymphocytes (PBMCs) were isolated from heparinized blood using Lymphoprep™ in accordance with the manufactures' protocol (STEMCELL Technologies Inc.). Counted cell suspensions were combine such that each mouse received an injection of $0.75 \times 10^6$ PBMCs and $3 \times 10^6$ tumor cells in a single bolus injection of 0.1 mL in PBS. In order to facilitate the tumor cells grown in the mouse, another 0.1 mL matrigel was then mixed with the combined cell suspension and then immediately injected into prepare mice.

Figure 25:
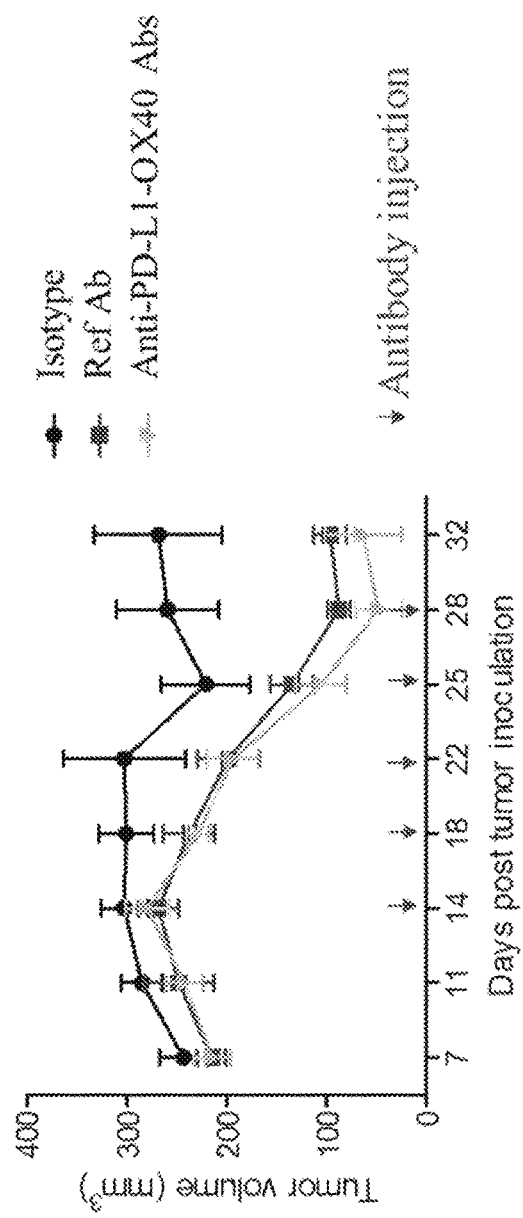
FIG. 25 is a graph showing the effect of anti-PD-L1-OX40 Ab-V5 bispecific antibody treatment and monoclonal antibody treatment on the growth of PC-3 tumor in Fox Chase SCID® Beige mice.

For each mouse, 0.2 mL volume of the combined cell suspension was injected subcutaneously into the right flank of the animal. After 14 days inoculation, the solid tumor is formed and reached around 250 to 300 mm³ and the bispecific antibody (3 mg/kg of Anti-PD-L1-OX40 Ab-V5), PD-L1 reference antibody (Ref Ab, MPDL3280A) or control antibody (Isotype) is challenged twice per week for three weeks with intraperitoneal injection (i.p.). Tumor measurement was made via Pressier caliper twice per week as well as test sample administration for the duration of the experiments and body weights were also recorded. Tumor volume was calculated using the following calculation: length×width²×0.44=volume (mm³) and plotted in the FIG. 25. Mice were removed from the study in the event that the tumor volume reached 2000 mm³ or animal lost 20% of body weight before termination of the experiment. Similar results were observed when tumors were measured on day 7 post inoculation, and the animals were randomized according to tumor volume. For animal study, each group contained 6 mice. As the data shown in the FIG. 25, the bispecific antibody showed a significant anti-tumor efficiency in PC-3 xenografted mouse model. The tumor size is shirked at 18 days post tumor inoculation as well as PD-L1 reference antibody and continued to reduce below 100 mm³. The PC-3 xenografted mouse model is preliminary demonstrated the anti-tumor of bispecific antibody and revealed its potential to be a therapeutic drug lead in the future.

Collectively, these results indicated bi-specific antibody sustain its immune checkpoint blocking in PD-1/PD-L1 signaling and agonistic activity for OX40 signaling. Studies are ongoing to further investigate the biological activity of these proteins using proper animal model, such as PC-3 tumor in humanized NOD.Cg-Prkde$^{scid}$ Il2rg$^{tm1wjl}$/SzJ (NSG) model.

The Fc region in the present invention could be from any immunoglobulin isotypes, subclasses, allotypes, or engineered mutants, such as knob and hole Fc fragment(s).

EXAMPLES

The example below describe the generation of monoclonal antibodies suitable for therapeutic purpose targeting human PD-L1 and OX40. Composite, human anti-human PD-L1 and anti-OX40 antibodies were generated from anti-PD-L1 antibody clone 6 and anti-OX40 antibody clone B17, respectively. Segments of human V region sequence were sourced from unrelated human antibody (germline and non-germline) sequence databases.

Example 1 Generation of IgG Antibodies that Bind to PD-L1 and OX40

Certain antibodies provided by present invention were originally generated from Fabs bind to human PD-L1 or OX40. The Fabs were selected from a phage display library, the OmniMab phagemid library, following alternating panning on corresponding Fc fusion proteins (PD-L1-Fc or OX40-Fc) and cells expressing human corresponding protein (PD-L1 or OX40). After direct ELISA or cell-based ELISA screening, the positive clones were then sequenced for heavy chain and light chain. These Fabs included those that are designated as "OM-PD-L1-6", and "OM-PDL1-32" etc. for PD-L1; "OM-OX40-A4", "OM-OX40-B17", and "OM-OX40-B19" etc. for OX40. PD-L1 antibodies PD-L1-Clone 3, PD-L1-Clone 6, and PD-L1-Clone 32 disclosed in this application were generated from "OM-PD-L1-6" and "OM-PDL1-32". Meanwhile, OX40 antibodies OX40-A4, OX40-B17, and OX40-B19 disclosed in this application were generated from "OM-OX40-A4", "OM-OX40-B17", and "OM-OX40-B19" in HEK293 cell or CHO-S cells. And bispecific antibody targeting PD-L1 and OX40 simultaneously was designed as anti-PD-L1 6-OX40 scFv B17 antibody and anti-PD-L1 6-OX40 scFv B19 antibody. The amino acid sequence of the light chain variable region and heavy chain variable region of a given Fab are identical to the amino acid sequence of the light chain variable region and heavy chain variable region, respectively.

Example 2 In Vitro Binding of Anti-PD-L1-OX40 scFv to its Corresponding Target Anti-PD-L1-OX40 bispecific antibody was constructed as shown in the FIG. 14 and expressed in the HEK293 cells or CHO-S cell. The medium containing bispecific antibody was affinity purified from culture supernatant by Protein G chromatography. Purified antibody is then concentrated, followed by dialysis in PBS buffer and analyzed by SDS-PAGE as shown in the FIG. 15. To test direct binding of purified fusion proteins to PD-L1 or OX40 on ELISA, 100 ng/well recombinant PD-L1 or OX40 was coated in a 96-well ELISA plate. Various concentrations of purified anti-PD-L1-OX40 scFv were then added to each well and incubated for 1 hr. After washing, 1:5000 dilution of anti-Fab HRP conjugate (Jackson Immunochemicals) was added to each well and incubated for another hour. After final washing, TMB substrate (Invitrogen Inc.) was added and OD absorbance at 450 nm was measured. The data analyzed by sigmoidal curve fitting using GraphPad Prism 5 and EC50 is calculated.

Example 3 Antigen Binding Specificity of Anti-PD-L1-OX40 scFv by FACS Analysis To test anti-PD-L1-OX40 scFv antibody binding specificity, stable PD-L1 expression 293 cells, IFN-γ stimulated A549 or WiDr were stained with 1 µg/mL anti-PD-L1-OX40 scFv antibody for 1 hr on ice before wash three times with 1×PBS. The bound antibody fusion proteins were detected with Alexa-488 conjugated goat anti-human IgG (H+L) followed by FACS analysis. Isotype antibody was used as negative control for the test. Results showed anti-PD-L1-OX40 scFv sustains its antigen binding specificity as compared with anti-PD-L1 alone. The binding specificity of anti-PD-L1-OX40 scFv antibody was also tested using stable OX40 expression 293 cells.

Example 4 In Vitro Immunomodulatory Effect of Bi-Functional Proteins

To measure the ability of the anti-PD-L1-OX40 scFv antibodies to modulate T cell responsiveness purified T cells will be cultured with allogeneic dendritic cells, prepared by culturing monocytes in GM-CSF and IL-4 for few days. Parallel plates were set up to allow collection of supernatants at day 3 and day 5 to measure IL-2 and IFN-γ respectively using a commercial ELISA kit. Genentech/Roche's humanized anti-PD-L1, MPDL3280A will be produced in-house and used as positive control. As the data shown in the FIGS. 16A and 16B, the IL-2 and IFN-γ production are highly upregulated in the bispecific antibody treatment as well as combination treatment after 3 or 5 days antibody treatment. Especially, the bispecific antibody composited by anti-PD-L1 antibody clone 6 and anti-OX40 antibody clone B17 (anti-PD-L1-OX40 scFv B17 Ab) or combination (anti-PD-L1 clone 6 Ab plus anti-OX40 clone B17 Ab) showed the enhancement of T cells activation is higher than the combination of PD-L1 and OX40 reference (PD-L1 Ref Ab plus OX40 Ref Ab). This indicated the anti-OX40 B17 antibody may possess a special epitope binding to result in a better agonistic activity as comparing with reference OX40 antibody, GSK3174998.

Example 5 Human Leukocyte Expansion Induced by Bispecific Antibodies In Vivo

The lack of detectable cross-reactivity of the PD-L1 or OX40 antibodies with murine PD-L1 or OX40 and the requirement for the presence of human immune cells required the development of models for the in vivo functional assessment of the bispecific antibodies. Mice with the NOD genetic background carrying the severe combined immunodeficient (SCID) mutation and deficiency in the IL-2 receptor common gamma chain (commonly termed NSG) are able to support the engraftment of large number of human peripheral blood leukocytes (huPBL) and maintain engraftment for at least 30 days (King et al., 2008). This mouse model, also known as huPBL-NSG model, was used to assess the functional effect of in vivo systemic administration of the antibodies on human immune cells.

Specifically, 6 million freshly isolated human PBMCs were adoptively transferred via intravenous injection into huPBL-NSG mice. Nine days post PBMC injections, the animals were administered a single 1 mg/kg dose of monoantibody, bispecific antibody or IgG4 isotype control antibody via intraperitoneal injection. At day 24 to 28 post PBMC engraftment, PBMC were stained with antibodies to human and murine CD45 assessed via flow cytometry. Forward and side scatter profiles were used to determine a lymphocyte gate. Bispecific antibodies were able to enhance expansion of human leukocytes as evidenced by increased proportion of human CD45+ cells in the peripheral blood of engrafted mice. For each group, n≥6 mice.

Example 6 Inhibition of PC-3 or A498 Tumor Cell Growth in huPBL-NSG by Anti-PD-L1-OX40 scFv Antibody PD-L1 positive human prostate cancer cell line, PC-3 (ATCC #CRL-1435) or kidney cancer cell line, A498 (ATCC® HTB-44™) can be used to establish xenograft models in huPBL-NSG mice. For tumor formation, $3 \times 10^6$ PC-3 cells (or A498 cells)/mouse will be injected subcutaneously in huPBL-NSG mice as described above. In order to assess the inhibitory effects on the tumor growth, different concentrations of anti-PD-L1-OX40 scFv antibody, reference antibody, or isotype antibody from 0.1-3 mg/kg will be administered intravenously twice weekly for 4 weeks in the mice after 14 days tumor cells implantation. The tumor growth will be measured twice per week up to 5 weeks as described in the Fox Chase SCID® Beige mice model.

Example 7 Pharmacokinetic Assessment of Anti-PD-L1-OX40 scFv in Mice and Monkeys 10-40 mg/kg of bi-functional proteins, anti-PD-L1-OX40 scFv will be administered into mice or monkeys via subcutaneous injection or intravenous injection. Serum samples will be taken at different time points after the injection up to 15 days. Concentrations of the Fc fusion protein in the serum samples will be determined using a sandwiched ELISA assay.

Although the present invention has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims.

What is claimed is:

1. An antibody or an antigen-binding portion thereof binding to OX40 (CD134), comprising:
a heavy chain variable region and a light chain variable region respectively comprising an amino acid sequence of:
amino acid 128-246 of SEQ ID NO: 10 and amino acid 1-112 of SEQ ID NO: 10.

2. The antibody or the antigen-binding portion thereof of claim 1, wherein the antibody or the antigen-binding portion thereof is a single chain variable fragment (scFv), wherein the sequence of the scFv is SEQ ID NO: 10.

3. The antibody or the antigen-binding portion thereof of claim 1, wherein the antibody or the antigen-binding portion thereof is a bispecific antibody.

4. The antibody or the antigen-binding portion thereof of claim 3, wherein the bispecific antibody comprises an immune checkpoint protein binding site.

5. The antibody or the antigen-binding portion thereof of claim 4, wherein the immune checkpoint protein binding site comprises a programmed cell death protein 1 ligand (PD-L1) binding site, PD-1 binding site, cytotoxic T-lymphocyte-associated antigen 4 (CTLA-4) binding site, or lymphocyte activation gene 3 (LAG3) binding site.

6. A bispecific antibody comprising at least one of polypeptide chain, wherein the polypeptide chain comprises:
an OX40 binding site, comprising:
a heavy chain variable region and a light chain variable region respectively comprising an amino acid sequence of amino acid 128-246 of SEQ ID NO: 10 and amino acid 1-112 of SEQ ID NO: 10;

and
a PD-L1 binding site, comprising:
  a heavy chain variable region and a light chain variable region respectively comprising an amino acid sequence of SEQ ID NO: 2 and amino acid 1-111 of SEQ ID NO: 1.

7. The bispecific antibody of claim 6, wherein the polypeptide chain further comprises:
  a Fc domain;
  a Fab fragment connected to a N-terminus of the Fc domain, wherein the Fab fragment comprises the PD-L1 binding site; and
  a scFv connected to a C-terminus of the Fc domain, wherein the scFv comprises the OX40 binding site.

8. The bispecific antibody of claim 7, wherein the polypeptide chain further comprises a linker between the Fc domain and the scFv.

9. The bispecific antibody of claim 6, wherein the bispecific antibody comprises two of said polypeptide chains.

10. The bispecific antibody of claim 9, wherein the bispecific antibody is an IgG, IgE, IgM, IgD, IgA, or IgY antibody.

11. The bispecific antibody of claim 10, wherein the bispecific antibody is an IgG antibody.

12. The bispecific antibody of claim 11, wherein the IgG antibody is an IgG1, IgG2, IgG3, or IgG4 antibody.

13. A pharmaceutical composition comprising the antibody or the antigen-binding portion thereof according to claim 1, and at least one pharmaceutically acceptable carrier.

14. A pharmaceutical composition comprising the bispecific antibody according to claim 6, and at least one pharmaceutically acceptable carrier.

15. An antibody-drug conjugate comprising:
  a therapeutic agent; and
  an antibody or an antigen-binding portion thereof binding PD-L1 and/or OX40, wherein the therapeutic agent is covalently conjugated to the antibody or the antigen-binding portion thereof by a linker;
  wherein the antibody or the antigen-binding portion thereof is:
  a) an antibody or an antigen-binding portion thereof binding to OX40, comprising:
    a heavy chain variable region and a light chain variable region respectively comprising an amino acid sequence of:
      amino acid 128-246 of SEQ ID NO: 10 and amino acid 1-112 of SEQ ID NO: 10;
  or
  b) a bispecific antibody comprising at least one polypeptide chain, wherein the polypeptide chain comprises:
  an OX40 binding site, comprising:
    a heavy chain variable region and a light chain variable region respectively comprising an amino acid sequence of amino acid 128-246 of SEQ ID NO: 10 and amino acid 1-112 of SEQ ID NO: 10;
  and
  a PD-L1 binding site, comprising:
    a heavy chain variable region and a light chain variable region respectively comprising an amino acid sequence of SEQ ID NO: 2 and amino acid 1-111 of SEQ ID NO: 1.

16. A method of treating cancer comprising administering to a subject in need thereof an effective amount of the antibody or the antigen-binding portion thereof according to claim 1.

17. The method of claim 16, wherein the cancer is selected from the group consisting of prostate cancer, lung cancer, Non-Small Cell Lung Cancer (NSCLC), melanoma, lymphoma, breast cancer, head and neck cancer, renal cell carcinoma (RCC), and ovarian cancer.

18. A method of treating cancer comprising administering to a subject in need thereof an effective amount of the bispecific antibody according to claim 6.

19. The method of claim 18, wherein the cancer is selected from the group consisting of prostate cancer, lung cancer, Non-Small Cell Lung Cancer (NSCLC), melanoma, lymphoma, breast cancer, head and neck cancer, renal cell carcinoma (RCC), and ovarian cancer.

* * * * *